United States Patent
Peled et al.

(10) Patent No.: US 12,202,803 B2
(45) Date of Patent: *Jan. 21, 2025

(54) SMALL MOLECULES FOR TREATING CANCER, INHIBITING CHEMOKINE ACTIVITY AND/OR INDUCING CELL DEATH

(71) Applicant: AlonBio Ltd., Nes Ziona (IL)

(72) Inventors: Amnon Peled, Tel-Aviv (IL); Michal Abraham Karni, Mevasseret Zion (IL); Orly Eizenberg, Rechovot (IL)

(73) Assignee: AlonBio Ltd., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/369,857

(22) Filed: Sep. 19, 2023

(65) Prior Publication Data
US 2024/0002347 A1 Jan. 4, 2024

Related U.S. Application Data

(63) Continuation of application No. 17/585,624, filed on Jan. 27, 2022, now Pat. No. 11,780,814, which is a continuation of application No. 16/988,765, filed on Aug. 10, 2020, now Pat. No. 11,261,159, which is a continuation of application No. PCT/IL2020/050535, filed on May 15, 2020.

(60) Provisional application No. 62/848,008, filed on May 15, 2019.

(51) Int. Cl.
C07D 215/22 (2006.01)
A61K 45/06 (2006.01)
A61P 35/04 (2006.01)

(52) U.S. Cl.
CPC ............ C07D 215/22 (2013.01); A61P 35/04 (2018.01); A61K 45/06 (2013.01)

(58) Field of Classification Search
CPC ........ C07D 215/22; A61P 35/04; A61K 45/06
See application file for complete search history.

(56) References Cited

U.S. PATENT DOCUMENTS

| | | |
|---|---|---|
| 5,116,964 A | 5/1992 | Capon et al. |
| 5,378,694 A | 1/1995 | Afonso et al. |
| 5,541,196 A | 7/1996 | Fournet et al. |
| 6,002,008 A | 12/1999 | Wissner et al. |
| 9,493,557 B2 | 11/2016 | Abraham et al. |
| 10,646,465 B2 | 5/2020 | Peled et al. |
| 11,129,824 B2 | 9/2021 | Peled et al. |
| 11,261,159 B2 | 3/2022 | Peled et al. |
| 11,780,814 B2 | 10/2023 | Peled et al. |
| 2008/0299130 A1 | 12/2008 | Ambati |
| 2011/0027643 A1 | 2/2011 | Li et al. |
| 2012/0087921 A1 | 4/2012 | Abraham et al. |
| 2013/0345212 A1 | 12/2013 | Daugan et al. |

(Continued)

FOREIGN PATENT DOCUMENTS

| | | |
|---|---|---|
| CA | 3008107 | 6/2017 |
| EA | 003933 | 10/2003 |

(Continued)

OTHER PUBLICATIONS

Grounds of Reason of Rejection Dated Mar. 25, 2024 From the Korean Intellectual Property Office Re. Application No. 10-2018-7020455. (5 Pages).

(Continued)

*Primary Examiner* — Timothy R Rozof

(57) ABSTRACT

Compounds capable of, or usable in, inducing death of cancer cells and/or modulating a biological activity of a chemokine e.g., cell migration, and/or treating diseases and disorders associated with a biological activity of a chemokine and/or cell migration, and/or in treating cancer, are provided herein. The compounds are collectively represented by Formulae Ia or Ib:

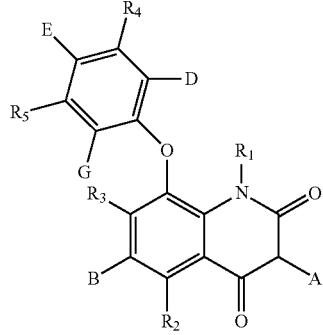

Formula Ia

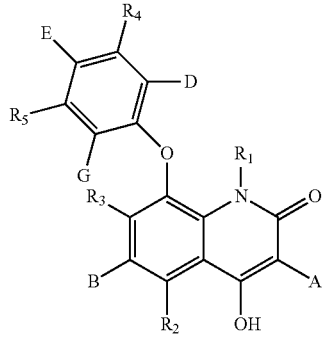

Formula Ib wherein A, B, D, E, G and $R_1$-$R_5$ are as defined in the specification, with one or more of D, E and G, preferably E, is hydroxy.

26 Claims, 25 Drawing Sheets

(56) References Cited

U.S. PATENT DOCUMENTS

| | | |
|---|---|---|
| 2014/0154249 A1 | 6/2014 | Abraham et al. |
| 2017/0015708 A1 | 1/2017 | Abraham et al. |
| 2017/0226157 A1 | 8/2017 | Peled |
| 2019/0240188 A1 | 8/2019 | Peled et al. |
| 2019/0336492 A1 | 11/2019 | Peled et al. |
| 2020/0268709 A1 | 8/2020 | Peled et al. |
| 2020/0369617 A1 | 11/2020 | Peled et al. |
| 2021/0228535 A1 | 7/2021 | Peled et al. |
| 2022/0008407 A1 | 1/2022 | Peled et al. |
| 2022/0144777 A1 | 5/2022 | Peled et al. |

FOREIGN PATENT DOCUMENTS

| | | |
|---|---|---|
| HU | 9903186 | 10/1999 |
| IN | IN2003CH00554 | 3/2005 |
| JP | 04-178647 | 6/1992 |
| JP | H08-268881 | 10/1996 |
| JP | 2003-512011 | 4/2003 |
| JP | 2003-530318 | 10/2003 |
| JP | 2018-531613 | 11/2018 |
| JP | 2019-502699 | 1/2019 |
| JP | 6941611 | 9/2021 |
| WO | WO 92/20642 | 11/1992 |
| WO | WO 95/15758 | 6/1995 |
| WO | WO 95/21613 | 8/1995 |
| WO | WO 97/30035 | 8/1997 |
| WO | WO 99/61428 | 12/1999 |
| WO | WO 00/10981 | 3/2000 |
| WO | WO 00/24782 | 5/2000 |
| WO | WO 00/56720 | 9/2000 |
| WO | WO 01/21598 | 3/2001 |
| WO | WO 02/42248 | 5/2002 |
| WO | WO 03/072599 | 9/2003 |
| WO | WO 2007/052173 | 5/2007 |
| WO | WO 2007/094005 | 8/2007 |
| WO | WO 2008/115870 | 9/2008 |
| WO | WO 2010/143168 | 12/2010 |
| WO | WO 2010/146584 | 12/2010 |
| WO | WO 2016/092544 | 6/2016 |
| WO | WO 2017/103931 | 6/2017 |
| WO | WO 2017/103932 | 8/2017 |
| WO | WO 2020/230144 | 11/2020 |
| WO | WO 2020/230144 A8 | 1/2021 |

OTHER PUBLICATIONS

Notification of Office Action and Search Report Dated Mar. 29, 2024 From the National Intellectual Property Administration of the People's Republic of China Re. Application No. 202080050533.4. (6 Pages).
Translation Dated Apr. 9, 2024 of Grounds of Reason of Rejection Dated Mar. 25, 2024 From the Korean Intellectual Property Office Re. Application No. 10-2018-7020455. (3 Pages).
Office Action Dated Apr. 7, 2024 From the Israel Patent Office Re Application No. 307561. (4 Pages).
Examination Report Dated Jul. 8, 2024 From the Instituto Mexicano de la Propiedad Industrial, Secretaria de Economia, Direccion Divisional de Patentes Re. Application No. MX/a/2021/014008 and Its Translation Into English. (12 Pages).
Communication Pursuant to Article 94(3) EPC Dated Dec. 19, 2023 From the European Patent Office Re. Application No. 20754606.0 (3 Pages).
Official Action Dated Mar. 19, 2024 from the US Patent and Trademark Office Re. U.S. Appl. No. 17/485,581. (15 pages).
Advisory Action Before the Filing of An Appeal Brief Dated Sep. 23, 2013 From the US Patent and Trademark Office Re. U.S. Appl. No. 13/378,063.
Communication Pursuant to Article 94(3) Dated Sep. 4, 2020 From the European Patent Office Re. Application No. 16875066.9. (6 Pages).
Communication Pursuant to Article 94(3) EPC Dated May 2, 2022 From the European Patent Office Re. Application No. 20185763.8. (3 Pages).
Communication Pursuant to Article 94(3) EPC Dated Jun. 3, 2019 From the European Patent Office Re. Application No. 16875067.7. (3 Pages).
Communication Pursuant to Article 94(3) EPC Dated May 3, 2023 From the European Patent Office Re. Application No. 20754606.0. (4 Pages).
Communication Pursuant to Article 94(3) EPC Dated Aug. 4, 2021 From the European Patent Office Re. Application No. 20185763.8. (4 Pages).
Communication Pursuant to Article 94(3) EPC Dated May 7, 2014 From the European Patent Office Re. Application No. 10735337.7.
Communication Pursuant to Article 94(3) EPC Dated Dec. 14, 2012 From the European Patent Office Re. Application No. 10735337.7.
Communication Relating to the Results of the Partial International Search Dated Feb. 26, 2017 From the International Searching Authority Re. Application No. PCT/IL2016/051346. (20 Pages).
European Search Report and the European Search Opinion Dated Aug. 21, 2020 From the European Patent Office Re. Application No. 20185763.8. (7 Pages).
Examination Report Dated Jan. 11, 2021 From the Servico Publico Federal, Ministerio da Economia, Instituto Nacional da Propriedade Industrial do Brasil RE Application No. BR1120180123064 and Its Translationsh into English. (7 Pages).
Examination Report Dated Aug. 13, 2020 From the Instituto Mexicano de la Propiedad Industrial, IMPI, Secretario de Economia, Direccion Divisional de Patentes Re. Application No. MX/a/2018/007361. (3 Pages).
Examination Report Dated Feb. 18, 2014 From the Instituto Mexicano de la Propiedad Industrial Re. Application No. MX/a/2011/013457 and Its Translation Into English.
Examination Report Dated Aug. 19, 2019 From the Australian Government, IP Australia Re. Application No. 2016371466. (2 Pages).
Examination Report Dated May 27, 2022 From the Instituto Mexicano de la Propiedad Industrial, Direccion Divisional de Patentes Re. Application No. MX/a/2020/011500 and Its Translation Into English. (8 Pages).
Examination Report Under Sections 12 & 13 of the Patents Act, 1970 and the Patents Rules, 2003 Dated Apr. 26, 2020 From the Government of India, Intellectual Property India, Patents, Designs, Trade Marks, Geographical Indications, The Patent Office Re. Application No. 201837025290. (5 Pages).
International Preliminary Report on Patentability Dated Jun. 22, 2017 From the International Bureau of WIPO Re. Application No. PCT/IL2015/051190. (8 Pages).
International Preliminary Report on Patentability Dated Nov. 25, 2021 From the International Bureau of WIPO Re. Application No. PCT/IL2020/050535. (7 Pages).
International Preliminary Report on Patentability Dated Jun. 28, 2018 From the International Bureau of WIPO Re. Application No. PCT/IL2016/051346. (11 Pages).
International Preliminary Report on Patentability Dated Jun. 28, 2018 From the International Bureau of WIPO Re. Application No. PCT/IL2016/051347. (7 Pages).
International Preliminary Report on Patentability Dated Dec. 29, 2011 From the International Bureau of WIPO Re. Application No. PCT/IL2010/000473.
International Search Report and the Written Opinion Dated Mar. 19, 2017 From the International Searching Authority Re. Application No. PCT/IL2016/051347. (10 Pages).
International Search Report and the Written Opinion Dated Oct. 22, 2010 From the International Searching Authority Re. Application No. PCT/IL2010/000473.
International Search Report and the Written Opinion Dated Mar. 28, 2016 From the International Searching Authority Re. Application No. PCT/IL2015/051190.
International Search Report and the Written Opinion Dated Mar. 29, 2017 From the International Searching Authority Re. Application No. PCT/IL2016/051346. (33 Pages).
International Search Report and the Written Opinion Dated Jul. 30, 2020 From the International Searching Authority Re. Application No. PCT/IL2020/050535. (11 Pages).

(56) References Cited

OTHER PUBLICATIONS

Notice of Allowance Dated Jul. 1, 2016 From the US Patent and Trademark Office Re. U.S. Appl. No. 14/178,301.
Notice of Allowance Dated Jan. 16, 2020 From the US Patent and Trademark Office Re. U.S. Appl. No. 16/063,278. (9 pages).
Notice of Allowance Dated Nov. 16, 2020 from the US Patent and Trademark Office Re. U.S. Appl. No. 16/868,558. (31 pages).
Notice of Allowance Dated Oct. 20, 2021 from the US Patent and Trademark Office Re. U.S. Appl. No. 16/988,765. (42 pages).
Notice of Allowance Dated May 26, 2021 From the US Patent and Trademark Office Re. U.S. Appl. No. 16/063,279. (9 Pages).
Notice of Allowance Dated May 26, 2023 from the US Patent and Trademark Office Re. U.S. Appl. No. 17/585,624. (5 pages).
Notice of Allowance Dated Oct. 29, 2013 From the US Patent and Trademark Office Re. U.S. Appl. No. 13/378,063.
Notice of Preliminary Rejection Dated Feb. 8, 2017 From the Korean Intellectual Property Office Re. Application No. 2012-7000920. (6 Pages).
Notice of Reason for Rejection Dated Dec. 8, 2020 From the Japan Patent Office Re. Application No. 2018-531613. and Its Translation Into English. (5 Pages).
Notice of Reason for Rejection Dated Oct. 17, 2014 From the Japanese Patent Office Re. Application No. 2012-515627 and Its Translation Into English.
Notification of Office Action and Search Report Dated Nov. 20, 2020 From the State Intellectual Property Office of the People's Republic of China Re. Application No. 201680081132.9 and Its Translation of Office Action Into English. (10 Pages).
Notification of Office Action Dated Oct. 31, 2013 From the State Intellectual Property Office of the People's Republic of China Re. Application No. 201080036127.9 and Its Translation Into English.
Office Action Dated Dec. 8, 2022 From the Israel Patent Office Re. Application No. 288144. (4 Pages).
Office Action Dated Jul. 8, 2013 From the Israel Patent Office Re. Application No. 216978 and Its Translation Into English.
Office Action Dated Jun. 11, 2020 From the Israel Patent Office Re. Application No. 260081 and Its Translation Into English. (5 Pages).
Office Action Dated Mar. 11, 2021 From the Israel Patent Office Re. Application No. 277261 and Its Translation Into English. (5 Pages).
Office Action Dated Nov. 17, 2019 From the Israel Patent Office Re. Application No. 260082 and Its Translation Into English. (7 Pages).
Office Action Dated Mar. 26, 2015 From the Israel Patent Office Re. Application No. 216978 and Its Translation Into English.
Official Action Dated Jul. 1, 2013 From the US Patent and Trademark Office Re. U.S. Appl. No. 13/378,063.
Official Action Dated Aug. 2, 2023 from the US Patent and Trademark Office Re. U.S. Appl. No. 17/485,581. (103 pages).
Official Action Dated Feb. 2, 2023 from the US Patent and Trademark Office Re. U.S. Appl. No. 17/585,624. (63 pages).
Official Action Dated Feb. 5, 2021 From the US Patent and Trademark Office Re. U.S. Appl. No. 16/063,279. (60 Pages).
Official Action Dated Jul. 7, 2015 From the US Patent and Trademark Office Re. U.S. Appl. No. 14/178,301.
Official Action Dated Jan. 8, 2013 From the US Patent and Trademark Office Re. U.S. Appl. No. 13/378,063.
Official Action Dated Feb. 9, 2016 From the US Patent and Trademark Office Re. U.S. Appl. No. 14/178,301.
Official Action Dated Jun. 15, 2020 from the US Patent and Trademark Office Re. U.S. Appl. No. 16/868,558. (9 pages).
Official Action Dated Sep. 20, 2019 From the US Patent and Trademark Office Re. U.S. Appl. No. 16/063,278. (25 pages).
Official Action Dated Aug. 21, 2017 From the US Patent and Trademark Office Re. U.S. Appl. No. 15/326,512. (42 pages).
Official Action Dated Aug. 28, 2017 From the US Patent and Trademark Office Re. U.S. Appl. No. 15/285,492. (31 pages).
Official Action Dated Oct. 28, 2022 from the US Patent and Trademark Office Re. U.S. Appl. No. 17/214,993. (56 pages).
Patent Examination Report Dated Aug. 23, 2021 From the Australian Government, IP Australia Re. Application No. 2020200524. (2 Pages).
Relatório de Exame Tecnico [Technical Examination Report] Dated Feb. 24, 2023 From the Serviço Público Federal, Ministério da Economia, Instituto Nacional da Propriedade Industrial do Brasil Re. Application No. BR 11 2018 012306 4. (4 Pages).
Request for Examination Dated Aug. 25, 2023 From the Federal Government Institution, Federal Institute of Industrial Property of the Federal Service of Intellectual Property, Patents and Trademarks of the Russian Federation, FIPS Re. Application No. 2021136077. and Its Machine Translation Into English. (15 Pages).
Request for Examination and Search Report Dated Apr. 3, 2020 From the Federal Government Institution, Federal Institute of Industrial Property of the Federal Service of Intellectual Property, Patents and Trademarks of the Russian Federation, FIPS Re. Application No. 2018125293 and Its Translation Into English. (11 Pages).
Request for Examination Dated Oct. 2, 2020 From the (ROSPATENT), Federal Government Institution of Industrial Property of the Federal Service of Intellectual Property, Patents and Trademark of the Russian Federation Re. Application No. 2018125293 and Its Translation Into English. (10 Pages).
Requisition by the Examiner Dated Oct. 4, 2021 From the Innovation, Science and Economic Development Canada, Canadian Intellectual Property Office Re. Application No. 3,008,107. (3 Pages).
Requisition by the Examiner Dated Oct. 5, 2021 From the Innovation, Science and Economic Development Canada, Canadian Intellectual Property Office Re. Application No. 3,090,315. (4 Pages).
Requisition by the Examiner Dated Mar. 21, 2022 From the Innovation, Science and Economic Development Canada, Canadian Intellectual Property Office Re. Application No. 3,008,107 with Claims. (11 Pages).
Requisition by the Examiner Dated Oct. 21, 2022 From the Innovation, Science and Economic Development Canada, Canadian Intellectual Property Office Re. Application No. 3,090,315 with Claims. (9 Pages).
Requisition by the Examiner Dated May 25, 2016 From the Canadian Intellectual Property Office Re. Application No. 2,765,188.
Requisition by the Examiner Dated Jun. 27, 2017 From the Canadian Intellectual Property Office Re. Application No. 2,765,188. (8 Pages).
Requisition by the Examiner Dated Mar. 28, 2022 From the Innovation, Science and Economic Development Canada, Canadian Intellectual Property Office Re. Application No. 3,090,315 wit Claims. (9Pages).
Restriction Official Action Dated Jul. 2, 2019 From the US Patent and Trademark Office Re. U.S. Appl. No. 16/063,278. (7 pages).
Restriction Official Action Dated Mar. 10, 2015 From the US Patent and Trademark Office Re. U.S. Appl. No. 14/178,301.
Restriction Official Action Dated Nov. 17, 2020 From the US Patent and Trademark Office Re. U.S. Appl. No. 16/063,279. (6 Pages).
Restriction Official Action Dated Aug. 23, 2012 From the US Patent and Trademark Office Re. U.S. Appl. No. 13/378,063.
Supplementary European Search Report and the European Search Opinion Dated Nov. 7, 2019 From the European Patent Office Re. Application No. 16875066.9. (13 Pages).
Supplementary European Search Report and the European Search Opinion Dated Sep. 19, 2018 From the European Patent Office Re. Application No. 16875067.7. (5 Pages).
Supplementary European Search Report and the European Search Opinion Dated Sep. 21, 2021 From the European Patent Office Re. Application No. 20754606.0. (9 Pages).
Supplementary Partial European Search Report and the European Provisional Opinion Dated Aug. 5, 2019 From the European Patent Office Re. Application No. 16875066.9. (18 Pages).
Translation Dated Sep. 18, 2023 Request for Examination Dated Aug. 25, 2023 From the Federal Government Institution, Federal Institute of Industrial Property of the Federal Service of Intellectual Property, Patents and Trademarks of the Russian Federation, FIPS Re. Application No. 2021136077. and Its Machine Translation Into English. (6 Pages).
Translation of Notice of Preliminary Rejection Dated Feb. 8, 2017 From the Korean Intellectual Property Office Re. Application No. 2012-7000920. (4 Pages).

(56) References Cited

OTHER PUBLICATIONS

Translation of Office Action Dated May 2, 2013 From the State Intellectual Property Office of the People's Republic of China Re. Application No. 201080036127.9.
Translation of Search Report May 2, 2013 From the State Intellectual Property Office of the People's Republic of China Re. Application No. 201080036127.9.
Baggiolini et al. "CC Chemokines in Allergic Inflammation", Immunology Today, 15(3): 127-133, 1994.
Bork "Powers and Pitfalls in Sequence Analysis: The 70% Hurdle", Genome Research, 10: 398-400, 2000.
Carreras Puigvert et al. "Targeting DNA Repair, DNA Metabolism and Replication Stress as Anti-Cancer Strategies", The FEBS Journal, XP055607460, 283(2): 232-245, Published Online Oct. 28, 2015.
Cocchi et al. "Identification of RANTES, MIP-1[Alpha], and MIP-1[Beta] as the Major HIV-Suppressive Factors Produced by CD8+ T Cells", Science, 270(5243): 1811-1815, Dec. 15, 1995.
Debnath et al. "Small Molecule Inhibitors of CXCR4", Theranostics, XP055391478, 3(1): 47-75, Jan. 15, 2013. Abstract, Figs.
Doercks et al. "Protein Annotation: Detective Work for Function Prediction", Trends in Genetics, TiG, 14(6): 248-250, Jun. 1998.
Duan et al. "Inhaled P38[Alpha] Mitogen-Activated Protein Kinase Antisense Oligonucleotide Attenuates Asthma in Mice", American Journal of Respiratory and Critical Care Medicine, 171: 571-578, Originally Published Nov. 19, 2004.
Elix et al. "Annelated Furans. XVIII. The Photocyclization of 2-Methoxyphenyl Phenyl Ethers", Australian Journal of Chemistry, 28(7): 1559-1582, Dec. 31, 1975. p. 1562, Compounds 11, 12, 14.
Epifano et al. "Auraptene and Its Effects on the Re-Emergence of Colon Cancer Stem Cells", Phytotherapy Research, 27(5): 784-786, Epub Jul. 4, 2012.
Escott et al. "Effect of the P38 Kinase Inhibitor, SB 203580, on Allergic Airway Inflammation in the Rat", British Journal of Pharmacology, 131(2): 173-176, Sep. 2000.
Haddad et al. "Role of P38 MAP Kinase in LPS-Induced Airway Inflammation in the Rat", British Journal of Pharmacology, 132(8): 1715-1724, Apr. 2001.
Hu et al. "Design, Synthesis, and Biological Evaluation of Novel Quinazoline Derivatives as Anti-Inflammatory Agents Against Lipopolysaccharide-Induced Acute Lung Injury in Rats", Chemical Biology & Drug Design, 85(6): 672-684, Published Online Nov. 6, 2014. Schemes 1, p. 7, Compounds 6a, 6b, 6c, 6d, 6g, 6i, Schemes 1, p. 7, 6o, 6p, 6q, Scheme 2, p. 7.
Huang et al. "Anticancer Activities of Polyynes From the Root Bark of Oplopanax Horridus and Their Acetylated Derivatives", Molecules, 19: 6142-6162, May 14, 2014.
Joulain et al. "Lichen Extracts as Raw Materials in Perfumery. Part 2: Treemoss", Flavour and Fragrance Journal, 24(3): 105-116, Mar. 11, 2009. p. 5, Fig.4, Compounds 32-33.
Kasuga et al. "Sensitization of Human Glioblastomas to Tumor Necrosis Factor-Related Apoptosis-Inducing Ligand (TRAIL) by NF-KB Inhibitors", Cancer Science, 95(10): 840-844, Oct. 2004.
Kim et al. "Isolation and Characterization of Antitumor Agents From Dictamnus Albus", Saengyak Hakhoe Chi, 28(4): 209-214, Dec. 28, 1997.
Kioi et al. "Inhibition of Vasculogenesis, But Not Angiogenesis, Prevents the Recurrence of Glioblastoma After Irradiation in Mice", the Journal of Clincal Investigation, 120(3): 694-705, Mar. 2010.
Kryczek et al. "Stroma-Derived Factor (SDF-1/CXCL12) and Human Tumor Pathogenesis", American Journal of Physioloy, Cell Physiology, 292(3): C987-C995, First Published Aug. 30, 2006.
Lee et al. "Ocular Neovascularization: An Epidemiologic Review", Survey of Ophthalmology, 43(3): 245-269, Nov.-Dec. 1998.
Lo et al. "High Level Expression and Secretion of Fc-X Fusion Proteins in Mammalian Cells", Protein Engineering, 11(6): 495-500, Jun. 1998.
Luhmann et al. The Relevance of Chemokine Signalling in Modulating Inherited and Age-Related Retinal Degenerations:, Retinal Degenerative Diseases, Chap.54: 427-433, Mar. 25, 2014.
Ma et al. "Impaired B-Lymphopoiesis, Myelopoiesis, and Derailed Cerebellar Neuron Migration in CXCR4- and SDF-1-Deficient Mice", Proc. Natl. Acad. Sci. USA, 95(16): 9448-9453, Aug. 1998.
Mathebula "A Review of Ocular Genetics and Inherited Eye Diseases", African Vision and Eye Health, 71(4): 179-189. 2012.
Niu et al. "New Polyphenols From a Deep sea *Spiromastix* Sp. Fungus, and Their Antibacterial Activities", Marine Drugs, 13(4): 2526-2540, Apr. 22, 2015. Fig.1, Compound 9, p. 2527.
Nomura et al. "Effects of Oakmoss and Its Components on Biofilm Formation of Legionella Pneumophila", Biological and Pharmaceutical Bulletin, 36(5): 833-837, May 2013. Compounds 14, 17, 20, p. 834.
Nomura et al. "The Antibacterial Activity of Compounds Isolated From Oakmoss Against Legionella Pneumophila and Other *Legionella* Spp.", Biological & Pharmaceutical Bulletin, XP055391465, 35(9): 1560-1567, Jun. 20, 2012. p. 1562-1563, Fig.1, Table 1, Compounds 14, 17, 20.
Reeck et al. "'Homology' in Proteins and Nucleic Acids: A Terminology Muddle and a Way Out of It", Cell, 50(5): 667, Aug. 28, 1987.
Rutar et al. "Small Interfering RNA-Mediated Suppression of Ccl2 in Mueller Cells Attenuates Microglial Recruitment and Photoreceptor Death Following Retinal Degeneration", Journal of Neuroinflammation, 9(221): 1-15, Published Online Sep. 19, 2012.
Sechi et al. "Design and Synthesis of Novel Dihydroquinoline-3-Carboxylic Acids as HIV-1 Integrase Inhibitors", Bioorganic & Medicinal Chemistry, 17(7): 2925-2935, Available Online Nov. 6, 2008.
Skolnick et al. "From Genes to Protein Structure and Function: Novel Applications of Computational Approaches in the Genomic Era", Trends in Biotechnology, TiBTech, 18(1): 34-39, Jan. 2000.
Smith et al. "CXCR4 Regulates Growth of Both Primary and Metastatic Breast Cancer", Cancer Research, 64: 8604-8612, Dec. 1, 2004.
Stedman "Allograft Rejection", Stedman's Online, Lippincott Williams and Wilkins, Jun. 23, 2015.
Stedman "Malignant", Stedman's Online, Lippincott Williams and Wilkins, Jun. 23, 2015.
Stedman "Myasthenia Gravis", Stedman's Online, Lippincott Williams and Wilkins, Jun. 23, 2015.
Stedman "Systemic Lupus Erythematosus" Stedman's Online, Lippincott Williams and Wilkins, Jun. 23, 2015.
Strieter et al. "The Functional Role of the ELR Motif in CXC Chemokine-Mediated Angiogenesis", The Journal of Biological Chemistry, 270(45): 27348-27357, Nov. 10, 1995.
Sulaiman et al. "In Vitro and In Silico Studies of Lunacridine From Lunasia Amara Blanco as Anticancer", Journal of Life Sciences, 5(8): 639-645, Published Online Aug. 30, 2011. Abstract.
Tannock et al. "The Basic Science of Oncology", Third Edition, New York: McGraw-Hill; p. 357-358, 1998.
Tokuriki et al. "Stability Effects of Mutations and Protein Evolvability", Current Opinion in Structural Biology, 19: 596-604, 2009.
Toyooka et al. "CD28 Co-Stimulatory Signals Induce IL-2 Receptor Expression on antigen-Stimulated Virgin T Cells by an IL-2-Independent Mechanism", International Immunology, 8(2): 159-169, Feb. 1996.
Underwood et al. "SB 239063, a P38 MAPK Inhibitor, Reduces Neutrophilia, Inflammatory Cytokines, MMP-9, and Fibrosis in Lung", American Journal of Physiology, Lung Cellular and Molecular Physiology, 279(5): L895-L902, Nov. 2000.
Underwood et al. "SB 239063, a Potent P38 MAP Kinase Inhibitor, Reduces Inflammatory Cytokine Production, Airways Eosinophil Infiltration, and Persistence", The Journal of Pharmacology and Experimental Therapeutics, 293(1): 281-288, Apr. 2000.
Vaddi et al. "Regulation of Monocyte Integrin Expression by Beta-Family Chemokines", The Journal of Immunology, 153(10): 4721-4732, Nov. 15, 1994.
Wallace et al. "The Role of Chemokines and Their Receptors in Ocular Disease", Progress in Retinal and Eye Research, 23(4): 435-448, Jul. 2004. p. 446, Pont No. 10.
Wang et al. "Identification of Potential Anticancer Compounds From Oplopanax Horridus", Phytomedicine, 20(11): 999-1006, Aug. 15, 2013.

(56) References Cited

OTHER PUBLICATIONS

Wells "Additivity of Mutational Effects in Proteins", Biochemistry, 29(37): 8509-8517, Sep. 18, 1990.
Williams et al. "Depsides Isolated From the Sri Lankan Lichen *Parmotrema* Sp. Exhibit Selective Plk1 Inhibitory Activity", Pharmaceutical Biology, XP055607658, 49(3): 296-301, Feb. 1, 2011.
Wilson et al. "CXCR4 Signaling Mediates Morphine-Induced Tactile Hyperalgesia", Brain, Behavior, and Immunity, 25(3): 565-573, Epub Dec. 28, 2010.
Zheng et al. "Migration of Endothelial Progenitor Cells Mediated by Stromal Cell-Derived Factor-1 [Alpha]/CXCR4 via P13K/Akt/eNOS Signal Transduction Pathway", Journal of Cardiovascular Pharmacology, 50(3): 274-280, Sep. 2007.
Advisory Action Dated Jun. 26, 2024 From the US Patent and Trademark Office Re. U.S. Appl. No. 17/485,581. (4 pages).
Notice of Reason(s) for Rejection Dated Apr. 30, 2024 From the Japan Patent Office Re. Application No. 2021-568695 and Its Translation Into English. (7 Pages).
Translation Dated Apr. 12, 2024 of Notification of Office Action Dated Mar. 29, 2024 From the National Intellectual Property Administration of the People's Republic of China Re. Application No. 202080050533.4. (6 Pages).

continuation

SMALL MOLECULES FOR TREATING CANCER, INHIBITING CHEMOKINE ACTIVITY AND/OR INDUCING CELL DEATH

RELATED APPLICATIONS

This application is a Continuation of U.S. patent application Ser. No. 17/585,624 filed on Jan. 27, 2022, which is a Continuation of U.S. patent application Ser. No. 16/988,765 filed on Aug. 10, 2020, now U.S. Pat. No. 11,261,159, which is a Continuation of PCT Patent Application No. PCT/IL2020/050535 having International Filing Date of May 15, 2020, which claims the benefit of priority under 35 USC § 119(e) of U.S. Provisional Patent Application No. 62/848,008 filed on May 15, 2019. The contents of the above applications are all incorporated by reference as if fully set forth herein in their entirety.

FIELD AND BACKGROUND OF THE INVENTION

The present invention, in some embodiments thereof, relates to therapy and more particularly, but not exclusively, to small molecule compounds which are useful in modulating a biological activity of a chemokine, in killing cancer cells, in inhibiting chemokine-dependent cell migration and/or in treating diseases and disorders associated with biological activities of chemokines and/or cell migration, such as cancer, and to methods utilizing these compounds.

Chemokines are among the many biological factors that are involved in the inflammatory disease process. Chemokines belong to a group of small, about 8-14 kDa, mostly basic, heparin-binding proteins that are related both in their primary structure and the presence of four conserved cysteine residues.

The chemokines are chemotactic cytokines that have been shown to be selective chemoattractants for leukocyte subpopulations in vitro, and to elicit the accumulation of inflammatory cells in vivo. In addition to chemotaxis, chemokines mediate leukocyte de-granulation [Baggiolini and Dahinden, *Immunol Today* 1994, 15:127-133], up-regulation of adhesion receptors [Vaddi and Newton, *J Immunol* 1994, 153:4721-4732], and suppression of human immunodeficiency virus replication [Cocchi et al., *Science* 1995, 270:1811-1815].

Chemokines play an essential role in the recruitment and activation of cells from the immune system. They also have a wide range of effects in many different cell types beyond the immune system, including for example, in various cells of the central nervous system [Ma et al., *PNAS* 1998, 95:9448-9453], and in endothelial cells, where they result in either angiogenic or angiostatic effects [Strieter et al., *J Biol Chem* 1995, 270:27348-27357]. Particular chemokines may have multiple effects on tumors, including angiogenesis, promotion of growth and metastasis, and suppression of the immune response to cancer, while other chemokines inhibit tumor-mediated angiogenesis and promote anti-tumor immune responses.

Chemokine receptors have received increasing attention due to their critical role in the progression of inflammation and associated conditions such as asthma, atherosclerosis, graft rejection, AIDS and autoimmune conditions (e.g., multiple sclerosis, arthritis, myasthenia gravis, lupus).

SDF-1 (stromal cell-derived factor 1), also known as CXCL12 (C-X-C motif chemokine 12), is a chemokine which is strongly chemotactic for lymphocytes. SDF-1 plays an important role in angiogenesis, including angiogenesis associated with tumor progression, by recruiting endothelial progenitor cells from the bone marrow, an effect mediated by the CXCR4, the receptor for SDF-1 [Zheng et al., *Cardiovasc Pharmacol* 2007, 50:274-280; Kryczek et al., *Am J Physiol Cell Physiol* 2007, 292:C987-C995]. In addition, cancer cells that express CXCR4 are attracted to metastasis target tissues that release SDF-1.

Plerixafor, an antagonist of CXCR4, is used in combination with G-CSF (granulocyte colony-stimulating factor) to mobilize hematopoietic stem cells in cancer patients, particularly lymphoma and multiple myeloma patients. The stem cells are subsequently transplanted back to the patient after chemotherapy or radiotherapy.

In animal studies, plerixafor has also been reported to reduce metastasis [Smith et al., *Cancer Res* 2004, 64:8604-8612], to reduce recurrence of glioblastoma associated with vasculogenesis [Kioi et al., *J Clin Investigation* 2010, 120:694-705], and to counteract opioid-induced hyperalgesia [Wilson et al., *Brain Behav Immun* 2011, 25:565-573].

WO 2017/103931, by the present assignee, which is incorporated by reference as if fully set forth herein, describes data obtained upon screening and further studying a library of natural compounds for compounds which are capable of modulating chemokine activity. In the studies described in WO 2017/103931, compounds which are characterized by certain structural features were identified as capable of modulating the effect of individual chemokines on cells, and as capable of affecting cancer and other pathogenic cells. WO 2017/103931 describes the compound referred to therein as BKT300 (as shown below) as, for example, inducing cancer cell death and as inhibiting cancer cell migration.

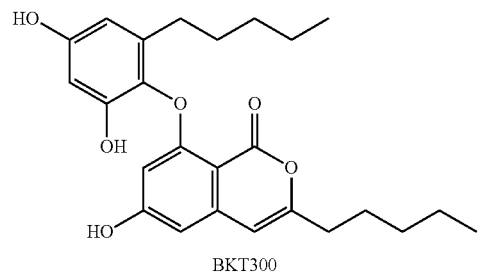

BKT300

WO 2017/103932, by the present assignee, which is incorporated by reference as if fully set forth herein, describes newly designed structural analogs of BKT300, which were shown to induce death of cancer cells, to inhibit cancer cell migration, to selectively arrest cancer cell proliferation at G2M and to induce apoptotic cell death through the Caspase 3 pathway. One of the compounds described in WO 2017/103932 is referred to as BKT300-3-05, as shown below in its keto and enol forms.

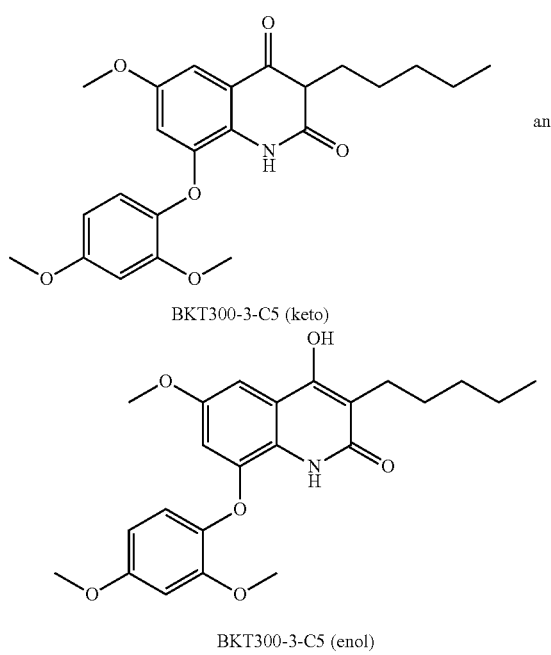

BKT300-3-C5 (keto)

and/or

BKT300-3-C5 (enol)

SUMMARY OF THE INVENTION

According to an aspect of some embodiments of the present invention there is provided a compound represented by Formula Ia and/or Ib:

Formula Ia

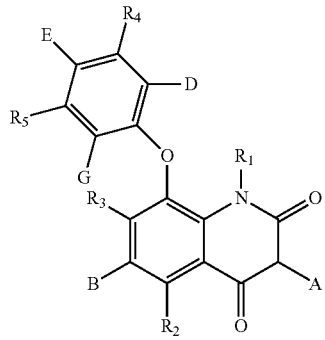

Formula Ib

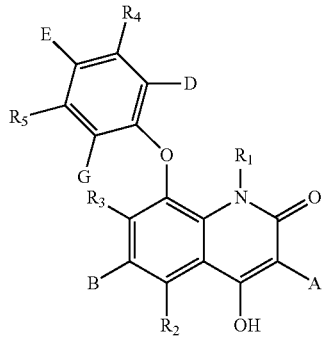

wherein:
A is an alkyl being at least 4 carbon atoms in length;
B is selected from hydroxy and alkoxy;
D and G are each independently selected from hydrogen, hydroxy, alkoxy and alkyl, provided that at least one of D and G is hydrogen;
E is hydroxy;
$R_1$ is selected from hydrogen and alkyl; and
each of $R_2$-$R_5$ is independently selected from hydrogen, hydroxy, halo, alkoxy, thioalkoxy, thiol, thioalkoxy and amine.

According to some of any of the embodiments described herein, B is alkoxy.

According to some of any of the embodiments described herein, one of D and G is alkoxy.

According to some of any of the embodiments described herein, when one of D and G is alkyl, the alkyl is at least 4 carbon atoms in length.

According to some of any of the embodiments described herein, $R_1$ is hydrogen.

According to some of any of the embodiments described herein, each of $R_2$-$R_5$ is hydrogen.

According to some of any of the embodiments described herein, the compound is represented by Formula IIa or IIb:

Formula IIa

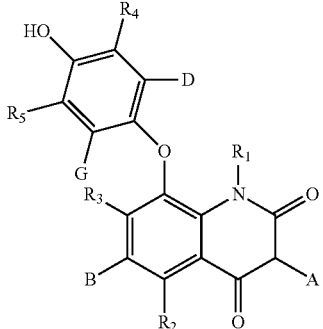

Formula IIb

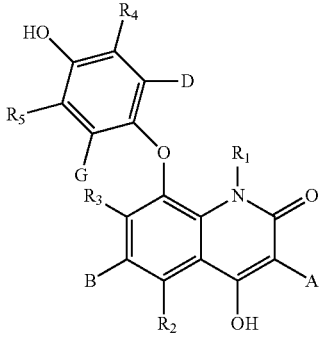

wherein:
A is an alkyl being at least 4 carbon atoms in length;
B is selected from hydroxy and alkoxy;
D and G are each independently selected from hydrogen, hydroxy, alkoxy and alkyl, provided that at least one of D and G is hydrogen;
$R_1$ is selected from hydrogen and alkyl; and
each of $R_2$-$R_5$ is independently selected from hydrogen, hydroxy, halo, alkoxy, thioalkoxy, thiol, thioalkoxy and amine.

According to some of any of the embodiments described herein, each of $R_2$-$R_5$ is hydrogen.

According to some of any of the embodiments described herein, $R_1$ is hydrogen.

According to some of any of the embodiments described herein, at least one of D and G is alkoxy.

According to some of any of the embodiments described herein, B is alkoxy.

According to some of any of the embodiments described herein, the compound is:

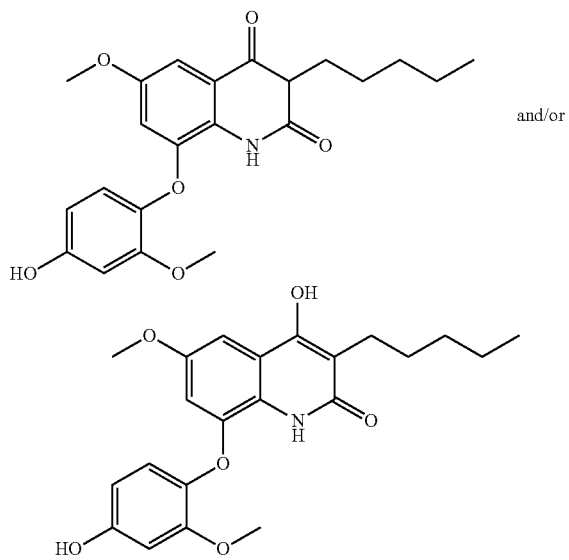

and/or

This exemplary compound is referred to herein as BKT300-N1.

According to some of any of the embodiments described herein, the compound is capable of inducing cells death.

According to some of any of the embodiments described herein, the compound capable of inducing apoptosis in cells.

According to some of any of the embodiments described herein, the apoptosis is associated with cleavage of caspase-3.

According to some of any of the embodiments described herein, the compound is capable of inducing arrest of cancer cell growth at the G2M phase of cancer cells.

According to some of any of the embodiments described herein, the compound is capable of inhibiting chemokine-induced cell migration.

According to an aspect of some embodiments of the present invention, a compound represented by Formula Ia and/or Ib or by Formula IIa and/or IIb, as described herein in any of the respective embodiments and any combination thereof, is for use in treating cancer in a subject in need thereof.

According to some of any of the embodiments described herein, the cancer is a leukemia.

According to some of any of the embodiments described herein, the cancer is selected from a leukemia, a melanoma, a lung cancer, a lymphoma, a myeloma, an ovarian cancer, a liver cancer, a brain cancer, a colorectal cancer and a prostate cancer.

According to some of any of the embodiments described herein, the cancer is a drug-resistant cancer.

According to some of any of the embodiments described herein, treating the cancer further comprises administering to the subject an additional anti-cancer agent.

According to an aspect of some embodiments of the present invention, a compound represented by Formula Ia and/or Ib or by Formula IIa and/or IIb as described herein in any of the respective embodiments and any combination thereof is for use in modulating a biological activity of a chemokine in a subject in need thereof.

According to an aspect of some embodiments of the present invention, a compound represented by Formula Ia and/or Ib or by Formula IIa and/or IIb as described herein in any of the respective embodiments and any combination thereof is for use in treating a condition treatable by modulating a biological activity of a chemokine.

According to some of any of the embodiments described herein, the chemokine is SDF-1.

According to some of any of the embodiments described herein, the chemokine is MCP-1.

According to some of any of the embodiments described herein, the condition is age-related macular degeneration.

According to some of any of the embodiments described herein, the disease or disorder is cancer.

According to an aspect of some embodiments of the present invention, a compound represented by Formula Ia and/or Ib or by Formula IIa and/or IIb as described herein in any of the respective embodiments and any combination thereof is for use in treating inflammation.

According to an aspect of some embodiments of the present invention, a compound represented by Formula Ia and/or Ib or by Formula IIa and/or IIb as described herein in any of the respective embodiments and any combination thereof is for use in treating a non cancerous hyperproliferative disease.

According to an aspect of some embodiments of the present invention, a compound represented by Formula Ia and/or Ib or by Formula IIa and/or IIb as described herein in any of the respective embodiments and any combination thereof is for use in inducing cell death. According to an aspect of some embodiments of the present invention, a compound represented by Formula Ia and/or Ib or by Formula IIa and/or IIb as described herein in any of the respective embodiments and any combination thereof is for use in inducing apoptosis in cells.

According to some of any of the embodiments described herein, the apoptosis is associated with cleavage of caspase-3.

According to some of any of the embodiments described herein, the cells are cancer cells.

According to some of any of the embodiments described herein, the cells are drug-resistant cells (e.g., drug-resistant cancer cells).

According to an aspect of some embodiments of the present invention, a compound represented by Formula Ia and/or Ib or by Formula IIa and/or IIb as described herein in any of the respective embodiments and any combination thereof is for use in inducing arrest of cancer cell growth at the G2M phase of cancer cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 13B) and colorectal cancer (FIG. 13C in xenografts (PDX), compared to vehicle only.

FIG. 17A presents % of dead cells following treatment; FIG. 17B presents % of cells in the G0/G1 phase following treatment; and FIG. 17C presents % of cells in G2/M phase following treatment. *$p<0.05$.

FIG. 18A presents % of dead cells following treatment; FIG. 18B presents % of cells in the G0/G1 phase following treatment; and FIG. 18C presents % of cells in G2/M phase following treatment. *$p<0.05$.

DESCRIPTION OF SPECIFIC EMBODIMENTS OF THE INVENTION

The present invention, in some embodiments thereof, relates to therapy and more particularly, but not exclusively, to small molecule compounds which are useful in modulating a biological activity of a chemokine, in killing cancer cells, in inhibiting chemokine-dependent cell migration and/or in treating diseases and disorders associated with biological activities of chemokines and/or cell migration, such as cancer, and to methods utilizing these compounds.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed in the Background section hereinabove, the present assignee has previously uncovered, using laborious screening assays, that small molecules which feature certain structural features are capable of modulating the effect of individual chemokines on cells, and of affecting cancer and other pathogenic cells, and have further designed structural analogs of some of these small molecules, which were found to exhibit even improved effect on chemokine activity and in inducing cancer cell death. See, WO 2017/103931 and WO 2017/103932.

In a search for further compounds which modulate an activity of a chemokine and/or are capable of inducing death of cancer and other pathogenic cells, the present inventors have uncovered that a modification of the structure of the compounds taught in WO 2017/103932 leads to substantial improvement in the desired activity of these compounds.

Without being bound by any particular theory, the present inventors have uncovered that compounds which feature one or more hydroxy substituents, possibly by replacing one or more alkoxy groups in compounds such as described in WO 2017/103932, exhibit an improved effect.

Figure 1:
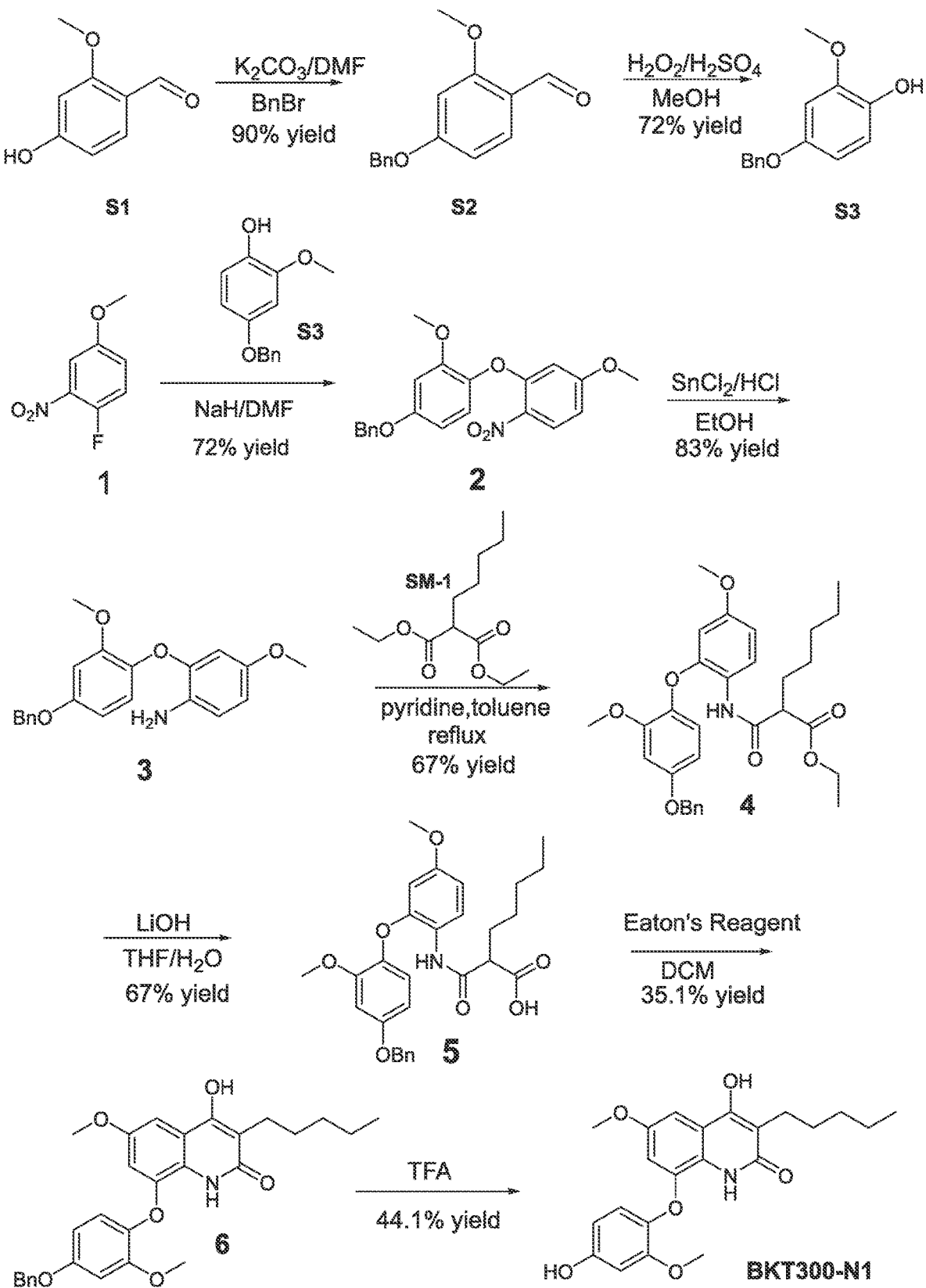
FIG. 1 presents a scheme depicting a synthesis of BKT300-N1, according to some embodiments of the present invention.

An exemplary synthetic pathway for preparing an exemplary such compound, referred to herein as BKT300-N1, is shown in FIG. 1.

The present inventors have shown that an exemplary such compound, referred to herein as BKT300-N1, which features a modification in the structure of the compound referred to in WO 2017/103932 as BKT300-3-05, exhibits an improved effect in modulating a biological activity of chemokines (see, for example, FIGS. 2-5B) and as an anti-cancer agent, by inducing cancer cells death and/or effecting cancel cells migration and/or growth, by acting in synergy with another anti-cancer agent, and by inducing cancer cells death and arresting cancer cells growth of taxol-resistant cancer cells. Reference is made, for example, to FIGS. 6A-18C.

The modified compounds described herein are useful in modulating a biological activity of chemokines, and accordingly in treating diseases or disorders associated with a biological activity of a chemokine, as described in further detail hereinafter. The modified compounds described herein are particularly useful as anti-cancer agents, by inducing cancer cells death and/or arresting cell growth and/or effecting cancer cells migration (by inhibiting angiogenesis and/or metastasis), as described in further detail hereinbelow.

The general effect of compounds of some embodiments of the invention is shown on various biological phenotypes including chemokine-induced cell migration and apoptosis. These findings place the compounds described herein as potent pharmaceuticals, which can be used in the treatment of various medical conditions including inflammation (e.g., autoimmune diseases), cancer and non-cancerous hyperproliferative diseases.

Embodiments of the present invention therefore generally relate to newly designed small molecules and to uses thereof.

The Compounds (Small Molecules):

According to an aspect of some embodiments of the present invention there are provided newly designed small molecules (compounds) which can be collectively represented by Formula Ia:

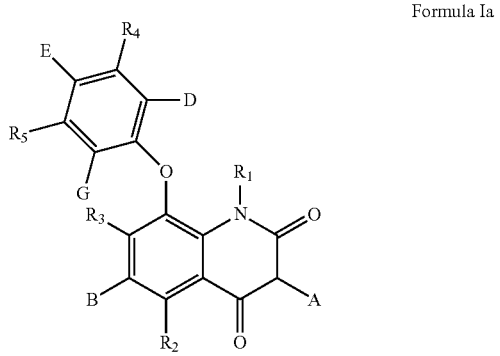

Formula Ia wherein:
A is an alkyl being at least 4 carbon atoms in length;
B is selected from hydroxy, alkoxy and aryloxy, or from hydroxyl and alkoxy; D, E and G are each independently selected from hydrogen, hydroxy, alkoxy, aryloxy and alkyl, provided that one of D, E and G is hydroxy;
$R_1$ is selected from hydrogen, alkyl and cycloalkyl, or from hydrogen and alkyl; and
each of $R_2$-$R_5$ is independently selected from hydrogen, hydroxy, halo, alkoxy, thioalkoxy, thiol, thioalkoxy, amine, and optionally alkyne, aryloxy, thioaryloxy, carboxylate, carbonyl, sulfonyl, sulfonate, sulfinyl, cyano, nitro, and other substituents, as described herein.

Compound of Formula Ia feature a ketone group (carbonyl), and, can undergo a keto-enol tautomerization into the "enol" form, and thus be represented alternatively by Formula Ib:

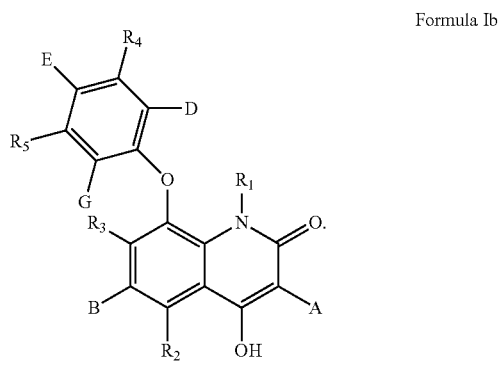

Formula Ib

Keto-enol tautomerization is known in the art as describing the rapid equilibrium between a carbonyl group (C=O) and its enol tautomer.

The keto-enol tautomerization is in most cases thermodynamically driven, and at room temperature, the equilibrium typically favors the formation of the keto form. However, environmental conditions such as, for example, the pH or ionic strength of a solution, the compound's concentration, the temperature, a presence of an agent that stabilizes the enol form, may shift the equilibrium towards the enol form being equally present or predominating.

In some embodiments, and depending on the environmental conditions, the compounds according to the present embodiments can be in the form of the keto tautomer (Formula Ia), or in the form of the enol form (Formula Ib), or can be equilibrating between the keto and enol forms, and thus take both forms of Formula Ia and Ib.

In some of any of the embodiments described herein, at least one of B, D, E and G is alkoxy or aryloxy, preferably alkoxy, and in some embodiments, at least two of B, D, E and G are alkoxy and/or aryloxy, preferably each being alkoxy.

In some of any of the embodiments described herein, the alkoxy is of 1-6 carbon atoms, preferably 1-4 carbon atoms. Examples include, without limitation, methoxy, ethoxy, propoxy, isopropoxy, butoxy and isobutoxy.

In some of any of the embodiments described herein, the alkoxy is methoxy.

In some of any of the embodiments described herein, B is alkoxy (e.g., methoxy).

In some of any of the embodiments described herein, no more than one of D, E and G is an alkyl.

In some of any of the embodiments described herein, no more than two, or no more than one of D, E and G are/is alkoxy or aryloxy.

In some of any of the embodiments described herein, when two of D, E and G are alkoxy and/or aryloxy, none of D, E and G is an alkyl.

In some of any of the embodiments described herein, at least one of D, E and G is hydroxy and at least one of D, E and G is hydrogen. In some of these embodiments, the other one or more of D, E and G can be alkoxy, aryloxy and/or alkyl, preferably alkoxy and/or alkyl, more preferably alkoxy.

In some of any of the embodiments described herein, E is hydroxy, D is hydrogen, and G is alkyl.

In some of any of the embodiments described herein, D is hydrogen, E is hydroxy and G is an alkoxy, for example, methoxy.

In some of any of the embodiments described herein, D is an alkoxy, for example, methoxy, E is hydroxy and G is hydrogen.

In some of any of the embodiments described herein, one of D and G is an alkoxy, for example, methoxy, the other one of D and G is hydroxy, and E is hydrogen.

In some of any of the embodiments described herein, one of D and G is hydrogen, the other one of D and G is alkyl and E is hydroxy.

In some of any of the embodiments described herein, E is hydrogen, D is alkyl and G is hydroxy.

In some of any of the embodiments described herein, G is hydrogen, E is alkyl and D is hydroxy.

In some of any of the embodiments described herein, D is hydrogen, G is alkyl and E is hydroxy.

In some of any of the embodiments described herein, E is hydrogen, G is alkyl and D is hydroxy.

In some of any of the embodiments described herein, G is hydrogen, D is alkyl and E is hydroxy.

In some of any of the embodiments described herein, E is hydrogen, D is alkoxy, for example, methoxy, and G is hydroxy.

In some of any of the embodiments described herein, G is hydrogen, E is alkoxy, for example, methoxy, and D is hydroxy.

In some of any of the embodiments described herein, D is hydrogen, G is hydroxy and E is alkoxy, for example, methoxy.

In some of any of the embodiments described herein, E is hydrogen, G is alkoxy, for example, methoxy, and D is hydroxy.

In some of any of the embodiments described herein, E is hydroxy.

In some of any of the embodiments described herein, B is alkoxy (e.g., methoxy).

In some of any of the embodiments described herein, D is alkoxy (e.g., methoxy).

In some of any of the embodiments described herein, G is hydrogen.

In some of any of the embodiments described herein, E is hydroxy, D is alkoxy (e.g., methoxy) and G is hydrogen. In some of these embodiments, B is alkoxy (e.g., methoxy).

In some of any of the embodiments described herein, E is hydroxy, G is alkoxy (e.g., methoxy) and D is hydrogen. In some of these embodiments, B is alkoxy (e.g., methoxy).

In some of any of the embodiments described herein, E is hydroxy, and D and G are both hydrogen. In some of these embodiments, B is alkoxy (e.g., methoxy).

In some of any of the embodiments described herein, D is hydroxy and E and G are both hydrogen. In some of these embodiments, B is alkoxy (e.g., methoxy).

In some of any of the embodiments described herein, G is hydroxy, and D and E are both hydrogen. In some of these embodiments, B is alkoxy (e.g., methoxy).

In some of any of the embodiments described herein, D is said alkyl.

In some of these embodiments, one of G and E is hydrogen. In some of these embodiments, G is hydrogen and E is hydroxy.

In some of any of the embodiments described herein, E is hydroxy, D is alkyl and G is hydrogen. In some of these embodiments, B is alkoxy (e.g., methoxy).

In some of any of the embodiments described herein, whenever one of D, E and G is alkyl, the alkyl is at least 4 carbon atoms in length.

In some of any of the embodiments described herein, an alkyl being at least 4 carbon atoms in length can be, for example, of 1 to 20, or of 1 to 10, or of 1 to 8 carbon atoms in length. Exemplary alkyls being at least 4 carbon atoms in length include substituted or unsubstituted butyl, substituted or unsubstituted pentyl, substituted or unsubstituted hexyl, substituted or unsubstituted heptyl, substituted or unsubstituted octyl, substituted or unsubstituted nonyl, substituted or unsubstituted decyl, substituted or unsubstituted undecyl, substituted or unsubstituted dodecyl, and so forth.

In some of any of the embodiments described herein, the alkyl being 4 carbon atoms in length is an unsubstituted alkyl. In some embodiments, it is hexyl, and in some embodiments, an unsubstituted hexyl.

In some of any of the embodiments described herein, A is an alkyl being at least 4 carbon atoms in length, and optionally one of D, E and G is an alkyl being at least 4 carbon atoms in length.

When both A and one of D, E, and G are an alkyl being 4 carbon atoms in length, these alkyls can be the same or different.

In some of these embodiments, both A and one of D, E and G are an unsubstituted alkyl and in some embodiments, both are unsubstituted hexyl.

In some of any of the embodiments described herein, $R_1$ is hydrogen.

In some of any of the embodiments described herein, each of $R_2$-$R_5$ is independently selected from hydrogen, hydroxy, halo, alkoxy, thioalkoxy, thiol, thioalkoxy, and amine.

In some of any of the embodiments described herein, each of $R_2$-$R_5$ is hydrogen.

In some of any of the embodiments described herein, each of $R_1$-$R_5$ is hydrogen.

Alternatively, one or more of $R_1$-$R_5$ is other than hydrogen and the nature of the respective substituent(s) is such that does not interfere with the interactions of the small molecule with its biological target(s) (e.g., chemokine binding).

According to some of any of the embodiments of the present invention, the compounds of the present embodiments can be collectively represented by Formula IIa or IIb:

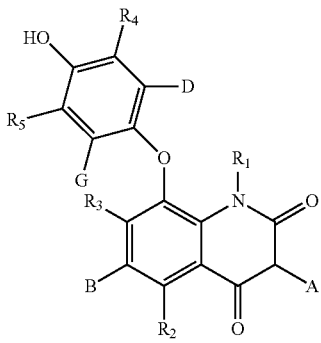

Formula IIa

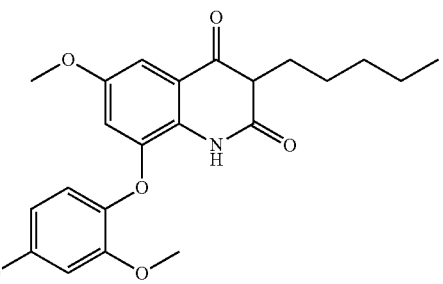

and/or

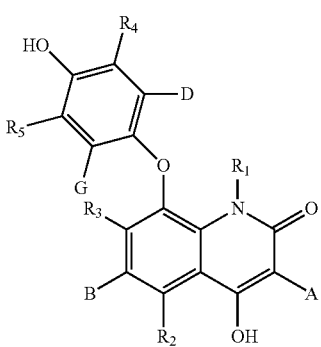

Formula IIb

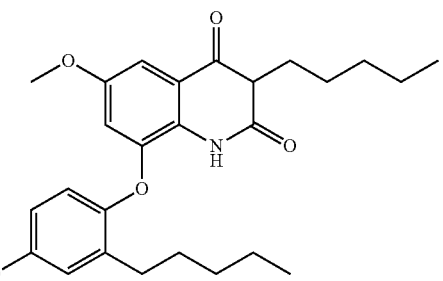

.

This compound is denoted herein BKT300-N1.

In some of any of the embodiments described herein, a compound as described herein has the following chemical structure, represented by its keto and enol tautomers:

wherein:

A is an alkyl being at least 4 carbon atoms in length;

B is selected from hydroxy and alkoxy;

D and G are each independently selected from hydrogen, hydroxy, alkoxy and alkyl, provided that at least one of D and G is hydrogen;

R₁ is selected from hydrogen and alkyl; and each of R₂-R₅ is independently selected from hydrogen, hydroxy, halo, alkoxy, thioalkoxy, thiol, thioalkoxy and amine.

According to some of any of these embodiments, each of R₂-R₅ is hydrogen.

According to some of any of these embodiments, R₁ is hydrogen.

According to some of any of these embodiments, at least one of D and G is alkoxy. Alternatively, or in addition, at least one of D and G is an alkyl, as described herein in any of the respective embodiments. Further alternatively, or in addition, at least one of D and G is hydroxy.

According to some of any of these embodiments, D and G are each hydrogen.

In some of any of these embodiments B is alkoxy. Optionally, B is hydroxy.

In some of any of the embodiments described herein, a compound as described herein has the following chemical structure, represented by its keto and enol tautomers:

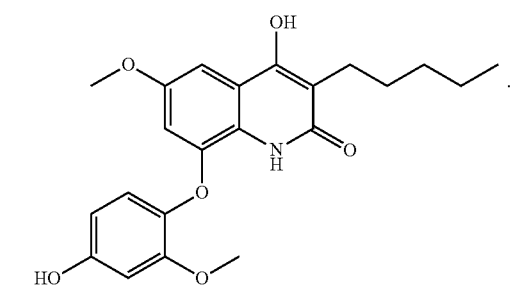

and/or

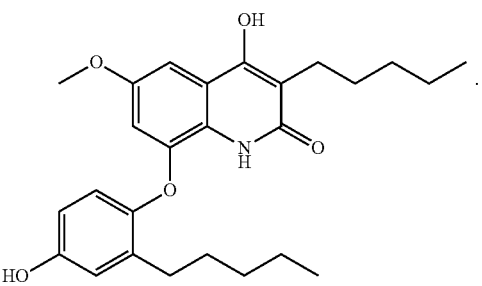

.

In some of any of the embodiments described herein, a compound as described herein has the following chemical structure, represented by its keto and enol tautomers:

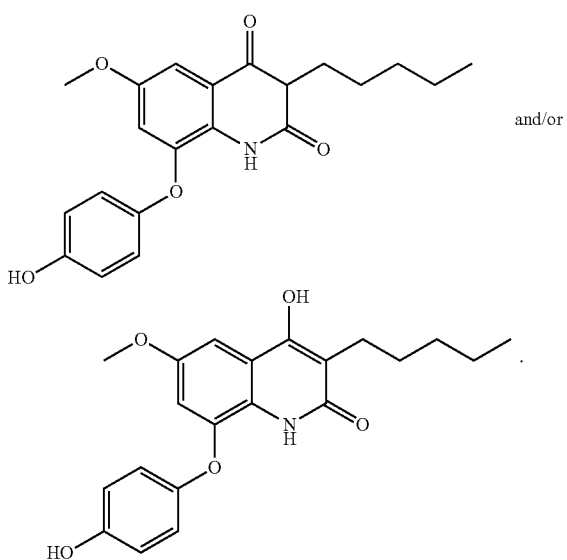

In some of any of the embodiments described herein, a compound as described herein has the following chemical structure, represented by its keto and enol tautomers:

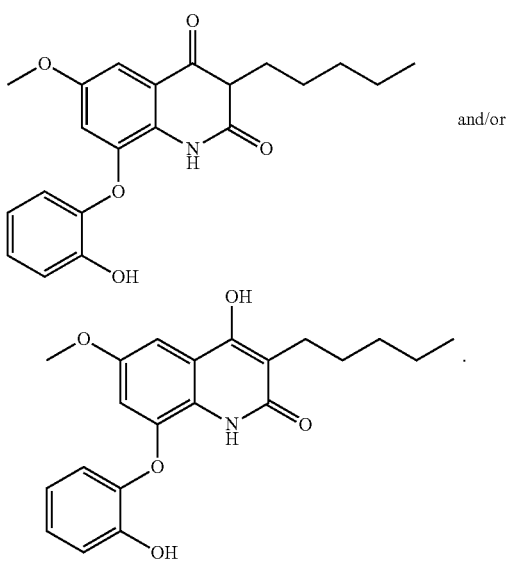

Therapeutic Applications:

The compounds as described herein, in any one of the respective embodiments, and any combination thereof, are shown herein to act as inhibitors of chemokine-dependent cell migration, and as inhibitors of cancer cells (e.g., as inhibitors of cancer cells growth and/or as inducing apoptosis and/or as inhibitor of cancer cells migration).

Each of the compounds described herein is therefore capable of, or is useful in, inhibiting cancer cells, and/or killing cancer cells, and/or inducing apoptosis, and/or inducing growth arrest, and/or inhibiting chemokine-dependent cell migration, and/or modulating a biological activity of a chemokine e.g., cell migration, and/or treating diseases and disorders associated with cell migration, such as cancer and inflammatory diseases and disorders; and/or treating proliferative diseases or disorders (where inducing apoptosis and/or growth arrest is desirable).

As inflammation and cancer are typically governed by cell migration (e.g., infiltration, metastasis), which is often associated with cell proliferation, such conditions are contemplated for treatment using the compounds according to the present embodiments.

Proliferative diseases and disorders as described herein, including medical conditions other than cancer (also referred to herein as "non-cancerous hyperproliferative diseases"), are also contemplated for treatment using the compounds of some embodiments of the invention, due to the apoptosis-inducing effect of the compounds.

Without being bound by any particular theory, it is believed that the compounds described herein are particularly useful as anti-cancer agents by inducing cancer cell death, by affecting chemokine-dependent cancer cell migration (e.g., by inhibiting metastasis) and/or angiogenesis, and/or by inducing apoptosis of cancer cells and/or by inducing growth arrest of cancer cells; and/or as anti-inflammatory agents by affecting chemokine-dependent immune cell migration (e.g., immune cell infiltration), as described in further detail hereinbelow.

In some of any of the embodiments described herein, a small molecule compound of Formula Ia and/or Ib, or of Formula IIa and/or IIb, as described herein in any of the respective embodiments, is capable of, or usable in, inducing death of pathogenic cells (e.g., cancer cells or immune cells or hyper-proliferating cells).

In some of any of the embodiments described herein, a small molecule compound of Formula Ia and/or Ib, or of Formula IIa and/or IIb, as described herein in any of the respective embodiments, is capable of, or usable in, inducing cell death of pathogenic cells.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Methods of monitoring cellular changes induced by the compounds are known in the art and include for example, the MTT test which is based on the selective ability of living cells to reduce the yellow salt MTT (3-(4, 5-dimethylthiaz-olyl-2)-2, 5-diphenyltetrazolium bromide) (Sigma, Aldrich St Louis, MO, USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); 7-ADD viability staining (available from MD systems), caspase-3 assay (available from MDsystems) as well as various RNA and protein detection methods (which detect level of expression and/or activity) which are further described hereinabove.

In some of any of the embodiments described herein, a small molecule compound of Formula Ia and/or Ib, or of Formula IIa and/or IIb, as described herein in any of the respective embodiments, the cellular change is apoptosis such as via cleavage of caspase-3.

In some of any of the embodiments described herein, a small molecule compound of Formula Ia and/or Ib, or of Formula IIa and/or IIb, as described herein in any of the respective embodiments, is capable of, or usable in, inducing apoptosis via cleavage of caspase-3.

In some of any of the embodiments described herein, a small molecule compound of Formula Ia and/or Ib, or of Formula IIa and/or IIb, as described herein in any of the respective embodiments, is capable of, or usable in, inducing growth arrest of cells, and in some embodiments, the arrest is at the G2M phase of the cell cycle. In some of these embodiments, the cells are cancer cells.

Chemokine Modulation:

According an aspect of some embodiments of the present invention, a small molecule compound of Formula Ia and/or Ib, or of Formula IIa and/or IIb, as described herein in any of the respective embodiments, and any combination thereof, is capable of, or is usable, in modulating a biological activity of a chemokine, as described herein.

According to an aspect of some embodiments of the present invention, there is provided a method of modulating a biological activity of a chemokine, the method comprising contacting the chemokine with a compound according to any of the embodiments described herein.

According to an aspect of some embodiments of the present invention, there is provided a use of a compound according to any of the embodiments described herein in the manufacture of a medicament for modulating a biological activity of a chemokine.

According to an aspect of some embodiments of the present invention, there is provided a use of a compound according to any of the embodiments described herein in modulating a biological activity of a chemokine.

In some embodiments, the use and/or method for modulating a chemokine activity is effected in vivo, for example by administering a therapeutically effective amount of the compound to a subject in need thereof.

In some embodiments, the use and/or method for modulating a chemokine activity is effected ex vivo (e.g., in vitro), for example, in research.

In some embodiments of any one of the embodiments described herein relating to a method, use or medicament for modulating a biological activity of a chemokine, the method, use or medicament is for treating a disease or disorder associated with a biological activity of a chemokine in a subject in need thereof, for example, by administering to the subject a therapeutically effective amount of a compound according to any of the embodiments described herein.

In some of any of the embodiments described herein, modulating a biological activity of a chemokine includes inhibiting a biological activity of a chemokine. This can be evidenced by the ability of a small molecule as described herein to inhibit chemokine-induced cell migration as exemplified herein on a plurality of cell types of different types.

In some embodiments of any one of the embodiments described herein relating to a method, use or medicament for modulating a biological activity of a chemokine, the method, use or medicament is for treating a disease or disorder in which modulating (e.g., inhibiting) a biological activity of a chemokine is beneficial, in a subject in need thereof, for example, by administering to the subject a therapeutically effective amount of a compound according to any of the embodiments described herein.

In some embodiments of any one of the embodiments described herein relating to a method, use or medicament for modulating a biological activity of a chemokine, the method, use or medicament is for treating a disease or disorder treatable by modulating (e.g., inhibiting) a biological activity of a chemokine, in a subject in need thereof, for example, by administering to the subject a therapeutically effective amount of a compound according to any of the embodiments described herein.

In some embodiments of any one of the embodiments described herein relating to a method, use or medicament for modulating a biological activity of a chemokine, the compound described herein (according to any of the respective embodiments) is effective in modulating chemokine-dependent cell migration. In some of these embodiments, the chemokine-dependent cell migration is associated with cancer and/or inflammation, as described herein.

In some embodiments of any one of the embodiments described herein relating to a method or use for modulating a biological activity of a chemokine, the chemokine is MCP-1 and/or SDF-1. In some such embodiments, the chemokine is MCP-1. In some such embodiments, the chemokine is SDF-1.

In some embodiments of any one of the embodiments described herein relating to modulating a chemokine activity, the compound, method and/or medicament (according to any of the respective embodiments described herein) is for inhibiting a biological activity of a chemokine. In some such embodiments, the chemokine is MCP-1 and/or SDF-1. In some such embodiments, the chemokine is MCP-1. In some such embodiments, the chemokine is SDF-1.

In some of any of the embodiments described herein, the chemokine is MIP3a.

Examples of diseases and disorders associated with an activity of MIP3a (e.g., wherein inhibition of MIP3a activity is beneficial) include, without limitation, autoimmune diseases and disorders such as psoriasis, inflammatory bowel disease, chronic obstructive pulmonary diseases (COPD), rheumatoid arthritis, multiple sclerosis (MS), atopic dermatitis, dry eye disease and age-related macular degeneration (AMD).

In some embodiments of any one of the embodiments described herein relating to a treatment of a disease or disorder, the disease or disorder is not a bacterial infection.

SDF-1 and/or CXCR4 Inhibition:

According to some embodiments, a small molecule compound of Formula Ia and/or Ib, as described herein in any of the respective embodiments, and any combination thereof, is capable of, or is usable, in modulating a biological activity of SDF-1 and/or CXCR4, as described herein.

According to an aspect of some embodiments of the present invention, there is provided a method of inhibiting a biological activity of SDF-1 and/or CXCR4, the method comprising contacting the SDF-1 and/or CXCR4 with a compound according to any of the embodiments described herein described herein.

According to an aspect of some embodiments of the present invention, there is provided a use of a compound according to any of the embodiments described herein described herein in the manufacture of a medicament for inhibiting a biological activity of SDF-1 and/or CXCR4.

According to an aspect of some embodiments of the present invention, there is provided a use of a compound according to any of the embodiments described herein described herein in inhibiting a biological activity of SDF-1 and/or CXCR4.

In some embodiments of any of the embodiments relating to a use and/or method for inhibiting a biological activity of SDF-1 and/or CXCR4, the use and/or method is effected in vivo, for example, by administering a therapeutically effective amount of the compound to a subject in need thereof.

In some embodiments, the use and/or method for inhibiting a biological activity of SDF-1 and/or CXCR4 is effected ex vivo (e.g., in vitro), for example, in research.

In some embodiments of any one of the embodiments described herein relating to a method, use or medicament for inhibiting a biological activity of SDF-1 and/or CXCR4, the method, use or medicament is for treating a disease or disorder associated with a biological activity of SDF-1 and/or CXCR4 in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of SDF-1 and/or CXCR4, the method, use or medicament is for treating a disease or disorder in which inhibiting a biological activity of a SDF-1 and/or CXCR4 is beneficial, in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of SDF-1 and/or CXCR4, the method, use or medicament is for treating a disease or disorder treatable by inhibiting a biological activity of a SDF-1 and/or CXCR4 is beneficial, in a subject in need thereof, for example, by administering to the subject a therapeutically effective amount of a compound according to any of the embodiments described herein described herein.

The skilled person will appreciate that CXCR4 is a receptor which mediates activity of SDF-1, and that activities of SDF-1 and activities of CXCR4 typically overlap.

Examples of diseases and disorders associated with an activity of SDF-1 and/or CXCR4 (e.g., wherein inhibition of SDF-1 and/or CXCR4 activity is beneficial) include, without limitation, Whim Syndrome; Cervical Adenocarcinoma; Breast Cancer; Bursitis; Tuberculosis; Intraocular Lymphoma; Cytomegalovirus Retinitis; Chronic Inflammatory Demyelinating Polyradiculoneuropathy; Ocular Hypertension; Polyradiculoneuropathy; Dendritic Cell Tumor; Retinal Hemangioblastoma; Malaria; Endotheliitis; Leukemia; Rheumatoid Arthritis; Arthritis; Prostatitis; Prostate Cancer; Colorectal Cancer; Chronic Lymphocytic Leukemia; Pancreatitis; Neuronitis; Lung Cancer; Osteoarthritis; Hypoxia; Adenocarcinoma; Pancreatic Cancer; Multiple Myeloma; Neuroblastoma; Myeloid Leukemia; Astrocytoma; Periodontitis; Glioblastoma; Pre-Eclampsia; Melanoma; Hepatitis; Esophagitis; Myeloma; Eclampsia; Cervicitis; Periodontal Disease; Central Nervous System Lymphoma; Sporadic Breast Cancer; Hepatocellular Carcinoma; Systemic Lupus Erythematosus; Asthma; Renal Cell Carcinoma; Myocardial Infarction; Medulloblastoma; Endometrial Cancer; Lupus Erythematosus; Esophageal Cancer; Premature Ovarian Failure; Peritonitis; Vascular Disease; Alcoholic Hepatitis; Kidney Disease; Cutaneous Leishmaniasis; Encephalitis; Alopecia Areata; Lymphoblastic Leukemia; Adenoma; Mantle Cell Lymphoma; Oligodendroglioma; Malt Lymphoma; Pertussis; Ischemia; Uveal Melanoma; Gingivitis; Pituitary Adenoma; Bronchiolitis; Neuromyelitis Optica; Mesothelioma; Alopecia; Cervical Cancer, Somatic; Glioblastoma Multiforme; Bronchiolitis Obliterans; Brain Injury; Colorectal Adenoma; Tongue Squamous Cell Carcinoma; B-Cell Lymphomas; Traumatic Brain Injury; Intravascular Large B-Cell Lymphoma; Allergic Asthma; Tick-Borne Encephalitis; Blastic Plasmacytoid Dendritic Cell; Oligoastrocytoma; Childhood Type Dermatomyositis; Renal Oncocytoma; Endometrial Adenocarcinoma; Optic Neuritis; Seminoma; Sjogren's Syndrome; Pleurisy; Neuritis; Inflammatory Bowel Disease; Cytomegalovirus Infection; Malignant Pleural Mesothelioma; Oral Squamous Cell Carcinoma; Skeletal Muscle Regeneration; Emery-Dreifuss Muscular Dystrophy, Dominant Type.

In some embodiments, exemplary diseases and disorders associated with an activity of SDF-1 and/or CXCR4 (e.g., wherein inhibition of SDF-1 and/or CXCR4 activity is beneficial) include, without limitation, harmful angiogenesis, tumor metastasis, WHIM syndrome, Waldenstrom macroglobuolinaemia (WM) and opioid-induced hyperalgesia.

Herein, the term "harmful angiogenesis" refers to angiogenesis associated with a clinically and/or cosmetically undesirable result.

Angiogenesis associated with a tumor is a non-limiting example of a harmful angiogenesis.

As used herein the phrase "tumor metastasis" refers to a malignant tumor spreading out of its primary location to other parts of the body, e.g., breast cancer which metastasizes to the lungs. Tumor metastasis often involves migration of tumor cells.

In some embodiments of any one of the embodiments described herein relating to a method or use for modulating a biological activity of a chemokine, the modulating comprises inhibiting a biological activity of SDF-1 and/or CXCR4, according to any of the respective embodiments described herein.

In some embodiments of any one of the embodiments described herein relating to inhibiting a biological activity of SDF-1 and/or CXCR4, inhibiting a biological activity of SDF-1 and/or CXCR4 is for effecting immunostimulation.

In some embodiments, immunostimulation is effected as part of a cancer treatment, e.g., in order to stimulate immune activity against cancer cells.

In some embodiments, immunostimulation comprises increasing a level of hematopoietic stem cells in peripheral blood of a subject.

In some embodiments, increasing a level of hematopoietic stem cells in peripheral blood of a subject is effected as a preliminary part of hematopoietic stem cell transplantation (e.g., in order to generate hematopoietic stem cells available for collection and later transplantation back into the subject). Examples of conditions which may be treated by the hematopoietic stem cell transplantation include, without limitation, leukemia (e.g., acute lymphoblastic leukemia, acute myeloid leukemia, chronic lymphocytic leukemia, chronic myelogenous leukemia), lymphoma (e.g., Hodgkin's disease, non-Hodgkin's lymphoma), myeloma (e.g., multiple myeloma), neuroblastoma, desmoplastic small round cell tumor, Ewing's sarcoma, choriocarcinoma, myelodysplasia, anemias (e.g., paroxysmal nocturnal hemoglobinuria, aplastic anemia, Diamond-Blackfan anemia, Fanconi anemia, acquired pure red cell aplasia), hemoglobinopathies, sickle cell disease, beta-thalassemia major, myeloproliferative disorders (e.g., polycythemia vera, essential thrombocytosis, myelofibrosis), amyloid light chain amyloidosis, radiation poisoning, viral diseases (e.g., HTLV and/or HIV infection), neuronal ceroid lipofuscinosis, Niemann-Pick disease, Gaucher disease, leukodystrophies (adrenoleukodystrophy, metachromatic leukodystrophy, Krabbe disease), mucopolysaccharidosis, glycoproteinoses (e.g., mucolipidosis II, fucosidosis, asp artylglucosaminuria, alpha-mannosidosis), Wolman disease, immunodeficiencies (e.g., ataxia telangiectasia, DiGeorge syndrome, severe combined immunodeficiency, Wiskott-Aldrich syndrome, Kostmann syndrome, Shwachman-Diamond syndrome, Griscelli syndrome, NF-kappa-B essential modulator deficiency), amegakaryocytic thrombocytopenia and hemophagocytic lymphohistiocytosis.

In some embodiments, the hematopoietic stem cell transplantation is for treating a proliferative disease, e.g., cancer (e.g., cancer as described herein according to any of the respective embodiments).

In some embodiments of any one of the embodiments described herein relating to hematopoietic stem cells, the treatment comprises increasing a level of hematopoietic stem cells in peripheral blood of the subject, obtaining hematopoietic stem cells from peripheral blood of the subject, administering a cytotoxic therapy to the subject (e.g., anti-proliferative chemotherapy, and/or radiotherapy), and transplanting at least a portion of the stem cells back into the patient, subsequent to the cytotoxic therapy.

MCP-1 Inhibition:

According to some embodiments, a small molecule compound of Formula Ia and/or Ib, as described herein in any of the respective embodiments, and any combination thereof, is capable of, or is usable, in modulating a biological activity of MCP-1, as described herein.

According to an aspect of some embodiments of the present invention, there is provided a method of inhibiting a biological activity of MCP-1, the method comprising contacting the MCP-1 with a compound according to any of the embodiments described herein described herein.

According to an aspect of some embodiments of the present invention, there is provided a use of a compound according to any of the embodiments described herein described herein in the manufacture of a medicament for inhibiting a biological activity of MCP-1.

According to an aspect of some embodiments of the present invention, there is provided a use of a compound according to any of the embodiments described herein described herein in inhibiting a biological activity of MCP-1.

In some embodiments of any of the embodiments relating to a use and/or method for inhibiting a biological activity of MCP-1, the use and/or method is effected in vivo, for example, by administering a therapeutically effective amount of the compound to a subject in need thereof.

In some embodiments, the use and/or method for inhibiting a biological activity of MCP-1 is effected ex vivo (e.g., in vitro), for example, in research.

In some embodiments of any one of the embodiments described herein relating to a method, use or medicament for inhibiting a biological activity of MCP-1, the method, use or medicament is for treating a disease or disorder associated with a biological activity of MCP-1 in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of MCP-1, the method, use or medicament is for treating a disease or disorder in which inhibiting a biological activity of a MCP-1 is beneficial, in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of MCP-1, the method, use or medicament is for treating a disease or disorder treatable by inhibiting a biological activity of a MCP-1 is beneficial, in a subject in need thereof, for example, by administering to the subject a therapeutically effective amount of a compound according to any of the embodiments described herein described herein.

Examples of diseases and disorders associated with an activity of MCP-1 (e.g., wherein inhibition of MCP-1 activity is beneficial) include, without limitation, diseases and disorders which are characterized by monocytic infiltrates.

According to some embodiments, examples of diseases and disorders associated with an activity of MCP-1 (e.g., wherein inhibition of MCP-1 activity is beneficial) include, without limitation, tuberculosis; HIV-1; proliferative glomerulonephritis; neural tube defects; xanthogranulomatous pyelonephritis; scleritis; rapidly progressive glomerulonephritis; pneumoconiosis; encephalitis; peritonitis; atherosclerosis; psoriasis; dengue shock syndrome; temporal arteritis; relapsing polychondritis; diabetic angiopathy; mesangial proliferative glomerulonephritis; sympathetic ophthalmia; ureteral disease; lupus nephritis; pneumonia; periapical granuloma; erdheim-chester disease; glomerulonephritis; artery disease; viral encephalitis; primary cutaneous amyloidosis; arteriosclerosis; nonspecific interstitial pneumonia; acute poststreptococcal glomerulonephritis; coronary artery disease; venezuelan equine encephalitis; diabetic macular edema; extrapulmonary tuberculosis; nephritis; rheumatoid arthritis; kawasaki disease; arthritis; malaria; obesity; psychiatric disorders; cancer (e.g., as described herein); inflammation (e.g., inflammatory disease and disorders as described herein); neurodegenerative disorders; and age-related macular degeneration (AMD, e.g., dry or wet form), as described herein.

According to a specific embodiment, the disease includes, without limitation, psoriasis, rheumatoid arthritis, multiple sclerosis, atherosclerosis, glomerulonephritis, epilepsy, Alzheimer's disease, brain ischemia, traumatic brain injury, type II diabetes and AMD.

According to a specific embodiment, a compound according to the present embodiments is for treating age-related macular degeneration (AMD).

According to a specific embodiment, the age-related macular degeneration (AMD) is atrophic, non-neovascular (aAMD).

According to a specific embodiment, the age-related macular degeneration (AMD) is neovascular.

Cancer Treatment:

According to some embodiments, a small molecule compound of Formula Ia and/or Ib, or of Formula IIa and/or IIb, as described herein in any of the respective embodiments, and any combination thereof, is capable of, or is usable, in treating cancer.

According to some embodiments, a small molecule compound of Formula Ia and/or Ib, or of Formula IIa and/or IIb, as described herein in any of the respective embodiments, and any combination thereof, is capable of, or is usable, in inducing death of cancer cells (killing cancer cells).

According to some embodiments, a small molecule compound of Formula Ia and/or Ib, or of Formula IIa and/or IIb, as described herein in any of the respective embodiments, and any combination thereof, is capable of, or is usable, inducing apoptosis in cancer cells.

According to some embodiments, a small molecule compound of Formula Ia and/or Ib, or of Formula IIa and/or IIb, as described herein in any of the respective embodiments, and any combination thereof, is capable of, or is usable, in inducing growth arrest in cancer cells, and in some embodiments, the arrest is at the G2M phase of the cell cycle.

According to an aspect of some embodiments of the present invention, there is provided a method of treating a cancer in a subject in need thereof, the method comprising administering to the subject a therapeutically effective amount of a small molecule compound according to any of the embodiments described herein, thereby treating the cancer.

According to an aspect of some embodiments of the present invention, there is provided a use of a small molecule compound according to any of the embodiments described herein in the manufacture of a medicament for treating cancer.

According to an aspect of some embodiments of the present invention, there is provided a use of a small molecule compound according to any of the embodiments described herein in treating cancer.

As used herein, the terms "cancer" and "tumor" are interchangeably used. The terms refer to a malignant growth and/or tumor caused by abnormal and uncontrolled cell proliferation (cell division). The term "cancer" encompasses tumor methastases. The term "cancer cell" describes the cells forming the malignant growth or tumor.

Non-limiting examples of cancers and/or tumor metastases which can be treated according to some embodiments of any of the embodiments described herein relating to cancer (including any of the aspects described herein) include any solid or non-solid cancer and/or tumor metastasis, including, but not limiting to, tumors of the gastrointestinal tract (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic breast cancer, susceptibility to breast cancer, type 4 breast cancer, breast cancer-1, breast cancer-3, breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B-cell lymphoma, Diffuse large B-cell lymphoma (DLBCL), Burkitt lymphoma, cutaneous T-cell lymphoma, histiocytic lymphoma, lymphoblastic lymphoma, T-cell lymphoma, thymic lymphoma), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B-cell), hypernephroma, insulinoma, islet tumor, keratoma, leiomyoblastoma, leiomyosarcoma, leukemia (e.g., acute lymphatic leukemia, acute lymphoblastic leukemia, acute lymphoblastic pre-B cell leukemia, acute lymphoblastic T cell leukemia, acute megakaryoblastic leukemia, monocytic leukemia, acute myelogenous leukemia, acute myeloid leukemia, acute myeloid leukemia with eosinophilia, B-cell leukemia, basophilic leukemia, chronic myeloid leukemia, chronic B-cell leukemia, eosinophilic leukemia, Friend leukemia, granulocytic or myelocytic leukemia, hairy cell leukemia, lymphocytic leukemia, megakaryoblastic leukemia, monocytic leukemia, monocytic-macrophage leukemia, myeloblastic leukemia, myeloid leukemia, myelomonocytic leukemia, plasma cell leukemia, pre-B cell leukemia, promyelocytic leukemia, subacute leukemia, T-cell leukemia, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme, multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

In some embodiments of any one of the embodiments described herein relating to cancer, the cancer is a leukemia, a lymphoma, an ovarian cancer, a brain cancer (e.g., neuroblastoma), a pancreatic cancer, a prostate cancer, a liver cancer (e.g., hepatocellular carcinoma), colorectal cancer and/or a lung cancer (e.g., a small cell lung cancer).

Examples of leukemias which may be treated in the context of some embodiments of the invention include, without limitation, acute leukemias, for example, acute myeloid leukemia (AML), chronic myeloid leukemia (CML) and acute lymphoblastic leukemia.

Examples of lymphomas which may be treated in the context of some embodiments of the invention include, without limitation, Diffuse large B-cell lymphoma (DLBCL), multiple myeloma and non-Hodgkin's lymphomas. Burkitt lymphoma is a non-limiting example of a non-Hodgkin's lymphoma.

Examples of lung cancers which may be treated in the context of some embodiments of the invention include, without limitation, large cell lung cancer and small cell lung cancer.

In some embodiments of any one of the embodiments described herein relating to cancer, the cancer is a leukemia, and in some embodiments it is AML.

In some embodiments of any one of the embodiments described herein relating to cancer, the cancer is a pancreatic cancer.

In some embodiments of any one of the embodiments described herein relating to cancer, the cancer is characterized by cells expressing CXCR4. In some such embodiments, the compound for use in treating cancer is any one of the compounds described herein as being for use in inhibiting SDF-1 and/or CXCR4 activity.

Without being bound by any particular theory, it is believed that in cancers characterized by expression of CXCR4, the activity of SDF-1 and CXCR4 is generally associated with metastasis, and thus, treatment with an inhibitor of SDF-1 and/or CXCR4 activity is particularly advantageous.

In some embodiments of any one of the embodiments described herein relating to cancer, the cancer is a drug-resistant cancer. In some of these embodiments, the cancer is resistance to an anti-angiogenesis chemotherapeutic agent such as, for example, a taxane (e.g., taxol). In some of these embodiments, the cancer is a multi-drug resistant cancer. The drug resistance of the cancer cells can be an acquired resistance (e.g., a resistance developed upon treatment or repeated treatments) or inherent resistance. In some embodiments of any one of the embodiments described herein relating to cancer, the cancer cells are resistant to taxol. In some of these embodiments, the resistance is inherent.

In some embodiments of any one of the embodiments described herein relating to cancer, the cancer cells are resistant to irinotecan or to any other chemotherapeutic agent of the camptothecin family. In some of these embodiments, the resistance is acquired.

In some embodiments of any one of the embodiments described herein relating to treatment of cancer, the treatment further comprises administering at least one additional anti-cancer agent (i.e., in addition to the compound described hereinabove).

The additional anti-cancer agent may be any agent used in the medical arts to treat a cancer. Examples of anti-cancer agents include, without limitation, acivicin; aclarubicin; acodazole hydrochloride; acronine; adriamycin; Adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; combrestatin A-4 phosphate; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ombrabulin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofuirin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vincristine sulfate; vindesine; vindesine sulfate; vinepidinee; vinglycinate; vinleurosine; vinorelbine tartrate; vinrosidine; vinzolidine; vorozole; zeniplatin; zinostatin; and zorubicin hydrochloride. Additional anti cancer agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division), the contents of which are incorporated herein by reference.

In some embodiments of any of the embodiments described herein, the additional anti-cancer agent is characterized in that resistance of cancer cells to the agent is associated with an activity of SDF-1 and/or CXCR4. In some such embodiments, the compound for use in combination with the additional anti-cancer agent is any one of the compounds described herein.

In some embodiments of any of the embodiments described herein, the at least one additional anti-cancer agent comprises combrestatin A-4 phosphate, ombrabulin and/or any other derivative of combrestatin.

Without being bound by any particular theory, it is believed that the anti-therapeutic effect of combrestatin derivatives such as combrestatin A-4 phosphate and ombrabulin is reduced by SDF-1/CXCR4 activity.

In some embodiments of any of the embodiments described herein, the small molecule compound of the present embodiments and the at least one additional anti-cancer agent act in synergy.

By "act in synergy" it is meant that when both agents are contacted together with cancer cells, the therapeutic activity is higher than the additive activity of each agent alone. In some embodiments, the therapeutic activity is reducing the number of viable cells, and in some embodiments, the therapeutic activity is arresting the growth of the cells, as described herein.

Synergy can be determined by methods known in the art. In some embodiments, synergy is determined by means of an isobologram, as widely described in the art.

When two agents act is synergy, a combination treatment utilizing these agents allows using a lower amount of at least one of these agents. This is particularly useful when treatment with an anti-cancer agent is known to induce acquired resistance thereto.

According to some of any of the embodiments described herein in the context of cancer treatment, there is provided a combination treatment that comprises administering to a subject in need therein a small molecule compound according to the present embodiments and at least one additional anti-cancer agent.

In some of these embodiments, the at least one additional anti-cancer agent is administered in a sub-therapeutic dose, that is, at a dose that is lower than a therapeutically effective amount thereof (e.g., determined as described herein and/or in the art related to this anti-cancer agent).

The two agents can be administered sequentially, in any order, or simultaneously, and can optionally be formulated in the same pharmaceutical composition.

In some of any of the embodiments described herein, the additional anti-cancer agent is irinotecan.

Non-Cancerous Hyperproliferative Diseases:

In some of any of the embodiments described herein, a small molecule compound according to the present embodiments is for use in treating a non-cancerous hyperproliferative disease.

In some of any of the embodiments described herein, there is provided a method of treating a non-cancerous hyperproliferative disease, which comprises administering to a subject in need thereof (a subject afflicted by the disease, a subject that suffers from symptoms associated with the disease, a subject diagnosed as having the disease or a subject suspected as having the disease) a therapeutically effective amount of a small molecule compound as described herein.

In some of any of the embodiments described herein, a small molecule compound according to the present embodiments is for use in manufacturing a medicament for treating a non-cancerous hyperproliferative disease.

Non-cancerous hyperproliferative diseases also referred to "non-neoplastic proliferative diseases" and "non-cancerous proliferative diseases" refer to diseases or disorders which onset or progression is associated with non-malignant cell proliferation. Examples of such medical conditions include, but are not limited to atherosclerosis, rheumatoid arthritis, psoriasis, fibrosis, idiopathic pulmonary fibrosis, scleroderma, stenosis, restenosis, in-stent stenosis and cirrhosis of the live.

Inflammatory Diseases and Disorders:

In some of any of the embodiments described herein, a small molecule compound according to the present embodiments is for use in treating an inflammatory disease or disorder in a subject in need thereof.

In some of any of the embodiments described herein, there is provided a method of treating an inflammatory disease or disorder, which comprises administering to a subject in need thereof (a subject afflicted by the disease, a subject that suffers from symptoms associated with the disease, a subject diagnosed as having the disease or a subject suspected as having the disease) a therapeutically effective amount of a small molecule compound as described herein.

In some of any of the embodiments described herein, a small molecule compound according to the present embodiments is for use in manufacturing a medicament for treating an inflammatory disease or disorder.

Inflammatory diseases and disorders generally encompass diseases and disorders associated with inflammation.

The term "inflammation" as used herein refers to the general term for local accumulation of fluids, plasma proteins, and white blood cells initiated by physical injury, infection, or a local immune response Inflammation may be associated with several signs e.g. redness, pain, heat, swelling and/or loss of function. Inflammation is an aspect of many diseases and disorders, including but not limited to diseases related to immune disorders, viral and bacterial infection, arthritis, autoimmune diseases, collagen diseases, allergy, asthma, pollinosis, and atopy (as described in further detail below).

Thus, inflammation can be triggered by injury, for example injury to skin, muscle, tendons, or nerves Inflammation can be triggered as part of an immune response, e.g., pathologic autoimmune response Inflammation can also be triggered by infection, where pathogen recognition and tissue damage can initiate an inflammatory response at the site of infection.

Inflammation according to the present teachings may be associated with chronic (long term) inflammatory diseases or disorders or acute (short term) inflammatory diseases or disorders.

According to a specific embodiment, the inflammation is associated with a disease selected from the group consisting of an infectious disease, an autoimmune disease, a hypersensitivity associated inflammation, a graft rejection and an injury.

According to a specific embodiment, the inflammation comprises a skin inflammation.

According to a specific embodiment, the skin inflammation is psoriasis.

Diseases characterized by inflammation of the skin, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis, roseacae, psoriasis and acne. Inflammation can also result from physical injury to the skin.

Inflammation may be triggered by various kinds of injuries to muscles, tendons or nerves. Thus, for example, inflammation may be caused by repetitive movement of a part of the body i.e. repetitive strain injury (RSI). Diseases characterized by inflammation triggered by RSI include, but are not limited to, bursitis, carpal tunnel syndrome, Dupuytren's contracture, epicondylitis (e.g. tennis elbow), ganglion (i.e. inflammation in a cyst that has formed in a tendon sheath, usually occurring on the wrist), rotator cuff syndrome, tendinitis (e.g., inflammation of the Achilles tendon), tenosynovitis, and trigger finger (inflammation of the tendon sheaths of fingers or thumb accompanied by tendon swelling).

Many diseases related to infectious diseases include inflammatory responses, where the inflammatory responses are typically part of the innate immune system triggered by the invading pathogen Inflammation can also be triggered by physical (mechanical) injury to cells and tissues resulting from the infection. Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases. According to one embodiment, examples of infections characterized by inflammation include, but are not limited to, encephalitis; meningitis; encephalomyelitis; viral gastroenteritis; viral hepatitis.

Furthermore, many immune disorders include acute or chronic inflammation. For example, arthritis is considered an immune disorder characterized by inflammation of joints, but arthritis is likewise considered an inflammatory disorder characterized by immune attack on joint tissues.

Inflammation according to the present teachings may be associated with a deficient immune response (e.g., HIV, AIDS) or with an overactive immune response (e.g., allergy, autoimmune disorders). Thus, inflammation according to the present teachings may be associated with any of the following:

Inflammatory Diseases Associated with Hypersensitivity:

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to a specific embodiment, the ocular disease is age-related macular degeneration (AMD).

According to a specific embodiment, the age-related macular degeneration (AMD) is atrophic, non-neovascular (aAMD).

According to a specific embodiment, the age-related macular degeneration (AMD) is neovascular.

Autoimmune Diseases:

Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune pro statitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to one embodiment, the autoimmune disease is Crohn's disease, psoriasis, scleroderma or rheumatoid arthritis.

Graft Rejection Diseases:

Examples of diseases associated with transplantation of a graft include, but are not limited to, graft rejection, chronic graft rejection, subacute graft rejection, hyperacute graft rejection, acute graft rejection and graft versus host disease.

Allergic Diseases:

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Additional Applications:

The compounds described herein according to any of the aspects of embodiments of the invention described herein can be utilized for coating medical devices, including implantable medical devices, and particularly medical devices where inhibiting cell migration and/or proliferation is desirable.

Exemplary such medical devices include stents, catheters, endotracheal tubes, tubings, prosthetics, medical implants, artificial joints, artificial valves, needles, intravenous access devices, cannulas, biliary stents, nephrostomy tubes, vascular grafts, infusion pumps, adhesive patches, sutures, meshes, surgical tools or instruments, intubation devices, cardiovascular stents, cardiac surgery devices, orthopedic surgery devices, orthodontic or periodontic devices, dental surgery devices, veterinary surgery devices, bone scaffolds, hemodialysis tubings or equipment, blood exchanging devices, implantable prostheses, heart valves, ophthalmic devices and breast implants.

According to some embodiments of the invention, the medical device is an implantable device, for example, a stent, an indwelling catheter or a tracheal tube.

Catheters include, for example, urinary catheter, central venous catheter, biliary vascular catheter, pulmonary artery catheter, peripheral venous catheter, arterial line, central venous catheter, peritoneal catheter, epidural catheter and central nervous system catheter.

The implantable device can be permanently or transiently implantable device.

Any commercially available or custime-made medical decide, such as implantable devices as described herein, is contemplated.

According to some embodiments of the present invention there is provided a medical device as described herein having a compound as described herein in any of the respective embodiments associated with at least a portion of the medical device. In some embodiments, the compound is deposited on at least a portion of an outer surface of (e.g., coats) the medical device.

The compound can be associated to the device directly, for example, by being included within or absorbed to the material forming the device (e.g., being mixed or absorbed to a polymeric material from which the device is made). Alternatively, or in addition, the compound can be deposited on an outer surface of the device by means of a polymeric film or any other coating material in which the compound is included or absorbed to.

Pharmaceutical Compositions:

The compounds described herein according to any of the aspects of embodiments of the invention described herein can be utilized (e.g., administered to a subject) per se or in a pharmaceutical composition where the compound is mixed with suitable carriers or excipients.

As used herein a "pharmaceutical composition" refers to a preparation of one or a compound according to any of the embodiments described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

When utilized per se or in a pharmaceutically acceptable composition, the compound per se (that is, not including, weight of carriers or excipients co-formulated with the compound, as described herein) is optionally at least 80% pure (by dry weight), optionally at least 90% pure (by dry weight), at least 95% pure (by dry weight), at least 98% pure (by dry weight), and optionally at least 99% pure (by dry weight). Purity may be enhanced, e.g., by removing impurities associated with synthesis of the compound or isolation of the compound from a natural source, by any suitable technique known in the art. Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, breast tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of the active ingredient(s) effective to prevent, alleviate or ameliorate symptoms of a disorder (e.g., cancer or metastatic cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (see, e.g., Fingl et al. (1975), in "The Pharmacological Basis of Therapeutics", Ch. 1 p. 1).

Dosage amount and interval may be adjusted individually to provide protein (e.g., SDF-1 and/or CXCR4) inhibitory levels of the active ingredient are sufficient to induce or suppress the biological effect (minimal effective concentration, MEC). The MEC will vary for each preparation, but can be estimated from in vitro data, e.g., based on results on chemokine-induced (e.g., SDF-1-induced) migration inhibition assay described herein. Dosages necessary to achieve the MEC will depend on individual characteristics and route of administration. Detection assays can be used to determine plasma concentrations.

In some embodiments of any of the embodiments described herein, an effective amount of the compound is less than 100 µM. In some embodiments, an effective amount is less than 10 µM. In some embodiments, an effective amount is less than 5 µM. In some embodiments, an effective amount is less than 1 µM. In some embodiments, an effective amount is less than 0.5 µM. In some embodiments, an effective amount is less than 0.1 µM.

In some embodiments of any of the embodiments described herein, an effective amount is at least 100% of the IC50 of the compound towards a chemokine which is intended to be inhibited (e.g., SDF-1). In some embodiments, an effective amount is at least 200% of the IC50 of the compound towards the chemokine. In some embodiments, an effective amount is at least 300% of the IC50 of the compound towards the chemokine. In some embodiments, an effective amount is at least 500% of the IC50 of the compound towards the chemokine. In some embodiments, an effective amount is at least 1000% of the IC50 of the compound towards the chemokine.

In some embodiments of any of the embodiments described herein, an effective amount is at least 100% of the IC50 of the compound towards inducing cell death of cancer cells to be inhibited. In some embodiments, an effective amount is at least 200% of the IC50 of the compound towards the cancer cells. In some embodiments, an effective amount is at least 300% of the IC50 of the compound towards the cancer cells.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed herein.

It will be appreciated that the compounds described herein can be provided alone or in combination with other active ingredients, which are well known in the art for alleviating the medical condition.

Thus, for example, the compound may be administered with an immunomodulator, either together in a co-formulation or in separate formulations.

According to a specific embodiment, the treatment of cancer (and other hyperproliferative disorders) is effected in combination with an anti-cancer immune modulator agent.

As used herein, the term "anti-cancer immune modulator agent" refers to an agent capable of eliciting an immune response (e.g. T cell, NK cell) against a cancerous cell.

According to specific embodiment, the agent is selected from the group consisting of a cancer antigen, a cancer vaccine, an anti-cancer antibody, a cytokine capable of inducing activation and/or proliferation of a T cell and an immune-check point regulator.

Alternatively or additionally, such modulators may be immune stimulators such as immune-check point regulators which are of specific value in the treatment of cancer.

As used herein the term "immune-check point regulator" refers to a molecule that modulates the activity of one or more immune-check point proteins in an agonistic or antagonistic manner resulting in activation of an immune cell.

As used herein the term "immune-check point protein" refers to a protein that regulates an immune cell activation or function. Immune check-point proteins can be either co-stimulatory proteins (i.e. transmitting a stimulatory signal resulting in activation of an immune cell) or inhibitory proteins (i.e. transmitting an inhibitory signal resulting in suppressing activity of an immune cell). According to specific embodiment, the immune check point protein regulates activation or function of a T cell. Numerous checkpoint proteins are known in the art and include, but not limited to, PD1, PDL-1, B7H2, B7H4, CTLA-4, CD80, CD86, LAG-3, TIM-3, KIR, IDO, CD19, OX40, 4-1BB (CD137), CD27, CD70, CD40, GITR, CD28 and ICOS (CD278).

According to specific embodiments, the immune-checkpoint regulator is selected form the group consisting of anti-CTLA4, anti-PD-1, and CD40 agonist.

According to specific embodiments, the immune-check point regulator is selected form the group consisting of anti-CTLA4, anti-PD-1, anti-PDL-1, CD40 agonist, 4-1BB agonist, GITR agonist and OX40 agonist.

CTLA4 is a member of the immunoglobulin superfamily, which is expressed on the surface of Helper T cells and transmits an inhibitory signal to T cells upon ligand binding. As used herein, the term "anti-CTLA4" refers to an antagonistic molecule that binds CTLA4 (CD152) and suppresses its suppressive activity. Thus, an anti-CTLA4 prevents the transmission of the inhibitory signal and thereby acts as a co-stimulatory molecule. According to a specific embodiment, the anti-CDLA4 molecule is an antibody.

PD-1 (Programmed Death 1) is a member of the extended CD28/CTLA-4 family of T cell regulators which is expressed on the surface of activated T cells, B cells, and macrophages and transmits an inhibitory signal upon ligand binding. As used herein, the term "anti-PD1" refers to an antagonistic molecule that binds PD-1 and suppresses it's suppressive activity. Thus, an anti-PD-1 prevents the transmission of the inhibitory signal and thereby acts as a co-stimulatory molecule. According to a specific embodiment, the anti-PD1 molecule is an antibody. Numerous anti-PD-1 antibodies are known in the art see e.g. Topalian, et al. NEJM 2012.

PDL-1 is a ligand of PD-1. Binding of PDL-1 to its receptor PD-1 transmits an inhibitory signal to the cell expressing the PD-1. As used herein, the tem "anti-PDL-1" refers to an antagonistic molecule that inhibits PD-1 signaling by binding to or inhibiting PD-L1 from binding and/or activating PD-1. Thus, an anti-PD-1 prevents the transmission of the inhibitory signal and thereby acts as a co-stimulatory molecule. According to specific embodiments, the anti-PD-L1 is an anti-PD-L1 antibody. Numerous anti-PDL-1 antibodies are known in the art see e.g. Brahmer, et al. NEJM 2012.

CD40 (CD154) is a co-stimulatory receptor found on antigen presenting cells and transmits an activation signal upon ligand binding. As used herein, the term "CD40 agonist" refers to an agonistic molecule that binds CD40 (CD154) and thereby induces activation of the antigen presenting cell.

OX40 belongs to the TNF receptor super family and leads to expansion of CD4+ and CD8+ T cells. As used herein, the term "OX40 agonist" refers to an agonistic molecule that binds and activates OX40.

GITR (glucocorticoid-induced tumor necrosis factor receptor) is a surface receptor molecule that has been shown to be involved in inhibiting the suppressive activity of T-regulatory cells and extending the survival of T-effector cells. As used herein, the term "GITR agonist" refers to an agonistic molecule that binds and activates GITR. According to a specific embodiment, the GITR agonist is an antibody.

The compound may be administered with an additional anti-cancer agent, as described herein in any of the respective embodiments, either together in a co-formulation (e.g., in the same pharmaceutical composition) or in separate formulations.

According to a specific embodiment, the treatment of cancer (and other hyperproliferative disorders) is effected in combination with an additional anti-cancer as described herein in any of the respective embodiments.

A pharmaceutical composition as described herein can further comprise any of the additional agents as described herein, or alternatively, be identified for use in combination with any of the additional agents as described herein.

According to another aspect described herein, there is provided a kit for the treatment of a condition (e.g., treatment of cancer or prevention of tumor metastasis or treatment of non-cancerous proliferative disease or disorder or treatment of inflammation) described herein, the kit comprising a packaging material packaging the compound described herein.

In some of these embodiments, the kit further comprises an additional agent as described herein in any of the respective embodiments, and the two agents are packaged individually within the kit.

In some of these embodiments, the kit further comprises instructions to use the compound in combination with an additional agent (e.g., an additional anti-cancer cancer) as described herein in any of the respective embodiments.

In some embodiments, the compound is identified as an inhibitor of an SDF-1 and/or CXCR4 activity associated with an onset or progression of the condition, as described herein.

In some embodiments, the compound is identified as inducing apoptosis and/or cell growth arrest of cells associated with the condition, as described herein.

According to an aspect of some embodiments of the present invention there is provided a pharmaceutical composition comprising a small molecule compound as described herein in any of the respective embodiments, optionally in combination with a pharmaceutically acceptable carrier, and further optionally in combination with additional active as described herein in the respective embodiments.

According to an aspect of some embodiments of the present invention there is provided a small molecule compound as described herein in any of the respective embodiments for use as a medicament or in the manufacture of a medicament.

The medicament can be a pharmaceutical composition as described herein in any of the respective embodiments.

The medicament can be for use in treating any of the medical conditions, diseases and/or disorders as described herein.

Definitions

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. For example, in the context of preventing metastasis and/or angiogenesis, the term "preventing" refers to arresting, halting, inhibiting the metastatic and/or angiogenetic process or progression and subsequent metastasis and/or angiogenesis.

As used herein the term "subject" refers to a mammal (e.g., human), for example, one who has been diagnosed with a condition described herein (e.g., cancer).

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the phrase "linking group" describes a group (a substituent) that is attached to another moiety in the compound via two or more atoms thereof. In order to differentiate a linking group from a substituent that is attached to another moiety in the compound via one atom thereof, the latter will be referred to herein and throughout as an "end group".

As used herein, the term "amine" describes both a —NR'R" end group and a —NR'— linking group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is or forms a part of a linking group.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. Unless otherwise indicated, the alkyl is a lower alkyl having 1 to 4 carbon atoms. In some embodiments, the alkyl has at least 4 carbon atoms, for example, the alkyl is having 4 to 12 or 4 to 10 or 4 to 8 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, oxo, carbonyl, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When an alkyl is a linking group, it is also referred to herein as "alkylene", e.g., methylene, ethylene, propylene, etc.

The term "alkenyl" describes an alkyl, as defined herein, in which at least one pair of carbon atoms are linked to one another via a double bond.

The term "alkynyl" or "alkyne" describes an alkyl, as defined herein, in which at least one pair of carbon atoms are linked to one another via a triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, oxo, carbonyl, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, oxo, carbonyl, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof. Preferably, the aryl is phenyl. Optionally, the aryl is naphthalenyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, triazine, tetrazine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof.

The term "alkaryl" describes an alkyl, as defined herein, which is substituted by one or more aryl or heteroaryl groups. An example of alkaryl is benzyl.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" or "sulfinyl" describes a —S(=O)—OR' end group or an —S(=O) O— group linking group, as these phrases are defined hereinabove, where R' is as defined hereinabove.

The term "sulfoxide" describes a —S(=O)R' end group or an —S(=O)— linking group, as these phrases are defined hereinabove, where R' is as defined hereinabove.

The term "sulfonate" or "sulfonyl" describes a —S(=O)$_2$—OR' end group (also referred to herein as —SO$_3$R' or —SO$_3$H) or an —O—S(=O)$_2$— linking group, as these phrases are defined hereinabove, where R' is as defined herein.

The term "S-sulfonamide" describes a —S(=O)$_2$—NR'R" end group or a —S(=O)$_2$—NR'-linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "carbonyl" or "carbonate" or "ketone" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, described a =O end group.

The term "thiooxo" as used herein, described a =S end group.

The term "oxime" describes a =N—OH end group or a =N—O— linking group, as these phrases are defined hereinabove.

The term "hydroxyl" or "hydroxy" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thio" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" or "nitrile" describes a —CN group.

The term "isocyanate" describes an —N=C=O group.

The term "nitro" describes an —NO$_2$ group.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "dithiocarbamate" as used herein encompasses N-dithiocarbamate and S-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR" linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR" linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

For any of the embodiments described herein, the compound described herein may be in a form of a salt thereof, for example, a pharmaceutically acceptable salt thereof, and/or in a form of a prodrug thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be a base addition salt comprising at least one acidic (e.g., phenol and/or carboxylic acid) group of the compound which is in a negatively charged form (e.g., wherein the acidic group is deprotonated), in combination with at least one counter-ion, derived from the selected base, that forms a pharmaceutically acceptable salt.

The base addition salts of the compounds described herein may therefore be complexes formed between one or more acidic groups of the drug and one or more equivalents of a base.

The base addition salts may include a variety of organic and inorganic counter-ions and bases, such as, but not limited to, sodium (e.g., by addition of NaOH), potassium (e.g., by addition of KOH), calcium (e.g., by addition of $Ca(OH)_2$, magnesium (e.g., by addition of $Mg(OH)_2$), aluminum (e.g., by addition of $Al(OH)_3$ and ammonium (e.g., by addition of ammonia). Each of these acid addition salts can be either a mono-addition salt or a poly-addition salt, as these terms are defined herein.

In the context of some of the present embodiments, a pharmaceutically acceptable salt of the compounds described herein may optionally be an acid addition salt comprising at least one base group (e.g., amine or amide group) of the compound which is in a positively charged form (e.g., wherein an —NH— group is protonated), in combination with at least one counter-ion, derived from the selected acid, that forms a pharmaceutically acceptable salt.

The acid addition salts of the compounds described herein may therefore be complexes formed between one or more basic groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

Depending on the stoichiometric proportions between the charged group(s) in the compound and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound (e.g., the compound of the formula described hereinabove). A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally ($C_{1-4}$)acyl (e.g., acetyl) group to form an ester group, and/or any one or more of the carboxylic acid groups of the compound is modified by an alkoxy or aryloxy group, optionally ($C_{1-4}$)alkoxy (e.g., methyl, ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The compounds described herein can be used as polymorphs and the present embodiments further encompass any isomorph of the compounds and any combination thereof.

The present embodiments further encompass any enantiomers and diastereomers of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

Herein throughout, the term "about" describes ±10% or ±5%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Chemical Syntheses

An exemplary compound according to the present embodiments, denoted BKT300-N1 was prepared as depicted in FIG. 1 and as described in the following.

The chemical structure of BKT300-N1 can be presented as two tautomers:

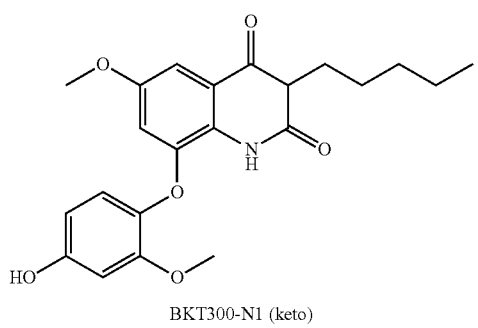

BKT300-N1 (keto)

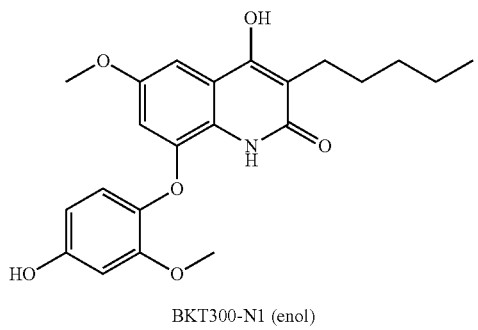

BKT300-N1 (enol)

The chemical name of keto tautomer is 8-(4-hydroxy-2-methoxyphenoxy)-6-methoxy-3-pentylquinoline-2,4(1H,3H)-dione.

The chemical name of the enol tautomer is 4-hydroxy-8-(4-hydroxy-2-methoxyphenoxy)-6-methoxy-3-pentylquinolin-2(1H)-one.

For simplicity, in the following, only the enol tautomer is referred to. However, it is to be noted that the two tautomers can be present, depending on the environmental conditions, either in equilibrium, or as one of the tautomers.

Preparation of
4-(benzyloxy)-2-methoxybenzaldehyde (S2)

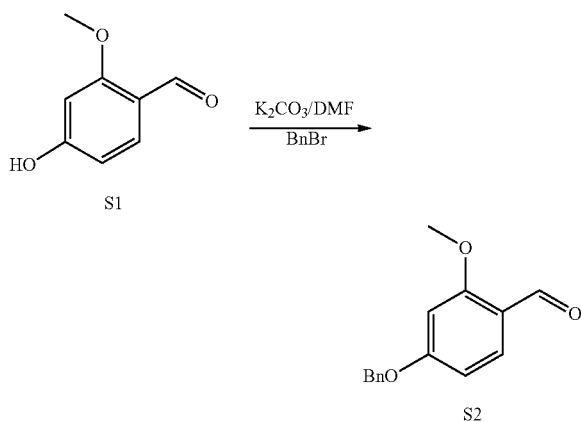

To a solution of 4-hydroxy-2-methoxybenzaldehyde (S1) (150.0 grams, 985 mmol) in DMF (1.0 L) was added $K_2CO_3$ (272 grams, 1970 mmol, 1.5 equivalents) at 0° C. and the obtained mixture was stirred for 30 minutes. BnBr (270 grams, 1576 mmol, 1.6 equivalents) was added into the reaction mixture at 0° C. The reaction mixture was allowed to reach room temperature and stirred overnight. TLC showed the reaction was complete. The reaction mixture was quenched with saturated $NH_4Cl$ and extracted with ethyl acetate (EA) (800 mL×3). The organic layer was washed with water (1000 mL×2) and brine (800 mL), dried over $Na_2SO_4$, filtered and concentrated to give a residue. The residue was purified by column to give the product 4-(benzyloxy)-2-methoxybenzaldehyde (S2) as a colorless oil (215.0 grams, 90% yield).

Preparation of
4-methoxy-3-(trifluoromethoxy)phenol (S3)

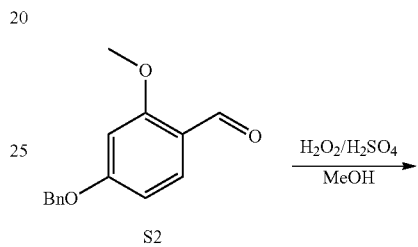

To a suspension of 4-(benzyloxy)-2-methoxybenzaldehyde (S2) (200.0 grams, 825 mmol) and $H_2O_2$ (150 mL, 4412 mmol, 5 equivalents) in MeOH (1250 mL) was added $H_2SO_4$ (15.0 mL, 248 mmol). The reaction mixture was stirred at room temperature overnight. TLC showed the reaction was complete. The reaction mixture was diluted with water (1000 mL) and extracted with EA (500 mL×3). The combined organic layer was washed with brine, dried over $Na_2SO_4$, filtered and concentrated to give a residue. The residue was purified by column to give the product 4-methoxy-3-(trifluoromethoxy)phenol (S3) as a colorless oil (136.8 grams, 72% yield).

Preparation of 4-(benzyloxy)-2-methoxy-1-(5-methoxy-2-nitrophenoxy) benzene (2)

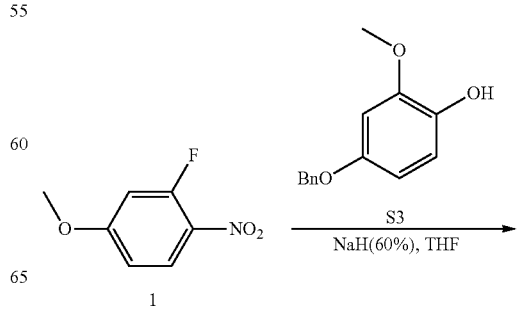

-continued

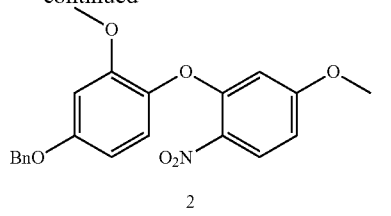

2

To a solution of 4-(benzyloxy)-2-methoxyphenol (S3) (125 grams, 540 mmol) in THF (2.0 L) was added NaH (60%) (23.8 grams, 594 mmol) as portions. The reaction mixture was stirred at 0° C. for 30 minutes. Then 2-fluoro-4-methoxy-1-nitrobenzene (1) (93.0 grams, 540 mmol) was added at 0° C. The reaction mixture was stirred at room temperature overnight. TLC showed the reaction was completed (using Petrol ether (PE):ethyl acetate 10:1 as eluent). The reaction mixture was poured into ice-water and extracted with EA (800 mL×3). The organic layer was washed with brine (500 mL×2), dried over anhydrous Na$_2$SO$_4$, and filtered. The filtrate was concentrated in vacuum. The crude product was purified by silica gel chromatography eluted with PE:EA 10:1 to give the product 2 as a brown oil (155.0 grams, 72% yield).

LC-MS: m/z=382.1 (M$^+$+H)

Preparation of 2-(4-(benzyloxy)-2-methoxyphenoxy)-4-methoxyaniline (3)

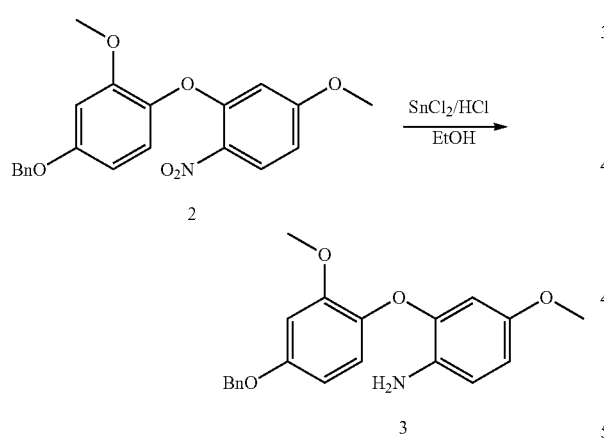

To a mixture of 4-(benzyloxy)-2-methoxy-1-(5-methoxy-2-nitrophenoxy) benzene (2) (155 grams, 275 mmol) and SnCl$_2$·2H$_2$O (372 grams, 1655 mmol, 6.0 equivalents) in EtOH (900 mL) was added HCl (850 mL, 6N). The reaction mixture was heated to reflux and stirred at reflux overnight. LC-MS showed the reaction was completed (using PE:EA 2:1 as eluent). The reaction mixture was diluted with water (1000 mL) and washed with saturated Na$_2$CO$_3$, filtered and the filtrate was extracted with EA (600 mL×3). The combined organic layer was washed with brine, dried over anhydrous Na$_2$SO$_4$, and filtered. The filtrate was concentrated in vacuum to give a residue. The residue was purified by silica gel chromatography eluted with (PE:EA 4:1) to give the product 3 as a black oil (100.0 grams, 83% yield).

LC-MS: m/z 352.4 (M$^+$+H)

Preparation of ethyl 2-((2-(4-(benzyloxy)-2-methoxyphenoxy)-4-methoxyphenyl)carbamoyl)heptanoate (4)

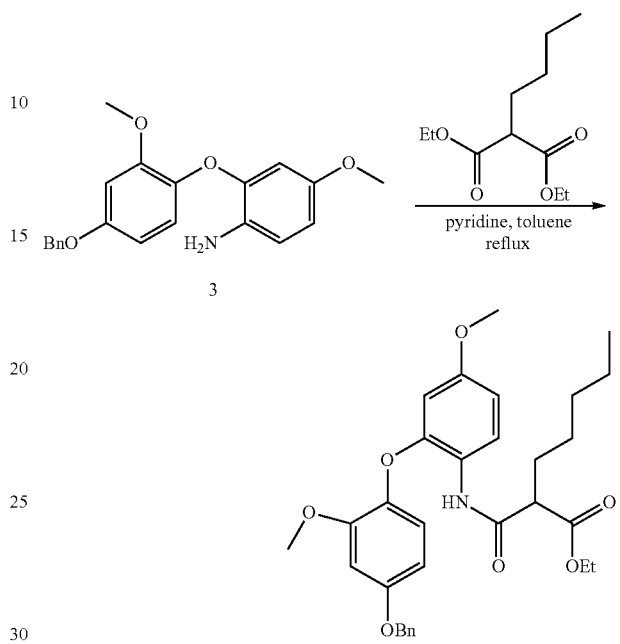

A mixture of 2-(4-(benzyloxy)-2-methoxyphenoxy)-4-methoxyaniline (3) (100 grams, 285 mmol), diethyl 2-pentylmalonate (SM-1) (39 grams, 855 mmol, 3.0 equivalents) and pyridine (45.0 mL, 575 mmol, 2.0 equivalents) in toluene (300 mL) was stirred at reflux for 72 hours. LC-MS showed the reaction was completed. The reaction mixture was concentrated in vacuum. The residue was purified by silica gel chromatography eluted with (PE:EA 7:1) to give the product 4 as a brown oil (100 grams, 67% yield).

LC-MS: m/z 536.3 (M$^+$+H)

Preparation of 2-((2-(4-(benzyloxy)-2-methoxyphenoxy)-4-methoxy phenyl)carbamoyl)heptanoic Acid (5)

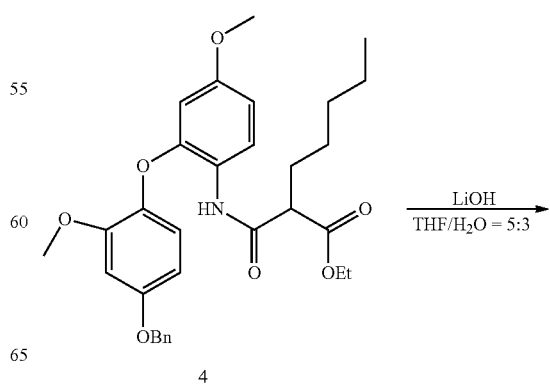

-continued

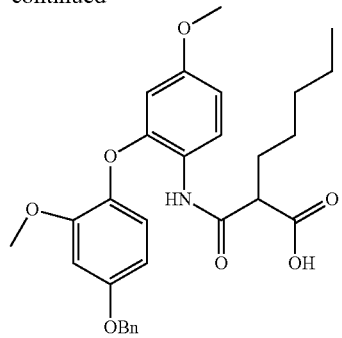

5

To a solution of ethyl 2-((2-(4-(benzyloxy)-2-methoxyphenoxy)-4-methoxyphenyl)carbamoyl)heptanoate (4) (100 grams, 187 mmol) in a mixture solution of THF (500 mL) and H₂O (300 mL) was added LiOH (22 grams, 920 mmol, 5.0 equivalents). The reaction was stirred at room temperature for overnight. TLC showed the reaction was completed. The reaction mixture was concentrated in vacuum. The residue was dissolved in H₂O (300 mL) and acidified to PH 2-3 using concentrated HCL. The reaction mixture was extracted with EA (500 mL×3). The organic layer was washed with brine (500 mL), dried over anhydrous Na₂SO₄, and filtered. The filtrate was concentrated in vacuum to give the product 5 as a brown oil (90 grams, 96% yield).

Preparation of 8-(4-(benzyloxy)-2-methoxyphenoxy)-4-hydroxy-6-methoxy-3-pentylquinolin-2(1H)-one (6)

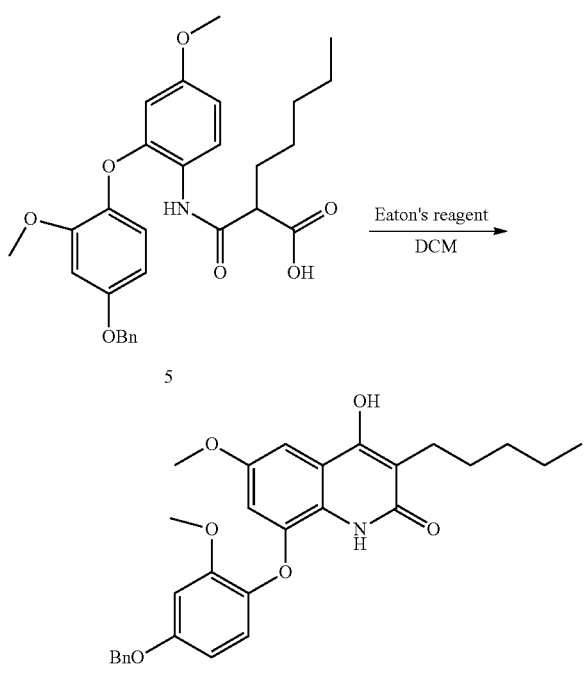

2-((2-(4-(benzyloxy)-2-methoxyphenoxy)-4-methoxyphenyl)carbamoyl) heptanoic acid (5) (30 grams, 59.1 mmol) was added into the solution of Eaton's reagent (42 grams, 177.3 mmol, 3.0 equivalents) in DCM (300 mL). The reaction mixture was stirred at 40° C. for 2 hours. LC-MS showed compound 5 was consumed completely. The reaction mixture was poured into H₂O (50 mL) and washed with saturated NaHCO₃, and extracted with EA (100 mL×3). The organic layer was washed with brine (100 mL), dried over anhydrous Na₂SO₄, and filtered. The filtrate was concentrated in vacuum. The residue was purified by column to give product 6 as a light yellow solid (10.1 grams, 35.1% yield).

Preparation of 4-hydroxy-8-(4-hydroxy-2-methoxyphenoxy)-6-methoxy-3-pentylquinolin-2(1H)-one (BKT300-N1)

2-((2-(4-(benzyloxy)-2-methoxyphenoxy)-4-methoxyphenyl)carbamoyl) heptanoic acid (6) (30 grams, 59.1 mmol) was added into the solution of trifluoroacetic acid (150 mL) and stirred at room temperature for 12 hours. LC-MS showed compound 6 was consumed completely. The solution of TFA was removed at 30° C. under vacuum. The residue was diluted with H₂O (250 mL) and extracted with EA (300 mL×3). The combined organic layers were washed with brine (500 mL), dried over anhydrous Na₂SO₄, and filtered. The filtrate was concentrated in vacuum. The residue was purified by column to give the final product BKT300-N1 as a white solid (10.5 grams, 44.7% yield).

¹H NMR (400 MHz, DMSO): δ (ppm)=10.26 (s, 1H), 9.97 (s, 1H), 9.53 (s, 1H), 7.02 (s, 1H), 6.96 (m, 1H), 6.57 (s, 1H), 6.38 (m, 1H), 6.12 (s, 1H), 3.69 (s, 3H), 3.68 (s, 3H), 2.56 (m, 2H), 1.45 (m, 2H), 1.28 (s, 4H), 0.87 (t, 3H).

HPLC purity: 97.8% (254 nm), 97.7% (214 nm)

MS m/z (ESI): m/z=400.1 (M⁺+H).

Using the outline of the above procedure, other compounds of Formula Ia and/or Ib, or IIa and/or IIb can be synthesized, by selecting the respective compounds corresponding to compound S3, 1 and SM-1 as shown herein and in FIG. 1.

Example 2

In Vitro Migration and Invasion Assays

Migration Assay:

600 μl of RPMI medium containing 1% fetal calf serum (FCS) was added to the lower chambers of Transwell® transmigration plates, supplemented with 100 ng/ml of SDF-1. BKT300-N1 was added to the lower chambers at the indicated concentration, except in control samples. The SDF-1 was incubated with BKT300-N1 for 30 minutes at room temperature before the initiation of the migration assay. Following 30 minutes of incubation $2\times10^5$ Jurkat cells were added to the upper chambers of the transmigration plates in a total volume of 100 μl. Cells which migrated within 3 hours to the bottom chamber of the Transwell® plates were counted using a FACScalibur™ flow cytometer.

Figure 2:
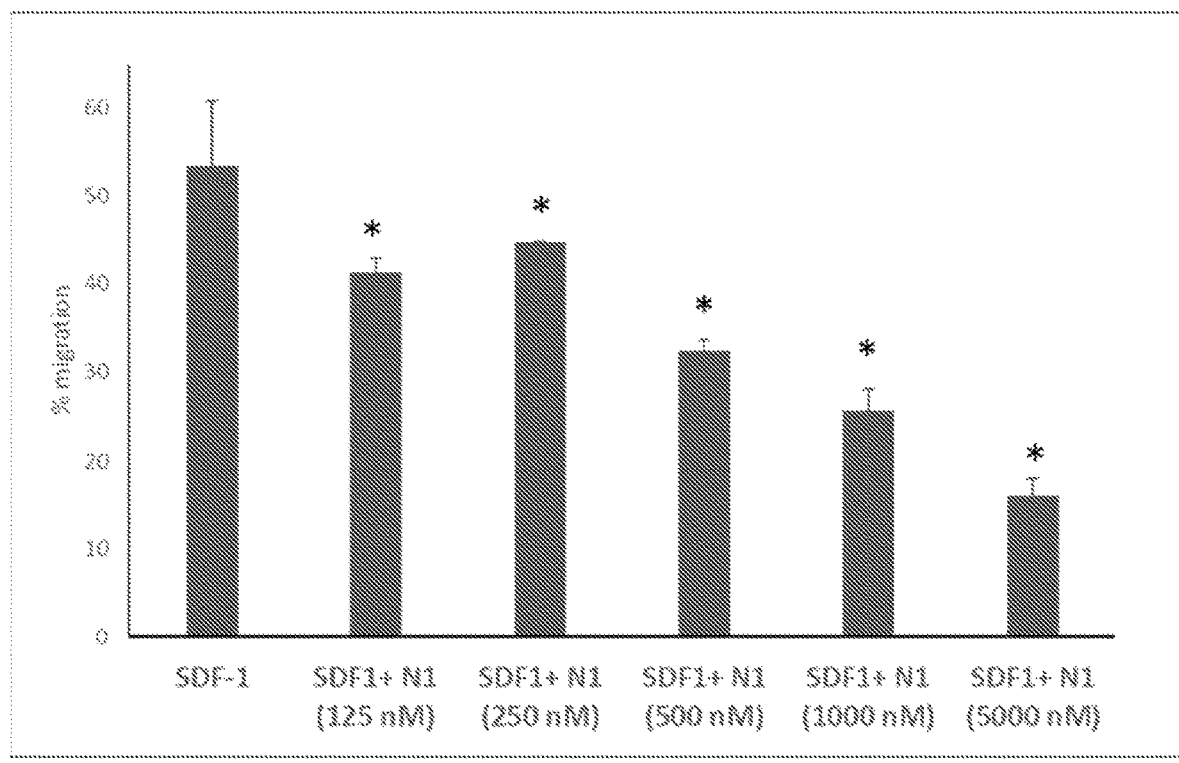
FIG. 2 is a bar graph showing the effect of various concentrations BKT300-N1 on migration of Jurkat AML cells towards SDF-1 (* indicates $p<0.05$ vs. zero concentration).

The results are presented in FIG. 2 and show that BKT300-N1, at a concentration of 0.5 μM, 1 μM, or 5 μM, significantly inhibited the migration of lymphocytic Jurkat cells towards SDF-1.

These results indicate that BKT300-N1 is an effective inhibitor of SDF-1 function, and suggest that this compound is effective for treating conditions associated with activity of SDF-1 and CXCR4 (the receptor of SDF-1).

Scratch Assays:

Scratch assay was performed to assess the effects of BKT300-N1 compared to that of BKT300-3-05 on cell invasion and migration. This system measures scratch closure in real time and automatically calculates the relative wound density and wound width within the initially-vacant area at each time point. The relative wound density is the ratio of the occupied area to the total area of the initial scratched region.

Cells were plated on 96-well Image-lock plates (Essen Bioscience) and grown overnight to form a spatially uniform monolayer.

Scratches were made by using a 96-pin tool Wound-Maker™ (Essen BioScience) to create uniform, reproducible scratches in all the wells of a 96-well plate. After creating the scratch, the medium was aspirated and the wells are washed twice with fresh medium to remove any cells from the scratched area. Following the washes, fresh medium containing different concentrations of the tested compound was added to the wells. Once the fresh medium is added, the plate was placed into the IncuCyte ZOOM™ apparatus and images of the collective cell spreading are recorded every 4 hours for a total duration of 60 hours.

Data processing and analysis were done using the IncuCyte S3 Live-cells Analysis System.

The scratch assay was performed using HCC SNU449 cells. The cells were scratched and incubated with 0.05, 0.1, 0.5, 1 and 10 μM of BKT300-N1 or BKT300-3-05.

Figure 3:
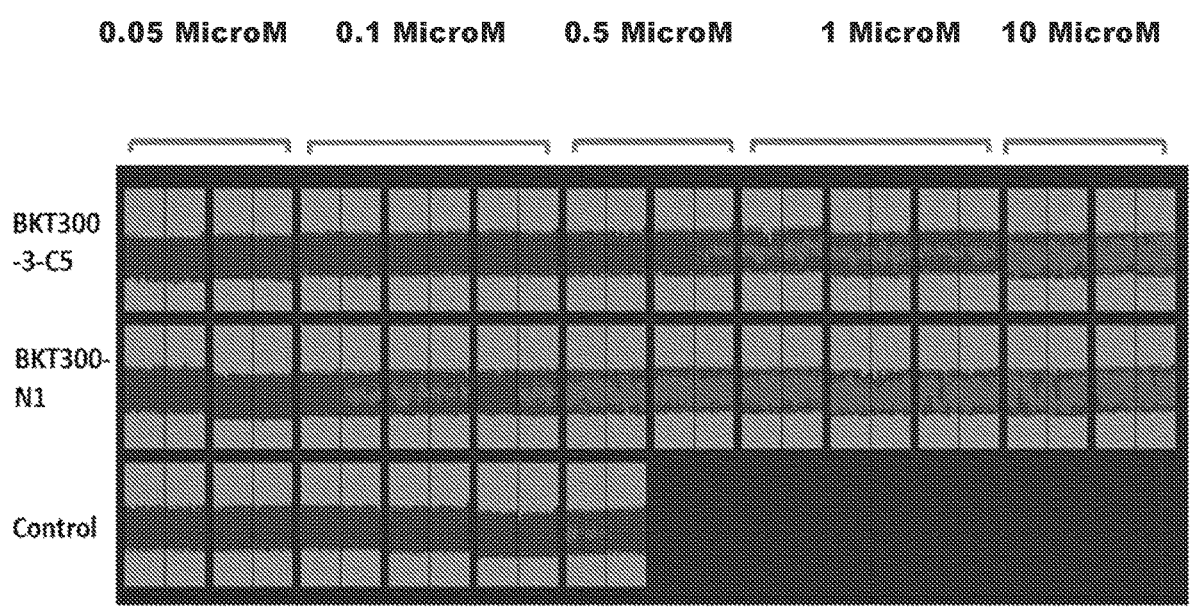
FIG. 3 presents images demonstrating the effect of various concentrations of BKT300-N1 and BKT300-3-05 on the migration of HCC SNU449 cells using the scratch assay, compared to control. SNU449 cells were scratched and incubated with 0.05, 0.1, 0.5, 1 and 10 μM (microM) of BKT300-N1 or BKT300-3-05. Shown are the relative wound areas after 24-hour incubation.
Figure 4A:
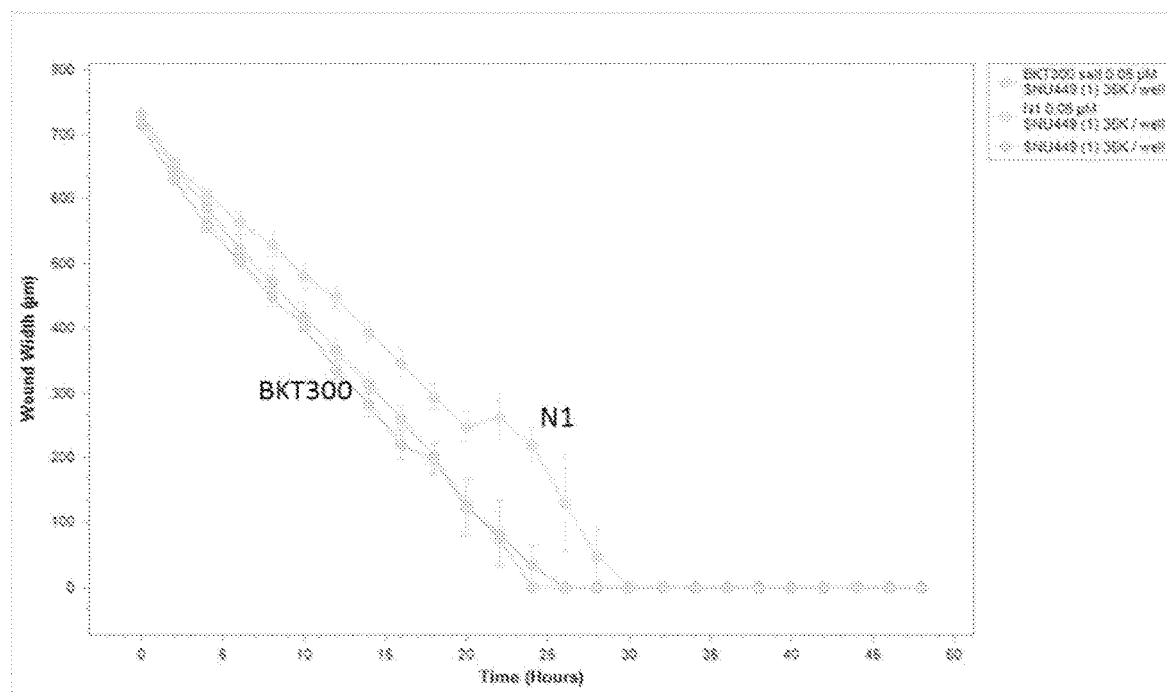
FIGS. 4A-4E present comparative plots showing the effect of BKT300-N1 (denoted for simplicity as N1) and BKT300-3-05 (denoted for simplicity as BKT300), at a concentration of 0.05 μM (microM) (FIG. 4A), 0.1 μM (microM) (FIG. 4B), 0.5 μM (microM) (FIG. 4C), 1 μM (microM) (FIG. 4D) and 10 μM (microM) (FIG. 4E), on the relative wound width values (microns; μm) as analyzed by IncuCyte.
Figure 4B:
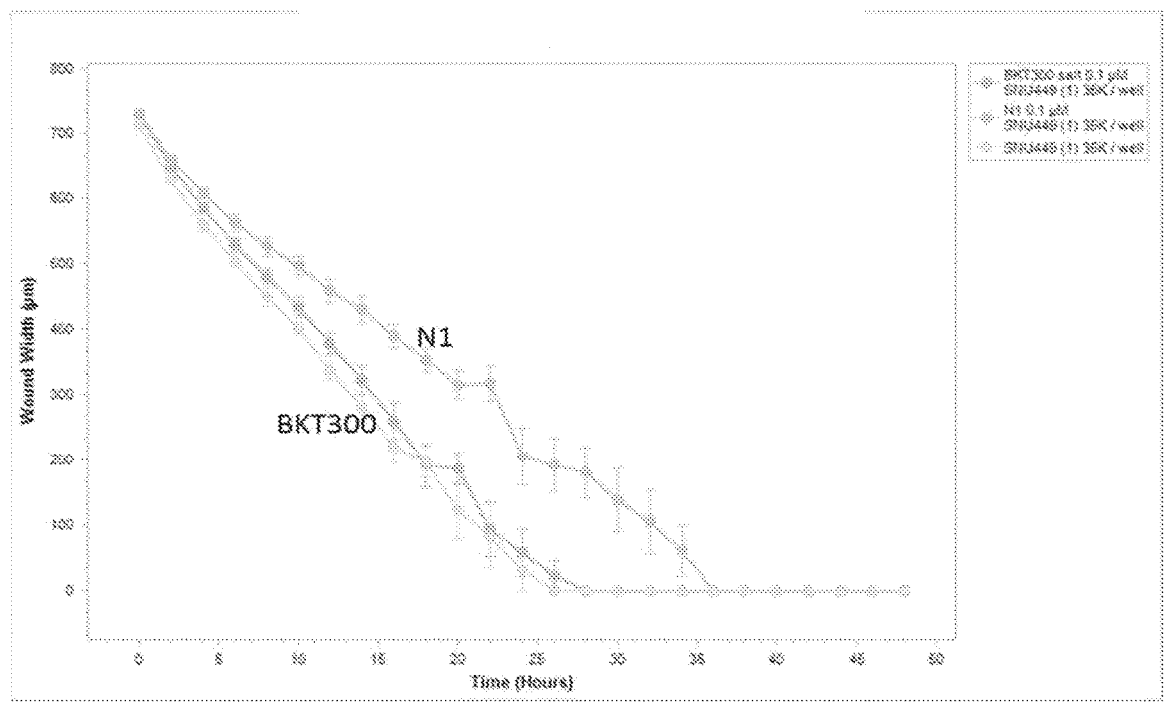
Figure 4C:
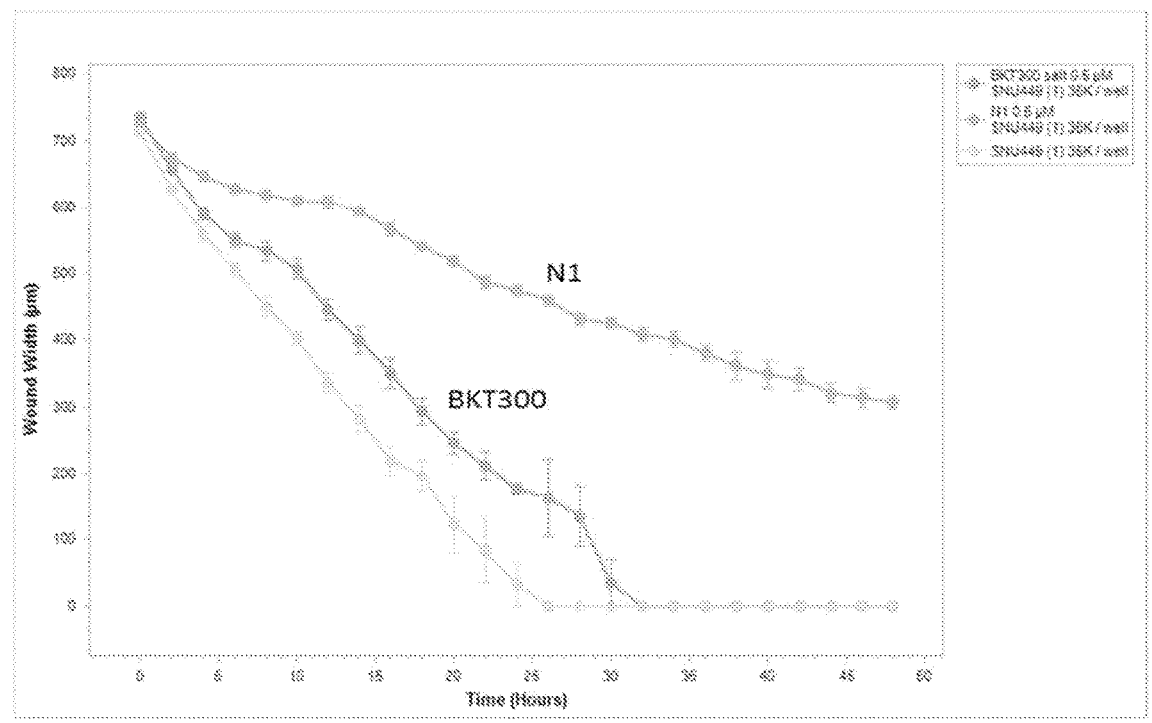
Figure 4D:
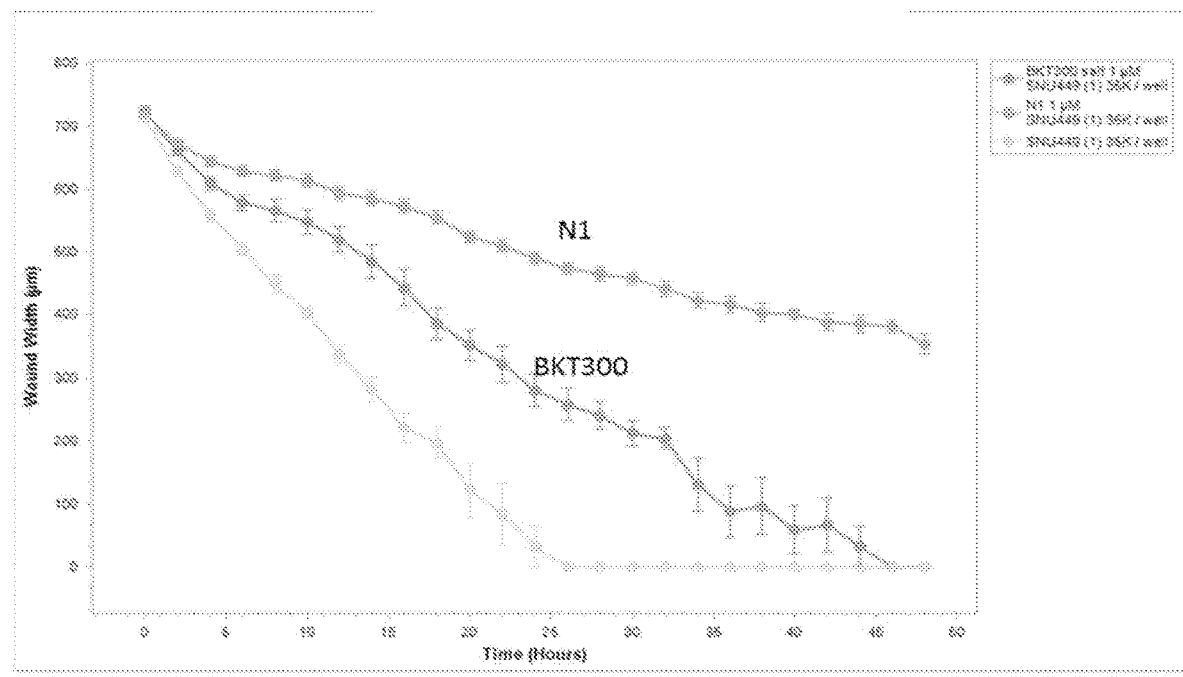
Figure 4E:
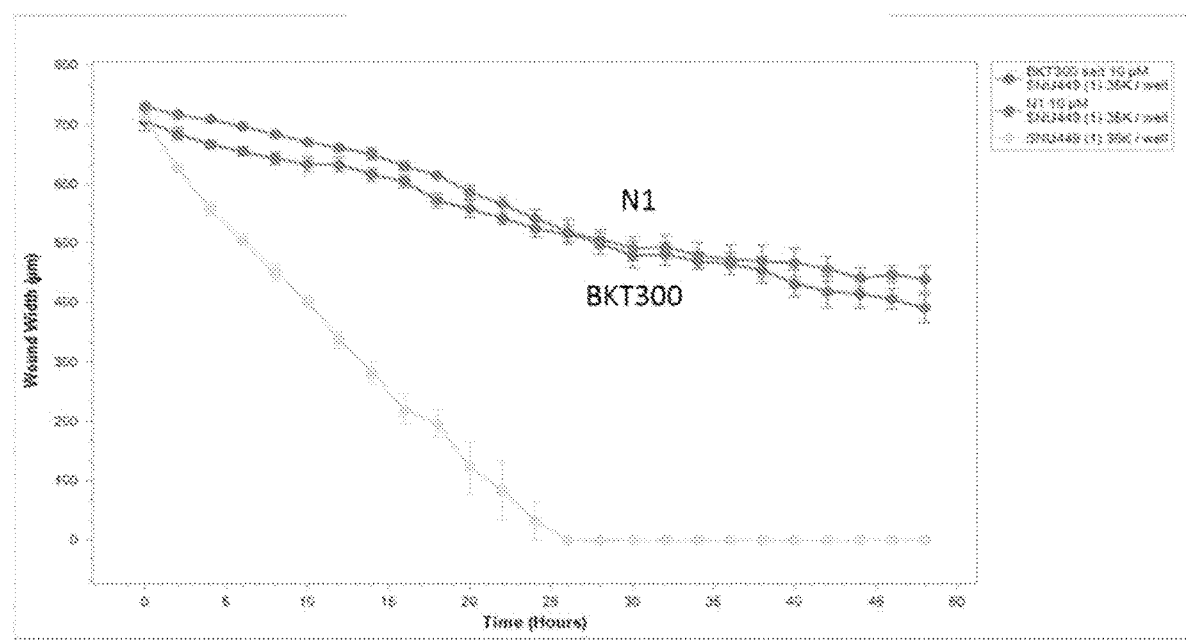

FIG. 3 presents the relative wound area at 24 hours and demonstrates the improved effect of BKT300-N1 already at a concentration of 0.1 μM.

FIGS. 4A-4E present comparative plots showing the wound width values (microns) as analyzed by IncuCyte upon incubation with 0.05, 0.1, 0.5, 1 and 10 μM of BKT300-N1 (denoted, for simplicity, as N1), and upon incubation with 0.05, 0.1, 0.5, 1 and 10 μM of BKT300-3-05 (denoted, for simplicity, as BKT300), respectively, and compared to control, further demonstrating the improved effect of BKT300-N1 over BKT300-3-05, particularly at the lower concentrations.

In another scratch assay, MSTO cells were scratched and incubated with 0.5 μM, 0.1 μM, 0.05 μM, 10 nM, 5 nM, 1 nM and 0.5 nM of BKT300-N1.

Figure 5A:
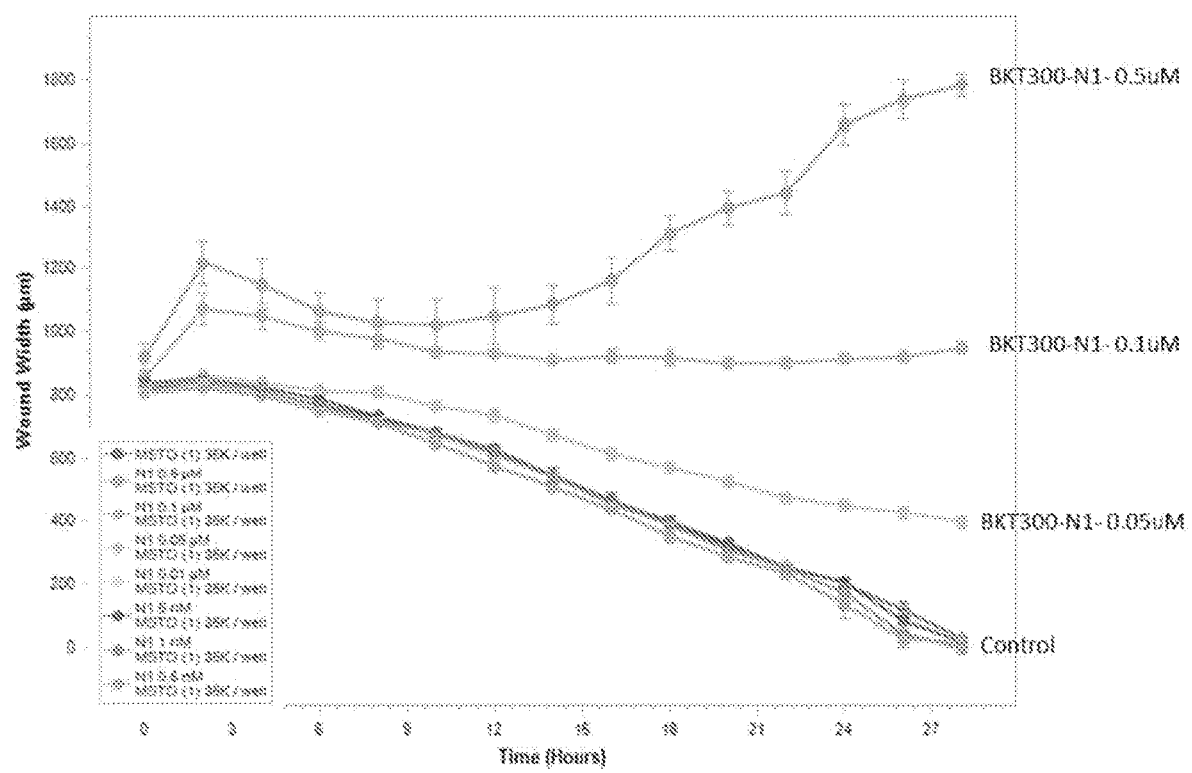
FIGS. 5A-5B present comparative plots demonstrating the effect of various concentrations of BKT300-N1 on migration of MSTO cells using the scratch assay, by showing the relative wound width values (microns) as analyzed by IncuCyte (FIG. 5A), and wound width images obtained with the IncuCyte live-cell imaging system at 48 hours for control, and for BKT300-N1 at 0.1 μM (microM) and 0.5 μM (microM) (FIG. 5B).

FIG. 5A presents comparative plots showing the relative wound width values (microns) as analyzed by IncuCyte.

Figure 5B:
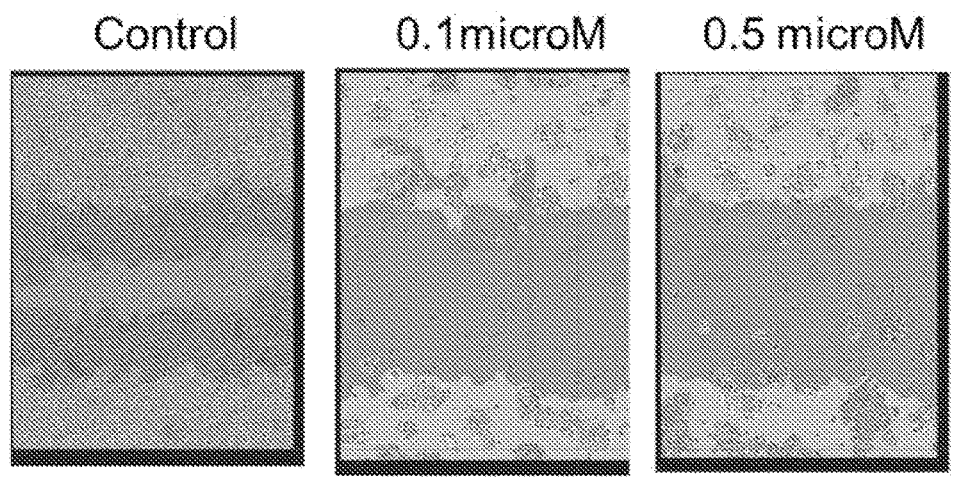

FIG. 5B presents wound width images obtained with the IncuCyte live-cell imaging system at 48 hours for the control, and for cells incubated with BKT300-N1 at a concentration of 0.1 μM and 0.5 μM.

Example 3

In Vitro Cell Viability Assays

Annexin-V Apoptosis Assay:

Apoptosis was determined by flow cytometry analysis using Annexin-V kit. U937 cancer cells were incubated in RPMI cell medium with 1% fetal calf serum (FCS) at a concentration of $1\times10^6$ cells/well at a final volume of 1 ml in 24-well plate. The tested compound (BKT300-N1 or BKT300-3-05) was added to the cells at the indicated concentrations. After 24 hours incubation, medium and cells were collected and centrifuged, then stained with Annexin-V and propidium iodide (PI) kit according to manufacturer's instructions. The numbers of viable cells (Annexin-V negative/PI negative); early apoptotic cells (Annexin-V positive/PI negative); late apoptosis cells (Annexin-V positive/PI positive) and necrotic cells (Annexin-V negative/PI positive) were then evaluated by flow cytometry (FACS).

Figure 6A:
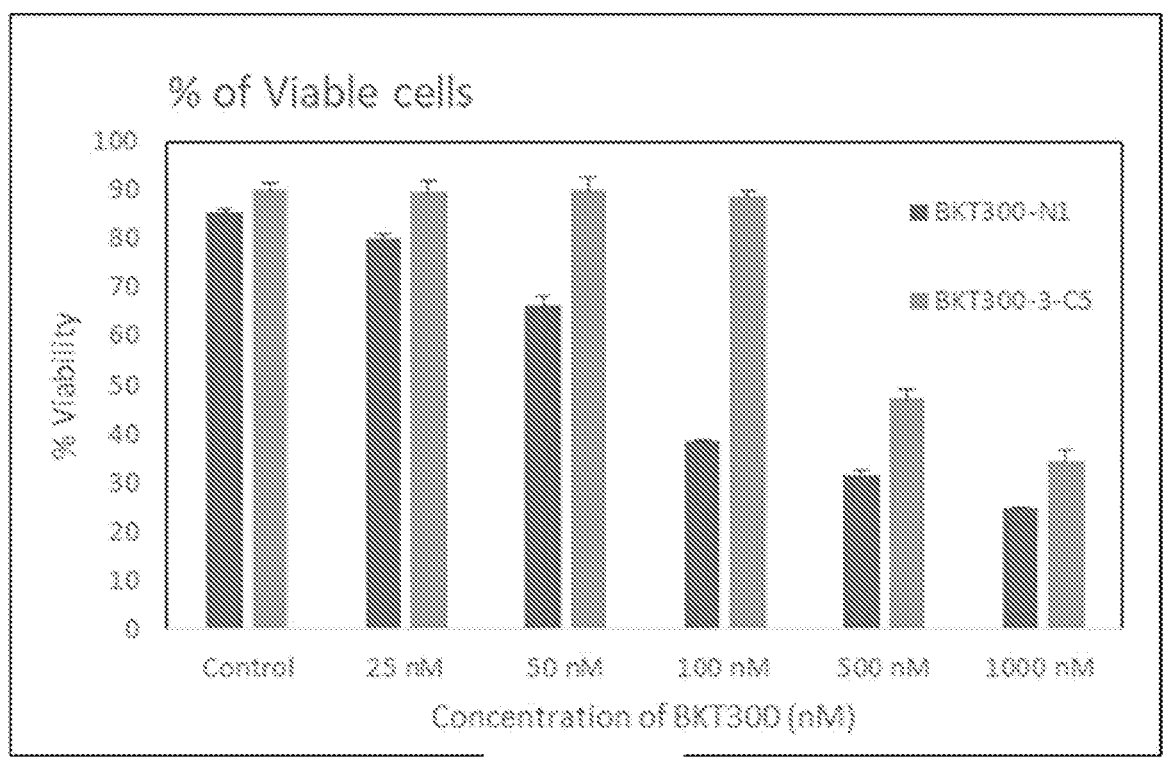
FIGS. 6A-6B are bar graphs present the effect of BKT300-N1 and BKT300-3-05 (25-1000 nM) on viability of U937 cells by showing the number of Annexin-V-/PI-cells (FIG. 6A), and the effect on apoptosis of U937 cells (FIG. 6B).
Figure 6B:
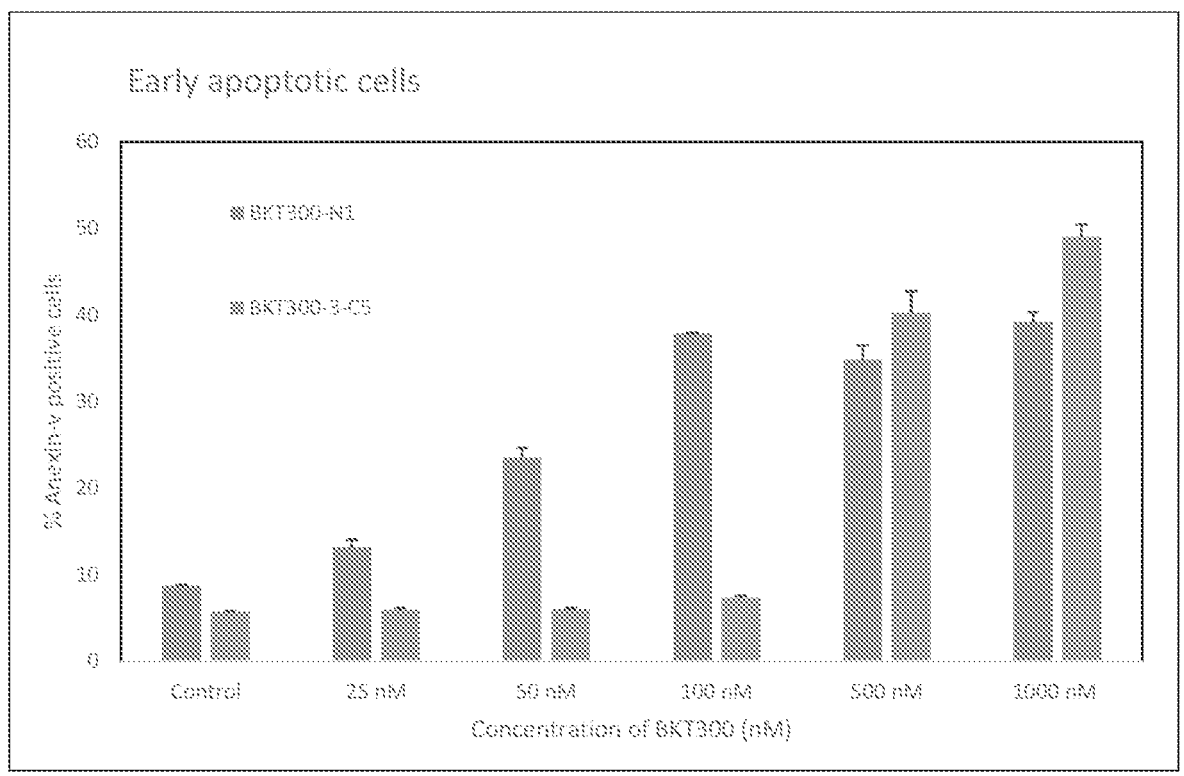

FIGS. 6A-6B present the data obtained in this assay. FIG. 6A is a bar graph showing the effect of BKT300-N1 and BKT300-3-05 (25-1000 nM) on viability of U937 cells as the number of Annexin-V-/PI-viable cells, and demonstrating the improved effect of BKT300-N1 at all the tested concentrations. FIG. 6B is a bar graph showing the effect of BKT300-N1 and BKT300-3-05 (25-1000 nM) on apoptosis of U937 cells by presenting the % of Annexin-V+ cells.

The obtained data clearly show a substantially higher effect of BKT300-N1 in the reduction in the percentage of viable cells via apoptosis.

Western Blot for Cleaved Caspase-3:

The CASP-3 (caspase-3) protein is a member of the cysteine-aspartic acid protease (caspase) family. Sequential activation of caspases plays a central role in the execution-phase of cell apoptosis. Caspases exist as inactive proenzymes that undergo proteolytic processing at conserved aspartic residues to produce two subunits, large and small, that dimerize to form the active enzyme. The active enzyme cleaves and activates caspases 6 and 7, and is processed and activated by caspases 8, 9, and 10.

The role of caspase-3 (CASP3) in the BKT300-N1-induced apoptosis of AML cell lines U937 was tested. Cells were incubated with BKT300-N1 (0.1, 0.5 and 1 μM) for 24 hours, and were then tested for the presence of cleaved caspase 3 using mAb against human cleaved caspase 3 by Western blot assay.

Figure 7A:
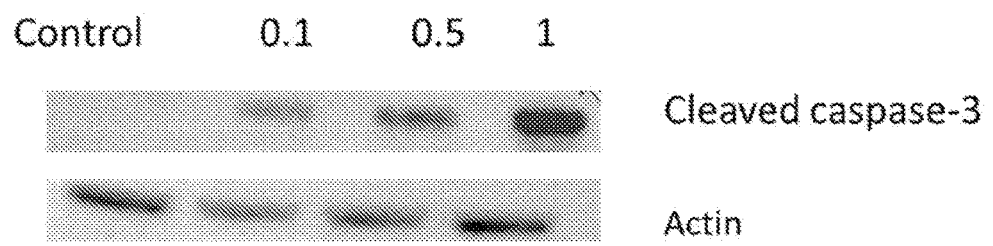
FIGS. 7A-7B present a Western blot showing the effect of 24-hours incubation of BKT300-N1 (0.1, 0.5 and 1 μM) on the presence of cleaved caspase-3 in U937 cells (FIG. 7B) and a bar graph showing the effect of 24-hours incubation of BKT300-N1 (0.1, 0.5 and 1 μM) on the presence of cleaved caspase-3 in U937 cells, as expressed by Optical Density (OD) and normalized to actin (FIG. 7B).
Figure 7B:
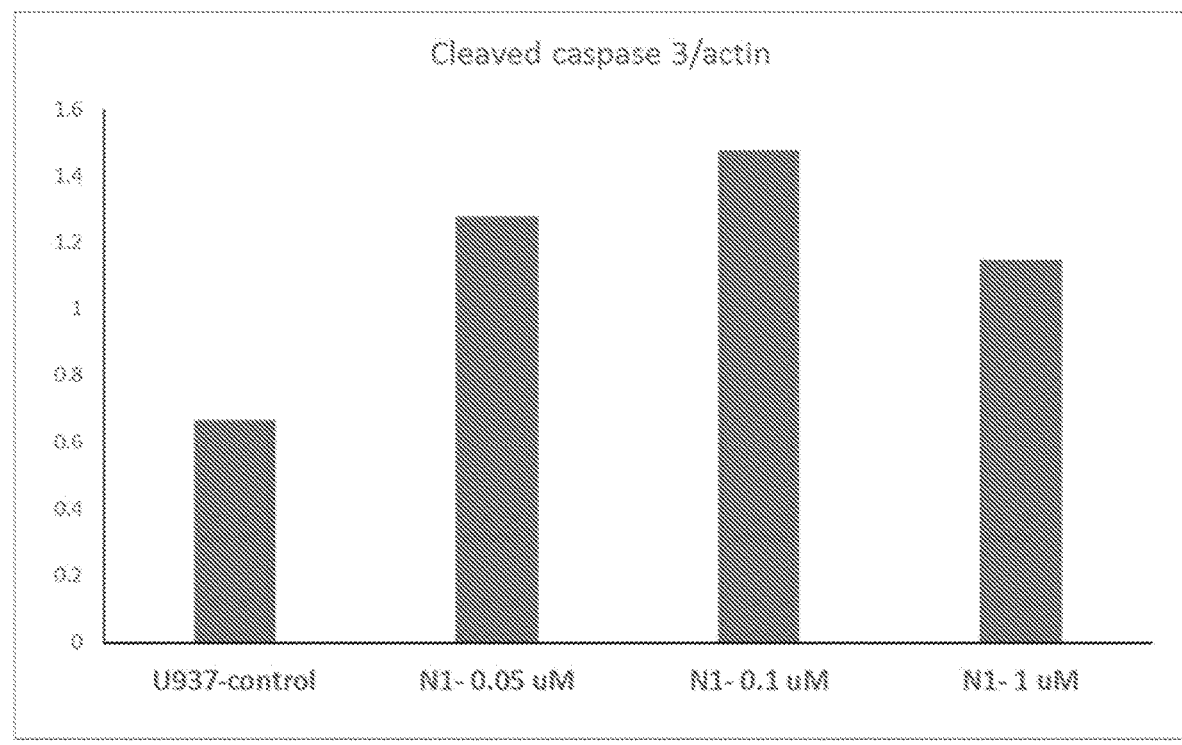

FIG. 7A presents a Western blot showing the effect of 24-hours incubation of BKT300-N1 (0.1, 0.5 and 1 μM) on the presence of cleaved caspase-3 in U937 cells. FIG. 7B is a bar graph showing the effect of 24-hours incubation of BKT300-N1 (0.1, 0.5 and 1 μM) on the presence of cleaved caspase-3 in U937 cells, as expressed by Optical Density (OD) and normalized to actin.

The obtained data clearly show that the BKT300-N1-induced apoptosis is via caspase-3 activation.

Cell Cycle Analysis by 7-AAD Staining:

To evaluate the effects of BKT300-N1 on cell cycle distribution 7-Aminoactinomycin D (7-AAD) protocol was used. Cells were seeded in 24 wells of microplates at a density of $1\times10^6$ Cells/well and exposed to different concentrations of the tested compound, BKT300-N1 or BKT300-3-05, for 24 or 48 hours at 37° C. in a $CO_2$ incubator. After incubation time, cells were collected and washed with cold PBS. Cells were fixed for 20 minutes at 4° C. and processed according to the 7-AAD labeling protocol. The intensity of dye in staining cells was measured by flow cytometry. Cell cycle analysis calculated G0/G1, G2/M and sub-G0 phases from a 7-AAD area histogram.

Using the above protocol, U937 cells were treated with different concentrations of BKT300-N1 or BKT300-3-05 (0.05, 0.1, 0.5 and 1 µM) for 24 hours and then cell cycle phases were analyzed by flow cytometry using 7-AAD.

Figure 8A:
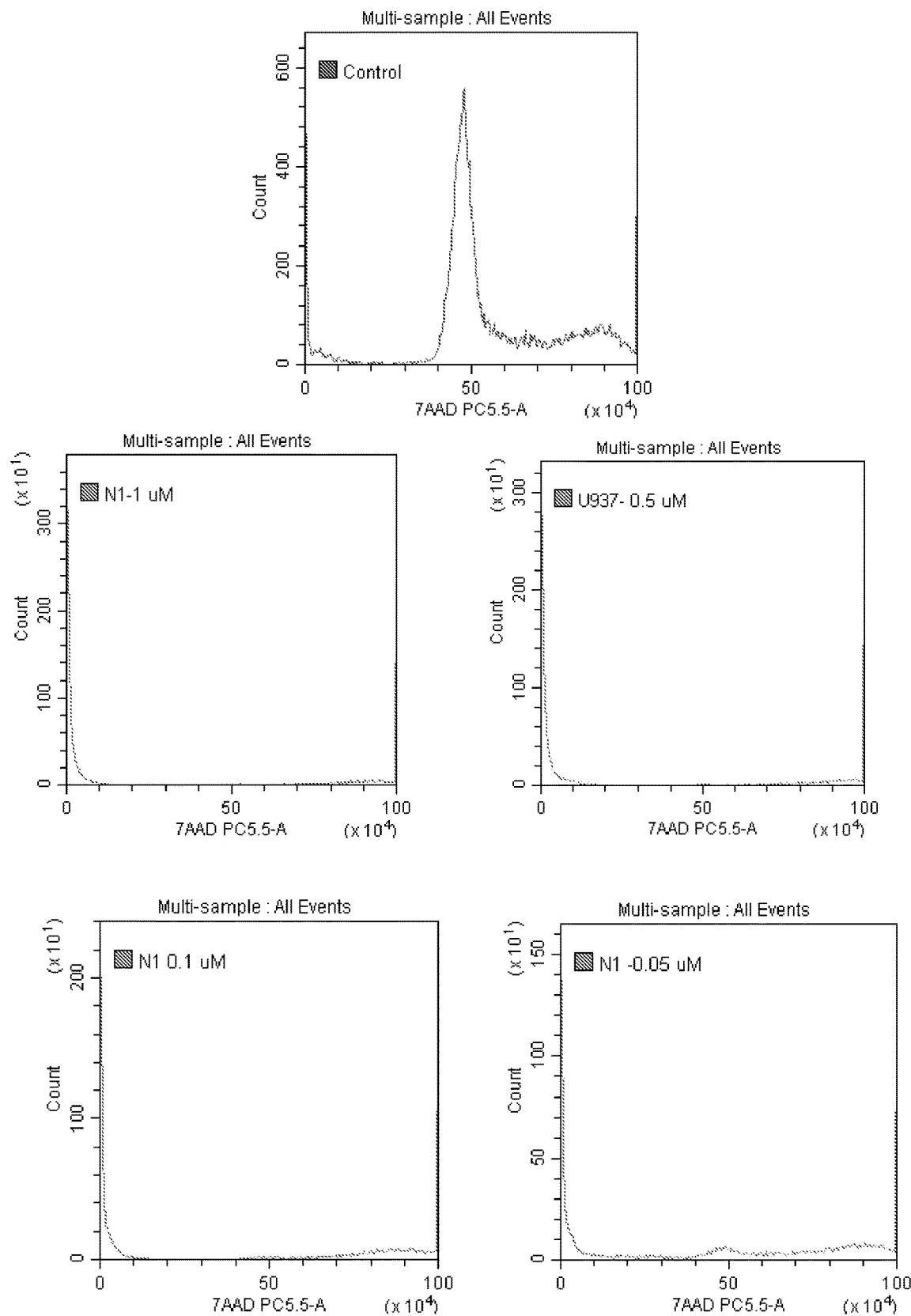
FIGS. 8A-8B present the effect of various concentrations BKT300-N1 (N1) (FIG. 8A) and BKT300-3-05 (FIG. 8B) on cell cycle of U937 cells upon 24 hours incubation. Cell cycle phases were analyzed by flow cytometry using 7-AAD.
Figure 8B:
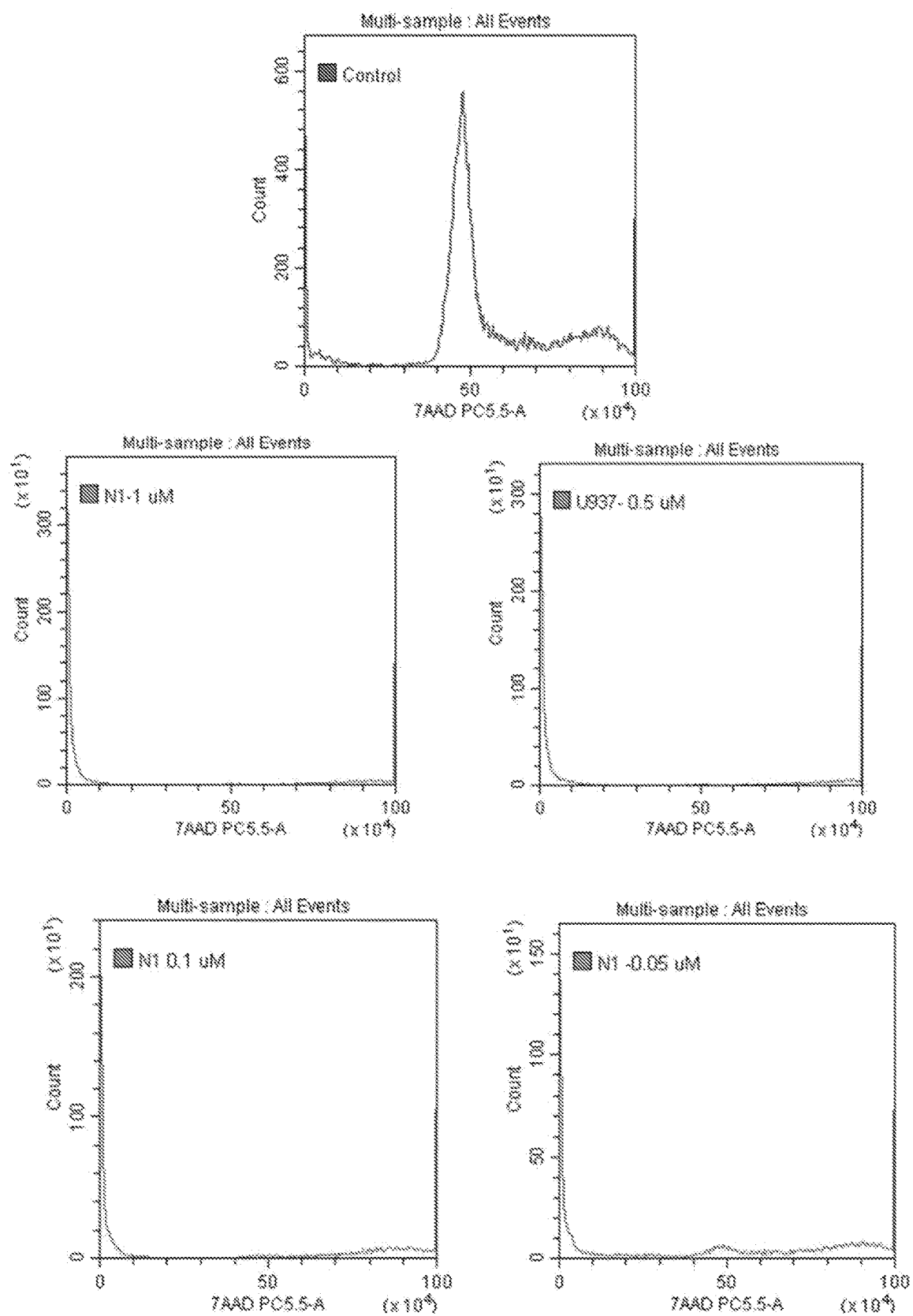

FIG. 8A-8B present the effect of BKT300-N1 (FIG. 8A) and of BKT300-3-05 (FIG. 8B) on the cell cycle of U937 cells and further support the improved effect exhibited by BKT300-N1 over BKT300-3-05, which is even more pronounced at the lower concentrations tested. As shown in FIG. 8A, treatment with BKT300-N1, at all of the tested concentrations, resulted in cell cycle arrest, and induced cells death, whereby, as shown in FIG. 8B, treatment with BKT300-3-05, at a concentration lower than 0.5 µM, did not induce cells death.

Using the above protocol, H69 cells were treated with different concentrations of BKT300-N1 for 48 hours and then cell cycle phases were analyzed by flow cytometry using 7-AAD. Cells were gated according to the cells cycle phase: P1 for G0/G1 phase; P2-apoptotic cells in subG0 phase; and P3 for G2/M phase. The obtained data is presented in FIG. 9.

The obtained data show that BKT300-N1 arrest the growth at the G2M phase of the cell cycle and induce apoptotic cell death.

Figure 9:
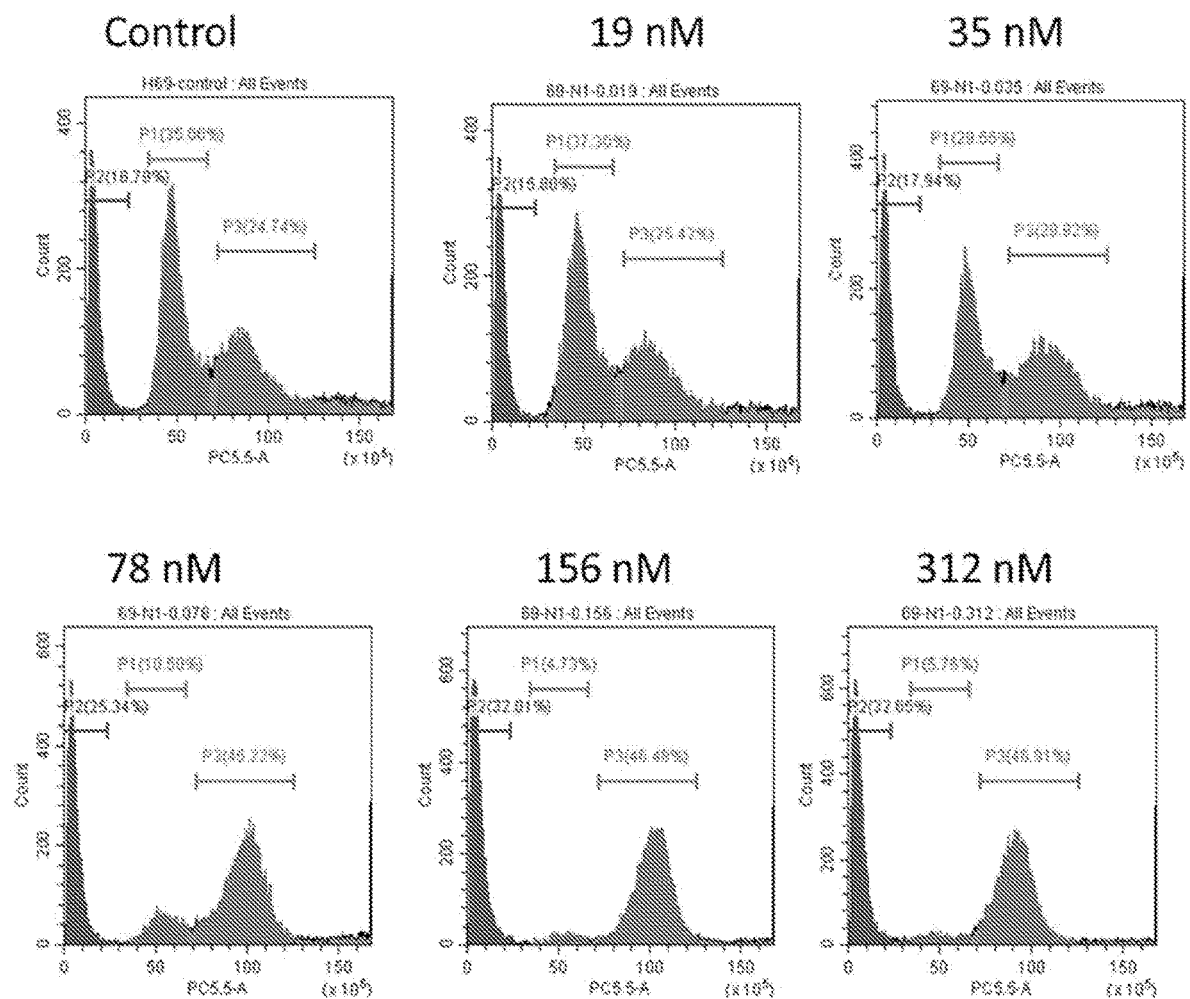
FIG. 9 presents the effect of various concentrations of BKT300-N1 on cell cycle of H69 cells, upon 48 hours incubation. Cell cycle phases were analyzed by flow cytometry using 7-AAD. Cells were gated according to the cells cycle phase: P1 for G0/G1 phase; P2-apoptotic cells in subG0 phase; and P3 for G2/M phase.
Figure 9:
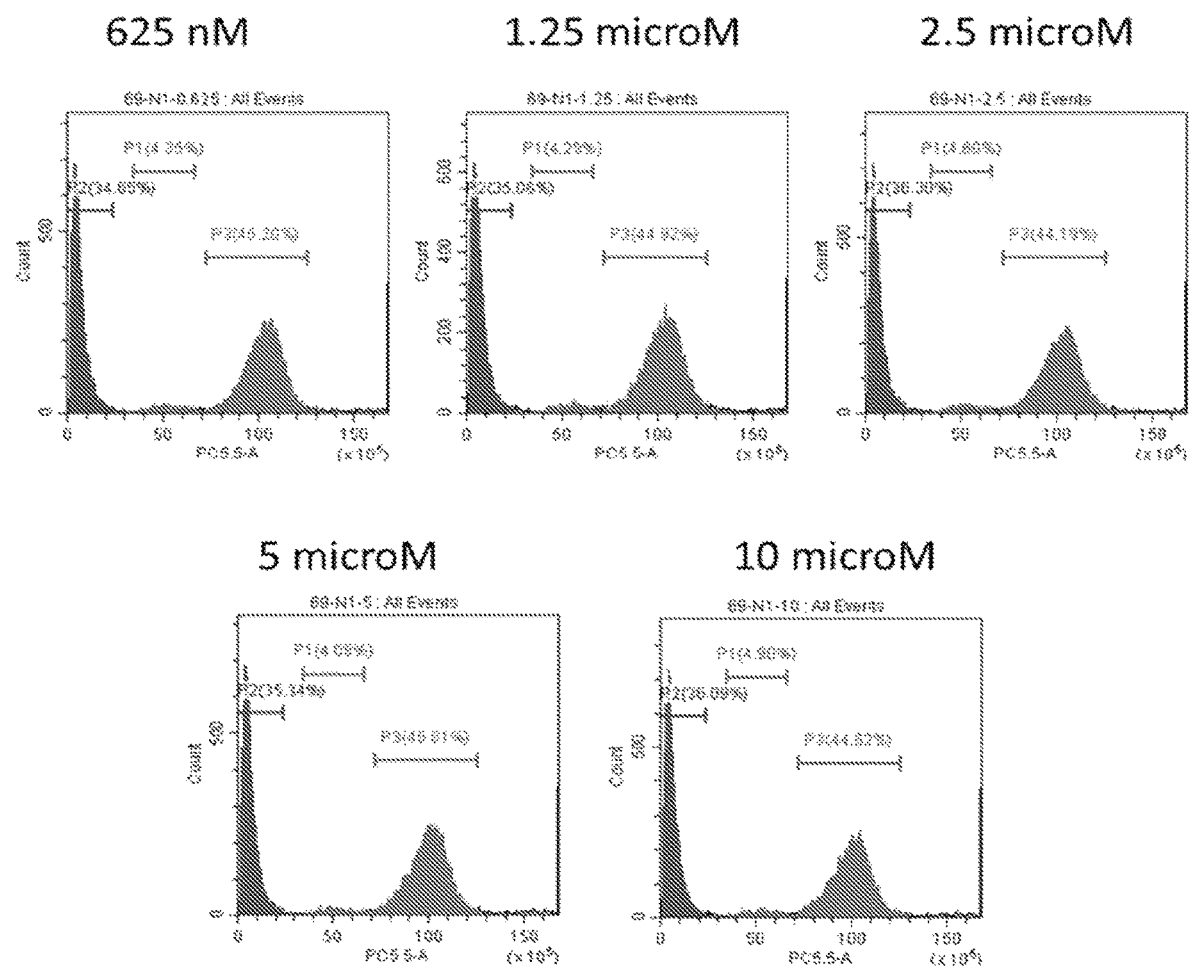

The data presented in FIGS. 8A-8B and 9 further show an improved activity of BKT300-N1 in cell cycle arrest of variable cancer cells.

Example 4

In Vivo Studies

The effect of BKT300-N1 on cancer cells proliferation and survival in vivo was examined in NOD Scid gamma (NSG) mice or C57BL/6 mice.

C57BL/6 mice were SC transplanted with the murine pancreatic cell line Panc02, $5\times10^6$ cells/mouse.

NSG mice were SC transplanted with the human hepatocellular carcinoma cell line SNU449 or with the human AML cell line U937, $5\times10^6$ cells/mouse.

When the tumors reached considerable size and were clearly visible the treated group was injected with BKT300-N1. BKT300-N1 (30 mg/ml formulated in Cremophor EL 49.7% (V/V) Dehydrated Ethanol and further diluted 1:6 with 0.9% NaCl to 5 mg/ml) was SC injected at a dose of 2.5 mg/mouse per injection for three-four consecutive days. Some mice were treated with intra-tumor injection of BKT300-N1 (30 mg/ml formulated in Cremophor EL 49.7% (V/V) Dehydrated Ethanol) at a dose of 0.6 mg/mouse per injection for two-four consecutive days. 24 hours after the last treatment mice were sacrificed and the size of tumor was evaluated and weighted.

C57BL6 mice bearing Panc02 SC tumors were treated with BKT300-N1 (30 mg/ml formulated in Cremophor EL 49.7% (v/v) Dehydrated Ethanol and further diluted 1:6 with 0.9% NaCl to 5 mg/ml). BKT300-N1 was SC injected at a dose of 2.5 mg/mouse or intratumorally injected at a dose of 0.6 mg/mouse. BKT300-N1 was injected daily for 4 times.

Figure 10:
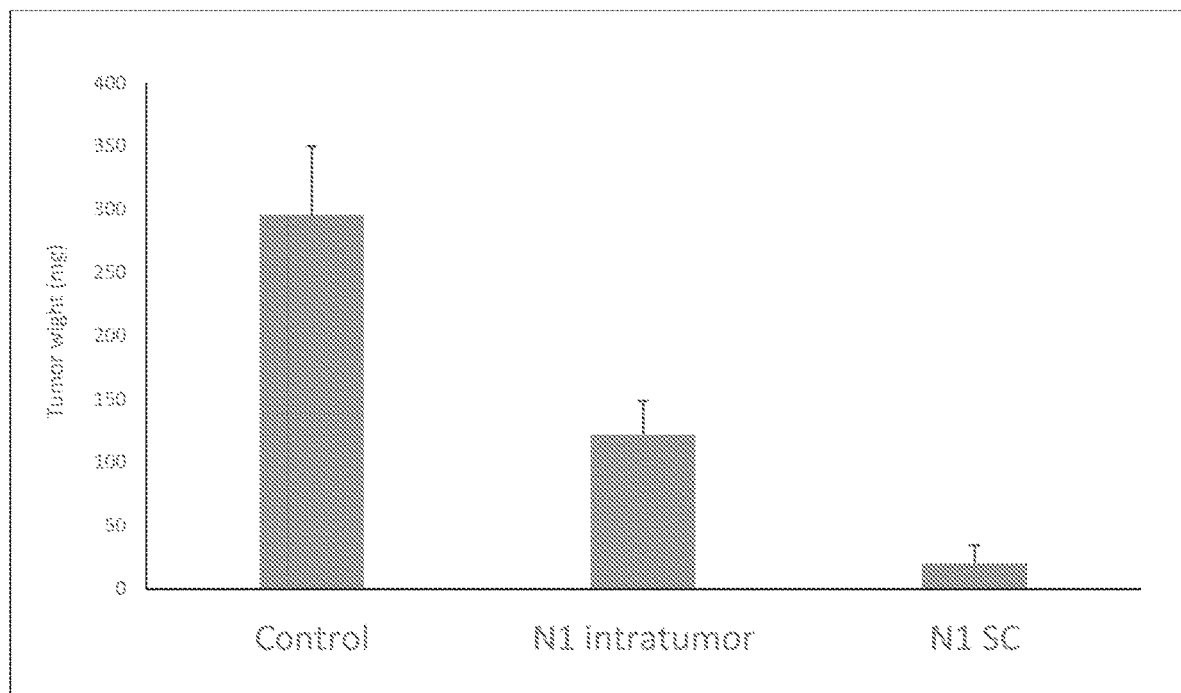
FIG. 10 is a bar graph showing the in vivo effect of BKT300-N1 on pancreatic cancer in mice. The bar graph shows tumor weight (mg) (*$p<0.05$).

FIG. 10 is a bar graph showing the in vivo effect of BKT300-N1 on pancreatic cancer in mice by showing tumor weight (mg) following treatment (*p<0.05).

NSG mice bearing U937 SC tumors were treated with BKT300-N1 (30 mg/ml formulated in Cremophor EL 49.7% (v/v) Dehydrated Ethanol and further diluted 1:6 with 0.9% NaCl to 5 mg/ml). BKT300-N1 was SC injected at a dose of 2.5 mg/mouse daily for 4 days or intratumorally injected at a dose of 0.6 mg/mouse daily for 2 days.

Figure 11:
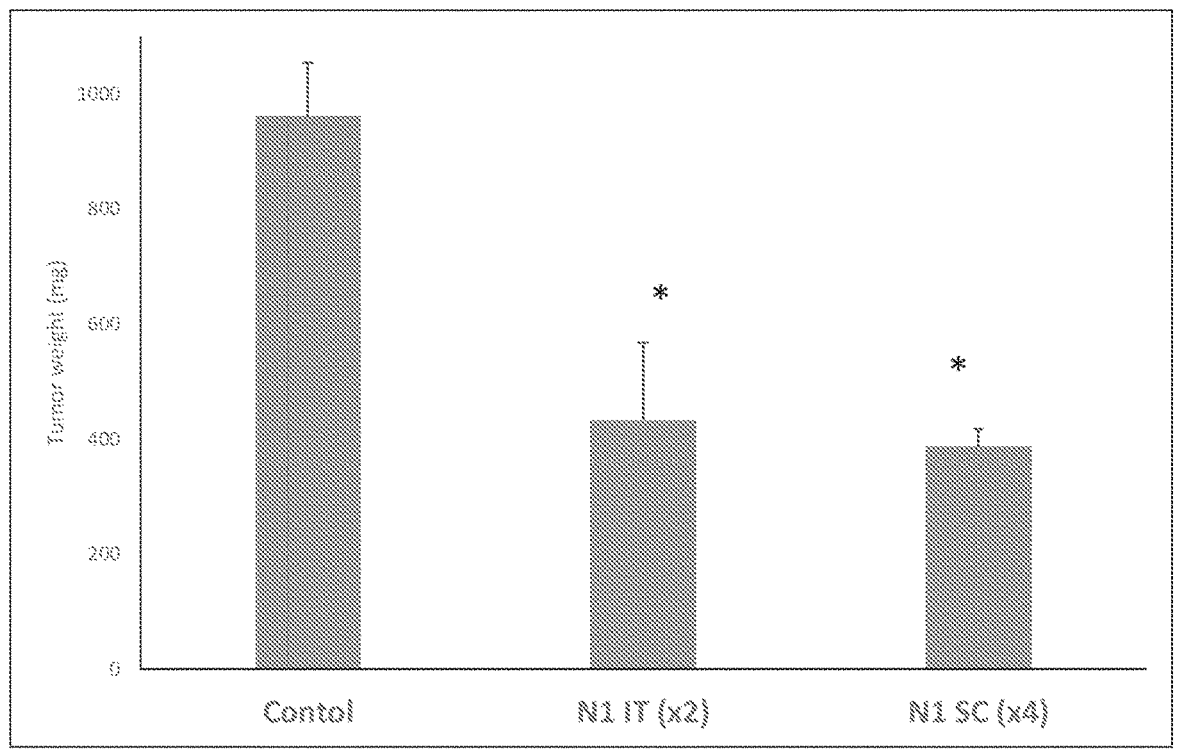
FIG. 11 is a bar graph showing the in vivo effect of BKT300-N1 on AML in mice. The bar graph shows tumor weight (mg) (*$p<0.05$).

FIG. 11 is a Bar graph showing the in vivo effect of BKT300-N1 on AML in mice by showing the tumor weight (mg) following treatment (*p<0.05).

NSG mice bearing SNU449 SC tumors were treated with BKT300-N1 (30 mg/ml formulated in Cremophor EL 49.7% (v/v) Dehydrated Ethanol and further diluted 1:6 with 0.9% NaCl to 5 mg/ml). BKT300-N1 was SC injected at a dose of 2.5 mg/mouse daily for 3 days.

Figure 12:
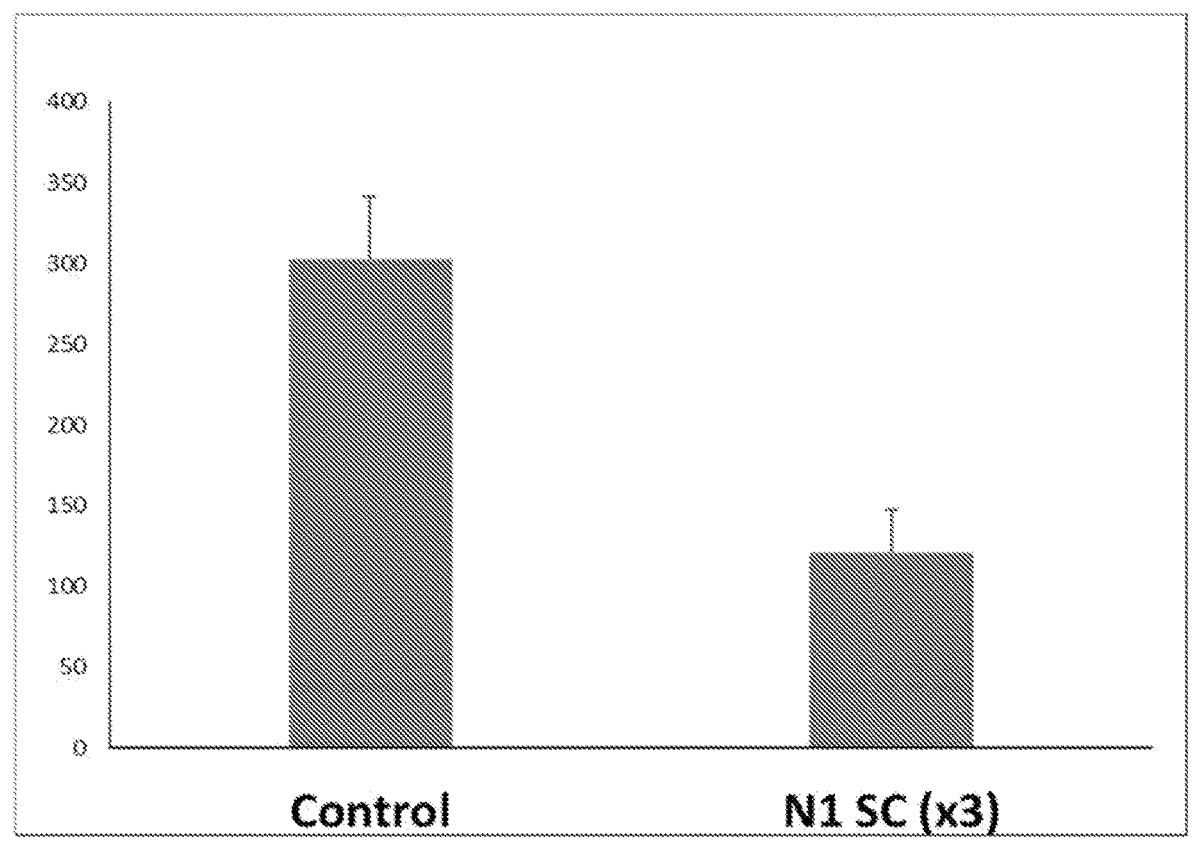
FIG. 12 is a bar graph showing the in vivo effect of BKT300-N1 on hepatocellular carcinoma in mice. The bar graph shows tumor weight (mg) (*$p<0.05$).
Figure 13A:
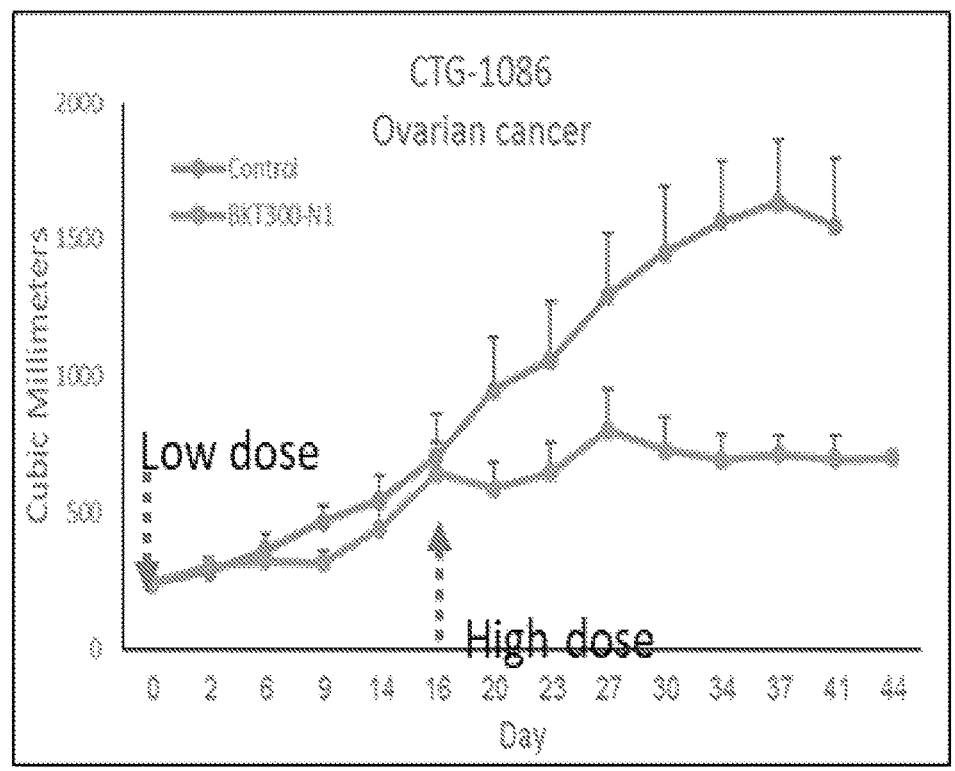
FIGS. 13A-13C present comparative plots showing in vivo effect of BKT300-N1, at a daily dose of 5 mg (low dose) or 10 mg (high dose), on the growth of human-derived ovarian cancer (FIG. 13A), Small Lung Cancer Cells (SCLS.
Figure 13B:
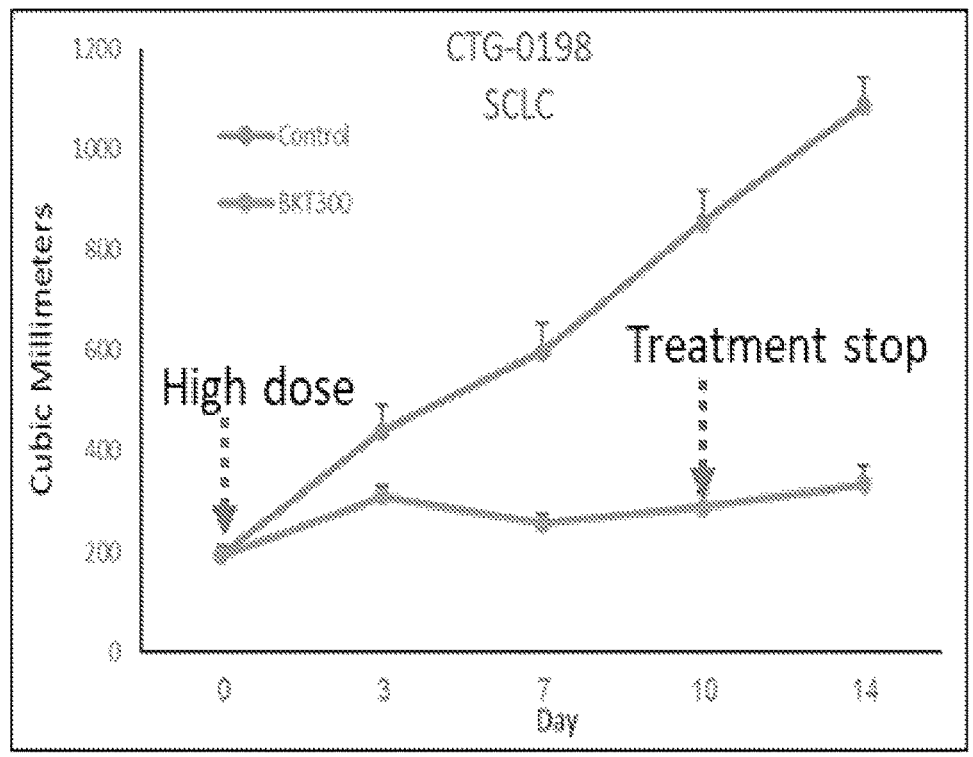
Figure 13C:
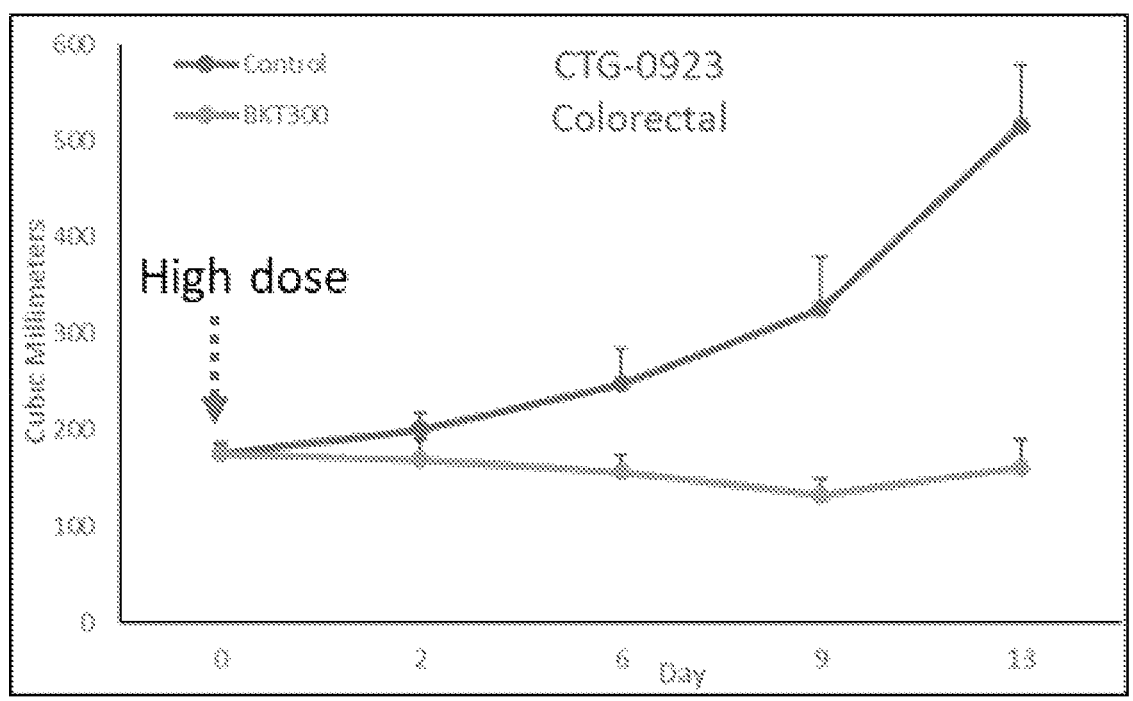

FIG. 12 is a bar graph showing the in vivo effect BKT300-N1 on hepatocellular carcinoma in mice, by showing tumor weight (mg) following treatment (*p<0.05).

In additional experiments, the in vivo efficacy of BKT300-N1, on the growth of subcutaneous, low passage Champions' TumourGraft® patient derived xenograft (PDX) models of human non-small-cell lung (CTG-0198), colorectal (CTG-0923) and ovarian (CTG-1086) cancer in female immunocompromised mice was tested.

Athymic Nude-Foxn1nu (Immunocompromised) female mice aged 6-8 weeks were implanted with 1-1.5 $cm^3$ harvested tumors unilaterally on the left flank. When the tumors reached an average volume of 200 cubic millimeters, control group was treated daily with a vehicle and treatment group was treated with either 2.5 mg per mice per injection (low dose) or 5 mg per mice per injection (hight dose) of BKT300-N1. The control group was subcutaneously (SC) injected with the vehicle (Cremophore EL and Ethanol 50%/50% volume/volume) diluted 1:6 with 0.9% Sodium Chloride.

For the low dose treatment group, a stock solution of 30 mg/mL BKN300-N1 was prepared in the vehicle and further diluted 1:6 with 0.9% Sodium Chloride, to a final concentration of 5 mg/mL. Animals received a 0.5 mL subcutaneously (SC) injection every 12 hours (for a 2.5 mg/injection=5 mg daily dose).

For the high dose treatment group, a stock solution of 30 mg/mL BKN300-N1 was prepared in the vehicle and further diluted 1:3 with 0.9% Sodium Chloride, to a final concentration of 10 mg/mL. Animals received a 0.5 mL subcutaneously (SC) injection every 12 hours (for a 5 mg/injection=10 mg daily dose) The obtained data is presented in FIGS. 13A-13C, and clearly show the substantial reduction and even arrest in tumor growth in the treated groups compared to the control, in all tested tumors.

These results further indicate that BKT300-N1 is effective at inhibiting tumor growth of variable cancer types.

Example 5

Combination Treatment of BKT300-N1 and Irinotecan

H460 cells ($1\times10^6$ cells/ml) were cultured in 12-well plates with 10% FCS (fetal calf serum). After 24 hours, the medium was replaced by 1% FCS, and BKT300-N1 (125 nM), Irienotecan (25 or 100 µM), or a combination of BKT300-N1 (125 nM) and Irinotecan (25 or 100 µM), respectively, were added.

After 24 or 48 hours of incubation, medium and cells were collected and centrifuged, then stained with propidium iodide (PI; 1:100) kit according to manufacturer's instructions. The numbers of viable cells (PI negative) and dead cells (PI positive), following 24 or 48 hours incubation, were then evaluated by flow cytometry (FACS).

Figure 14A:
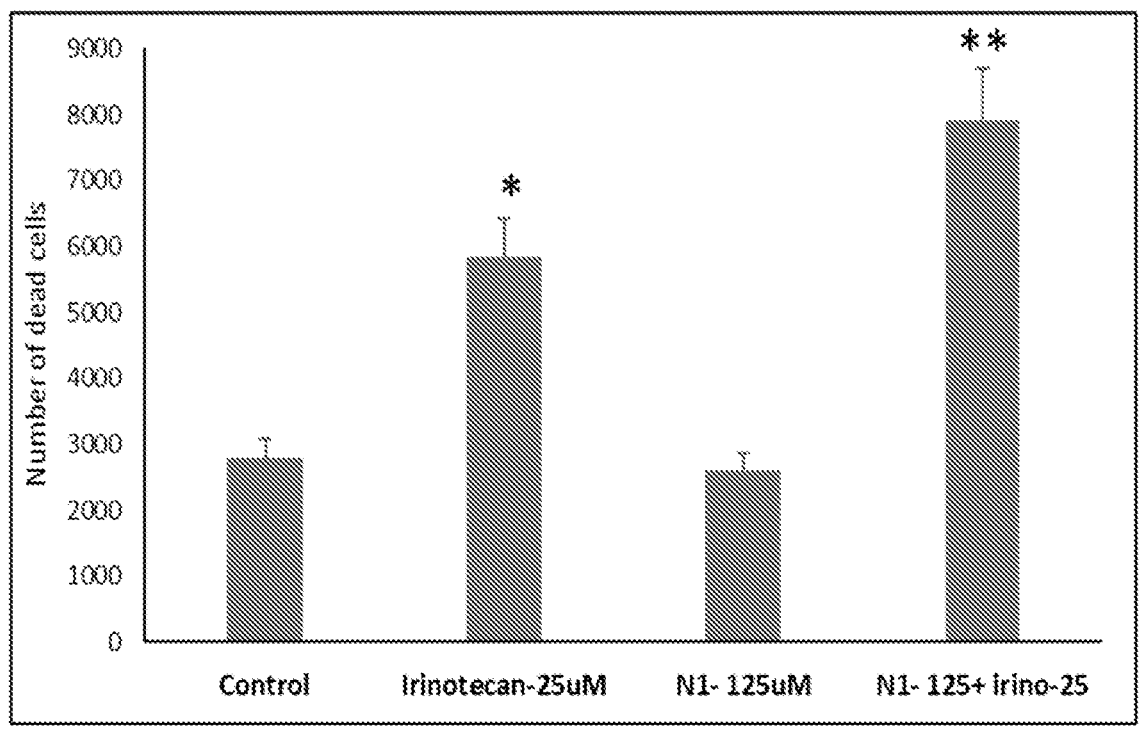
FIGS. 14A-14D are bar graphs showing the effect on the viability of H460 cells, following treatment with BKT300-N1 (125 nM) and Irinotecan (25 μM) for 24 hours (FIG. 14A), with BKT300-N1 (125 nM) and Irinotecan (100 μM) for 24 hours (FIG. 14B), with BKT300-N1 (125 nM) and Irinotecan (25 μM) for 48 hours (FIG. 14C), and with BKT300-N1 (125 nM) and Irinotecan (100 μM) for 48 hours (FIG. 14D), as determined upon PI-staining.
Figure 14B:
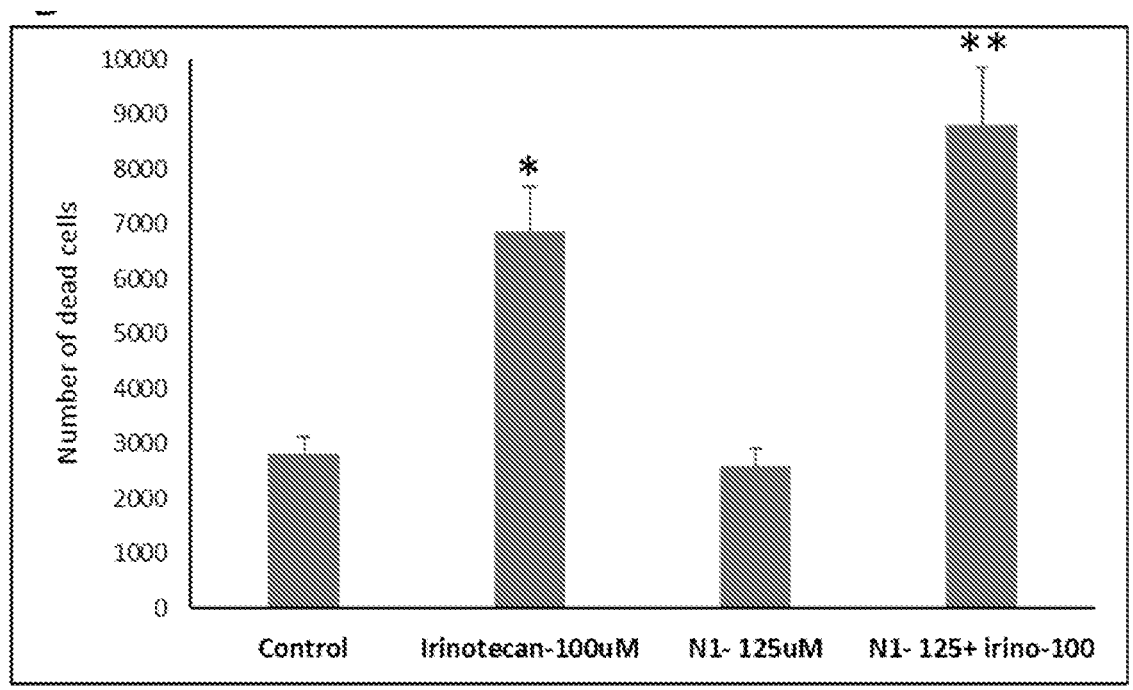
Figure 14C:
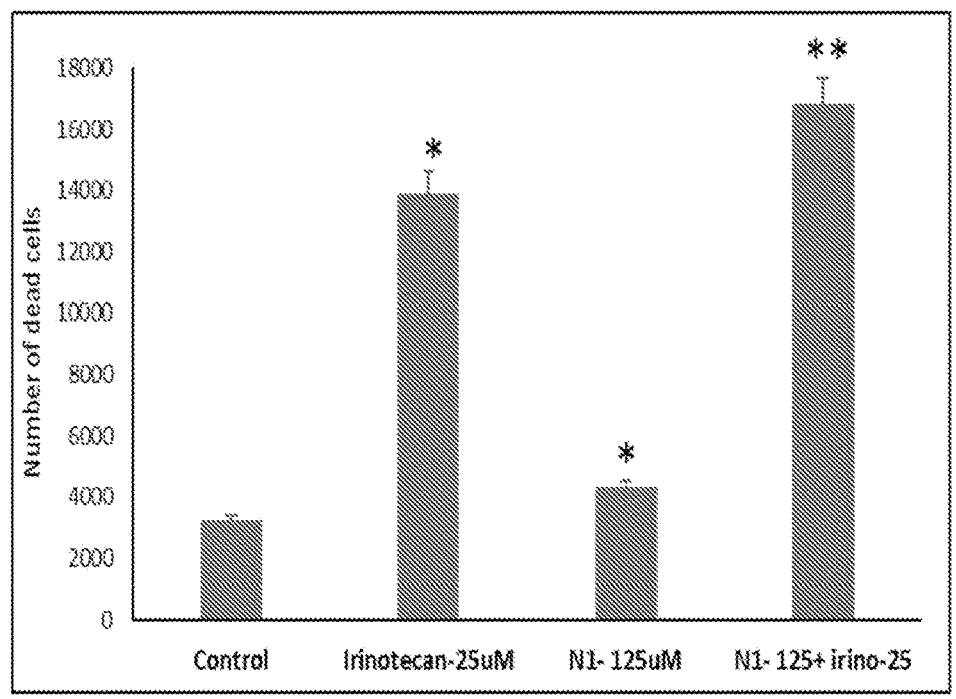
Figure 14D:
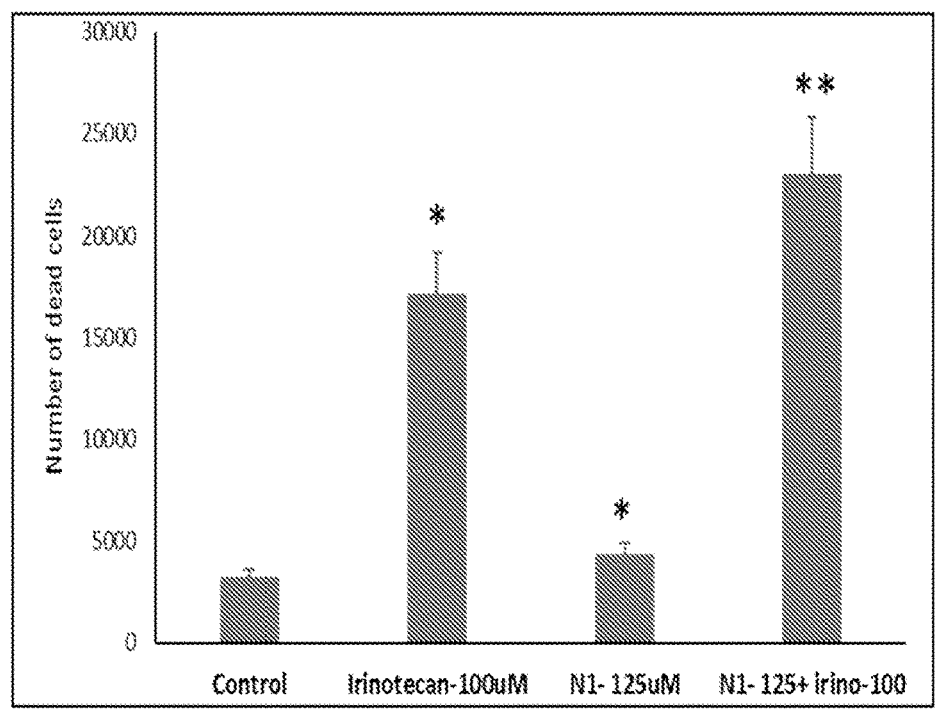

The obtained data is presented in FIGS. 14A-14D, with FIGS. 14A-14B showing data obtained upon 24 hours incubation and FIGS. 14C-14D showing data obtained upon 48 hours incubation. Results are expressed as average±SD. Statistical differences were determined by an analysis of two-tailed Student's t test. Values of $p<0.05$ were considered to be statistically significant. The data are the average±SD of number of cells from duplicates per group. *$p<0.05$ versus control; **$p<0.05$ versus Irinotecan alone.

As can be seen in FIGS. 14A-14D, a combination treatment of BKT300-N1 and Irinotecan shows a beneficial effect on the survival of the tested lung cancer cells. The combined therapy induces higher number of cell death than each treatment individually, suggesting a synergitic effect. Such a synergistic effect allows using smaller amounts of irinotecan and may reduce acquired resistance to Irinotecan treatment.

Example 6

Taxol-Resistant Cancer Cells

Taxol is a chemotherapeutic agent leading to mitotic arrest and cell death by interacting directly with microtubules and stabilizing them against depolymerization. However, its clinical efficacy has been hampered due to the development of drug resistance. Taxol resistance represents a major challenge in the treatment of various types of cancer.

The effect of BKT300-N1 on Taxol resistance cells was therefore tested, using the following protocol.

Cells ($1\times10^6$ cells/ml) were cultured in 12-well plates in 10% FCS. After 24 hours the medium was replaced by 1% FCS and BKT300-N1 or Taxol (250-3.75 nM) were added. 24 hours incubation, cells were harvested and washed with PBS. The pellet was fixed by adding 200 µl Fix/Perm buffer and vortexed. The fixed cells were incubated for 20 minutes at 4° C. and then 1 ml of Perm/Wash buffer was added. Following centrifugation, supernatant was removed and cells were resuspended in 100 µl Perm/Wash plus 4 µl of 7-AAD and vortexed. The cells were then incubated in the dark for 20 minutes at 4° C. and thereafter 300 µl of PBS was added. Flow cytometry analysis was performed by collecting 20,000 events per sample. Analysis was done according to the distribution of cells in three major phases of the cycle: G0/G1 (blue), S (purple), G2/M (green), and apoptotic cells (red), as shown in FIGS. 15-18C.

All results are expressed as average±SD. Statistical differences were determined by an analysis of two-tailed Student's t test. Values of $p<0.05$ were considered to be statistically significant.

In a first set of experiments, the sensitivity of two ovarian cancer cell lines, OVCAR8 and HEY-T30, to taxol, was tested.

Cells were incubated in different doses of Taxol (30, 15, 7.5, 3.75 nM) for 24 hours and were thereafter analyzed as described hereinabove.

Figure 15:
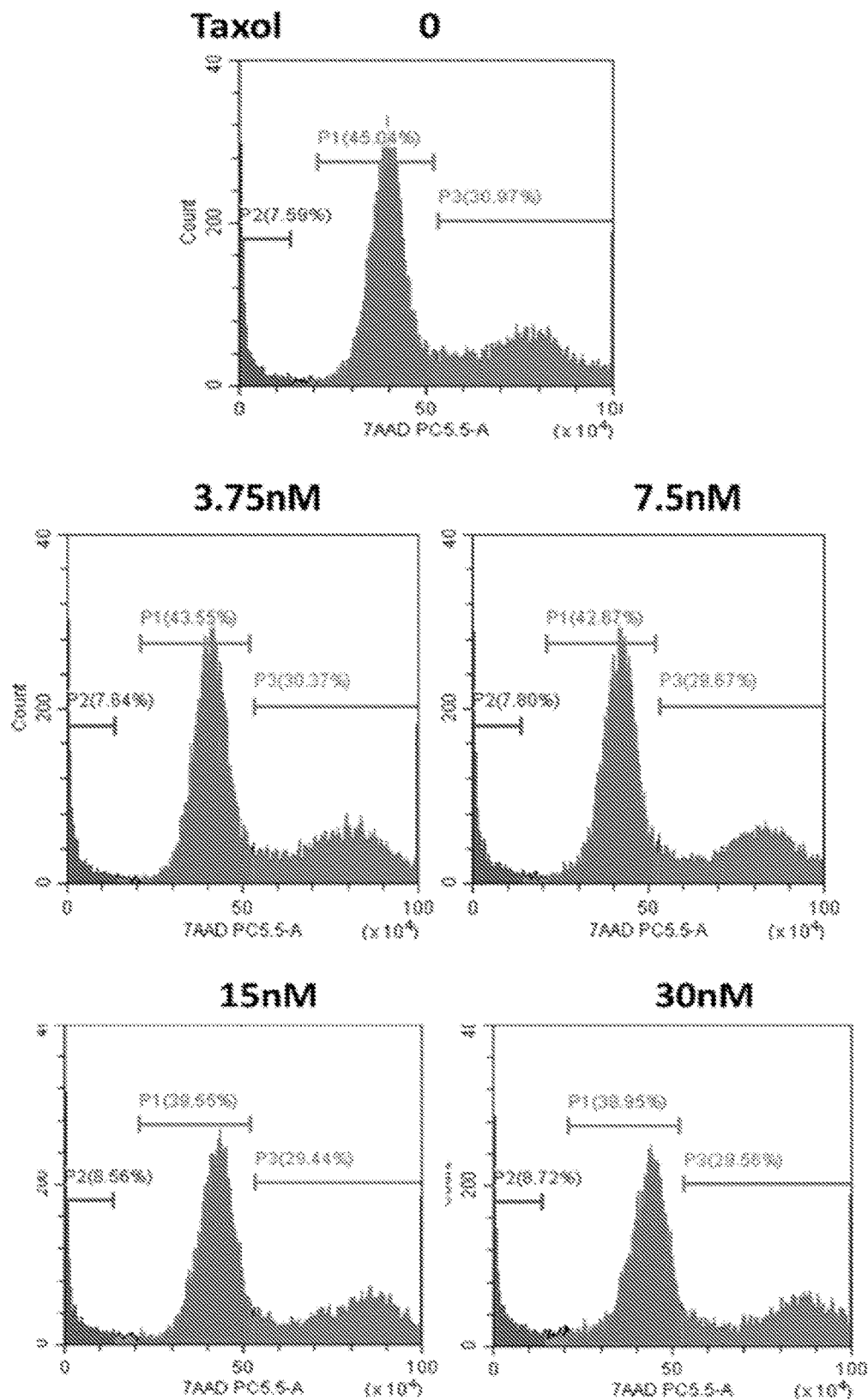
FIG. 15 presents FACS analysis of HEY-T30 cells following treatment with Taxol. Red area represents cells in the G0/G1 phase (P1), Green area represents cells in the G2/M phase (P3), and Blue area represent apoptotic cells (P2).

The data obtained for Hey-T30 cells is presented in FIG. 15. As can be seen, no effect on cell cycle was observed in HEY-T30 cells following treatment with Taxol, indicating that these cells are resistant to Taxol at a concentration of up to 30 nM.

Figure 16:
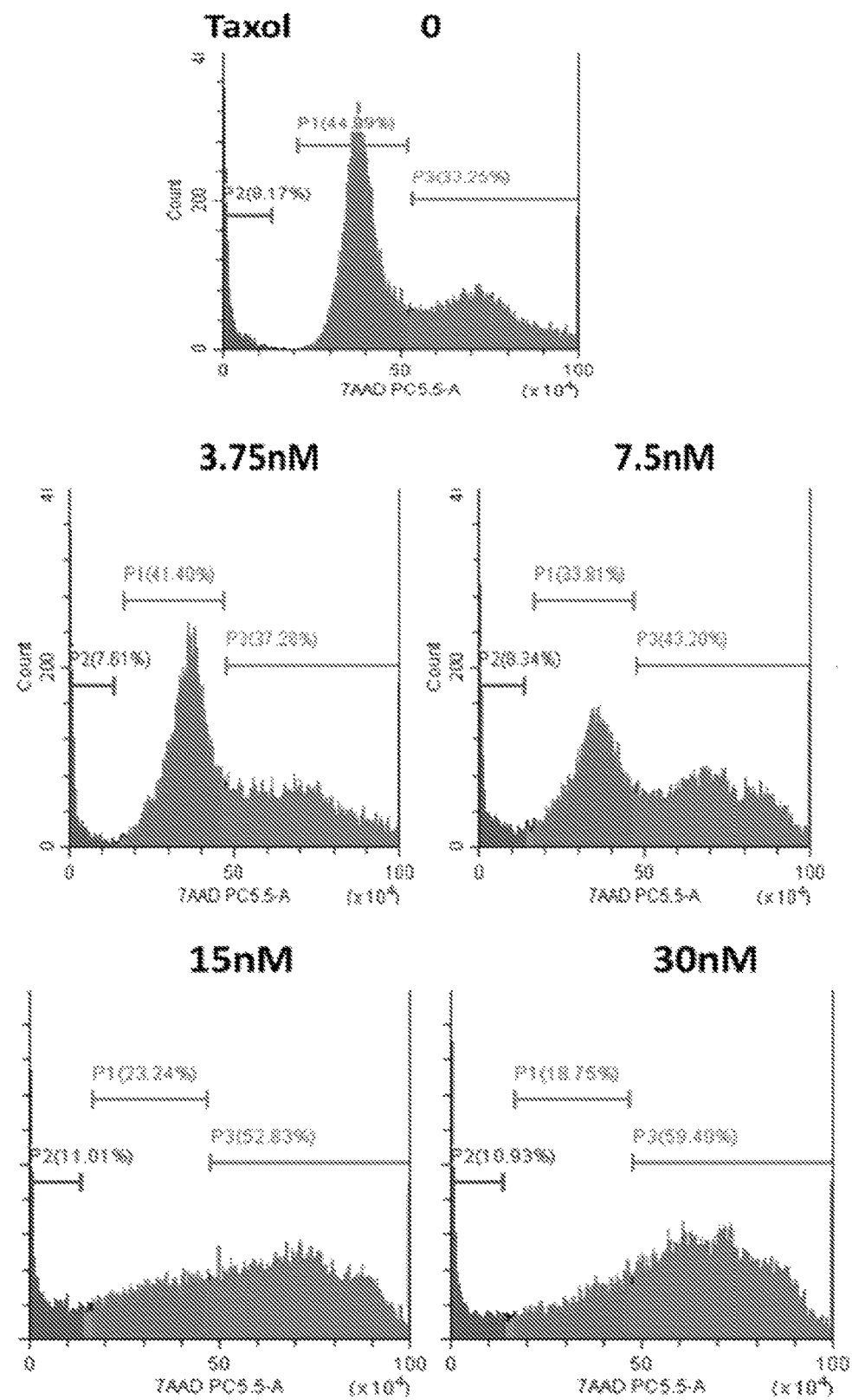
FIG. 16 presents FACS analysis of OVCAR8 cells following treatment with Taxol. Red area represent cells in the G0/G1 phase (P1), Green area represent cells in the G2/M phase (P3), Blue area represent apoptotic cells (P2).

The data obtained for OVCAR8 cells is presented in FIG. 16. As can be seen, an effect on cell cycle was already evident in the lowest taxol concentration of 3.75 nM, indicating that OVCAR8 cells are sensitive to Taxol.

Figure 17A:
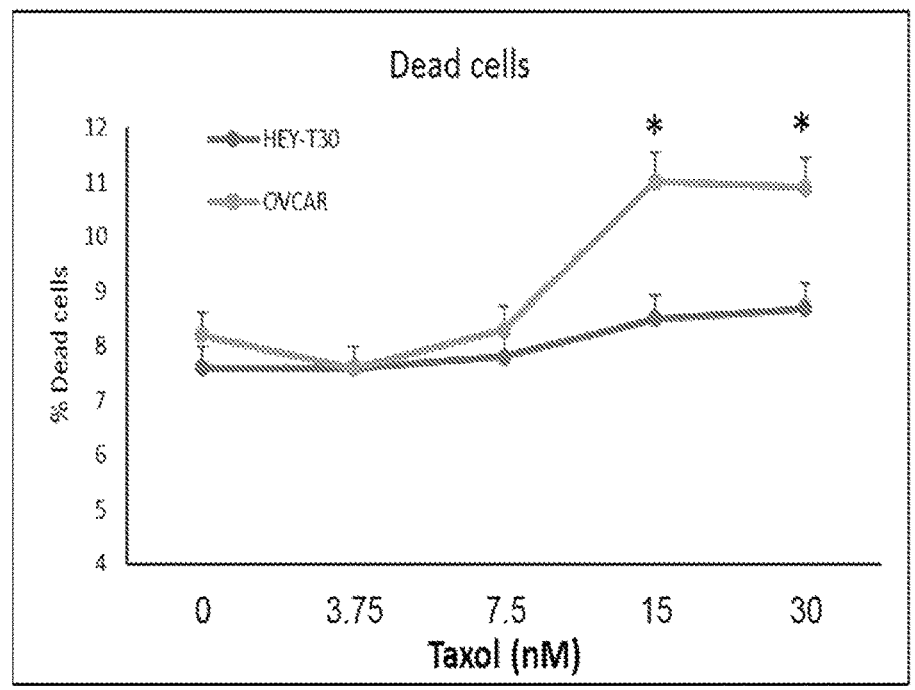
FIGS. 17A-17C present comparative plots showing the cell cycle analysis of HEY-T30 (Blue line) and OVCAR8 (orange line) cells following treatment with Taxol (30, 15, 7.5 and 3.75 nM).
Figure 17B:
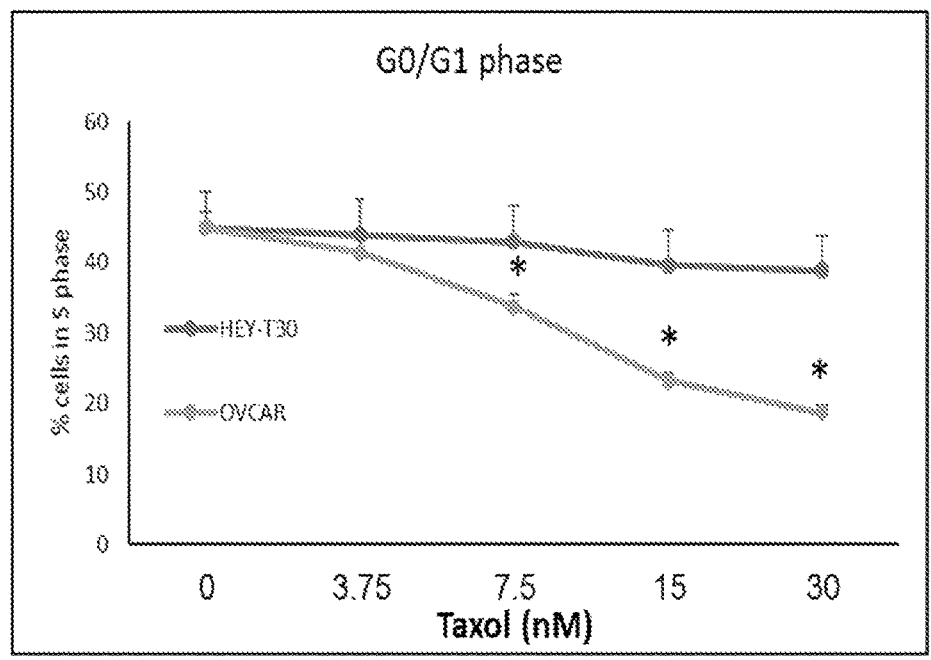
Figure 17C:
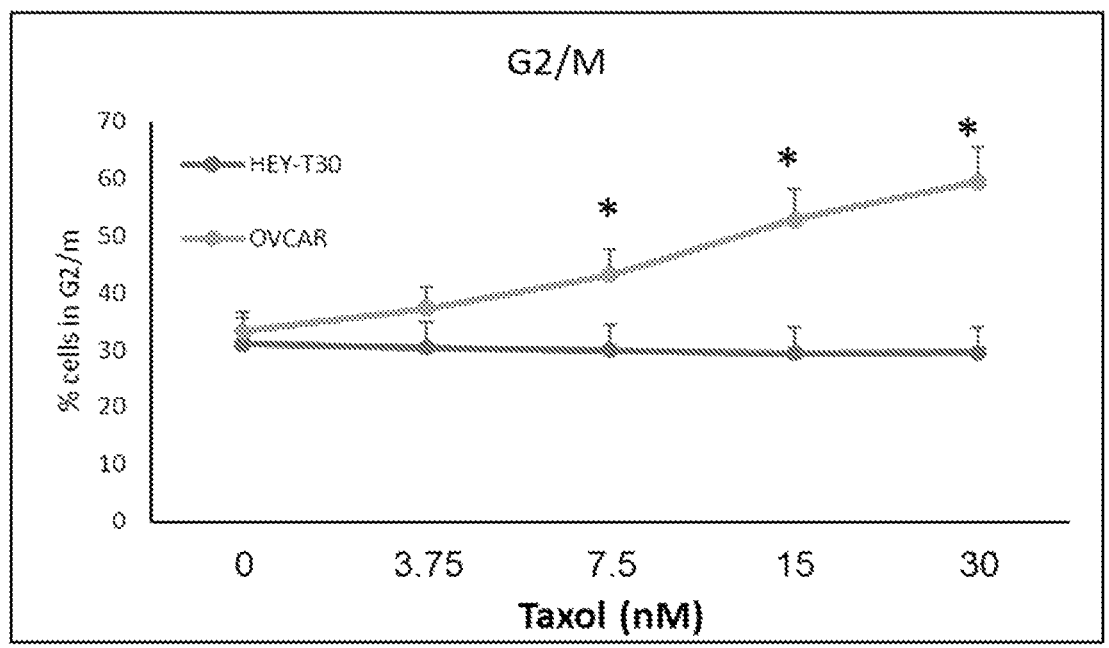

FIGS. 17A-17C are graphical representations comparing the effect of taxol in the two tested cell lines on cells viability, the percentage of cells at G0/G1 phase and the level of cells in G2/M phase, further demonstrating the resistance of the HEY-T30 cells to taxol compared with the sensitivity of OVCAR8 cells to taxol.

Next, the effect of BKT300-N1 on the taxol resistance cells was tested. Both ovarian cancer cell lines were incubated with BKT300-N1 (250, 125, 62.5, 31.25, 15.6 nM). For comparison, the effect of the same amounts of Taxol was also tested.

Figure 18A:
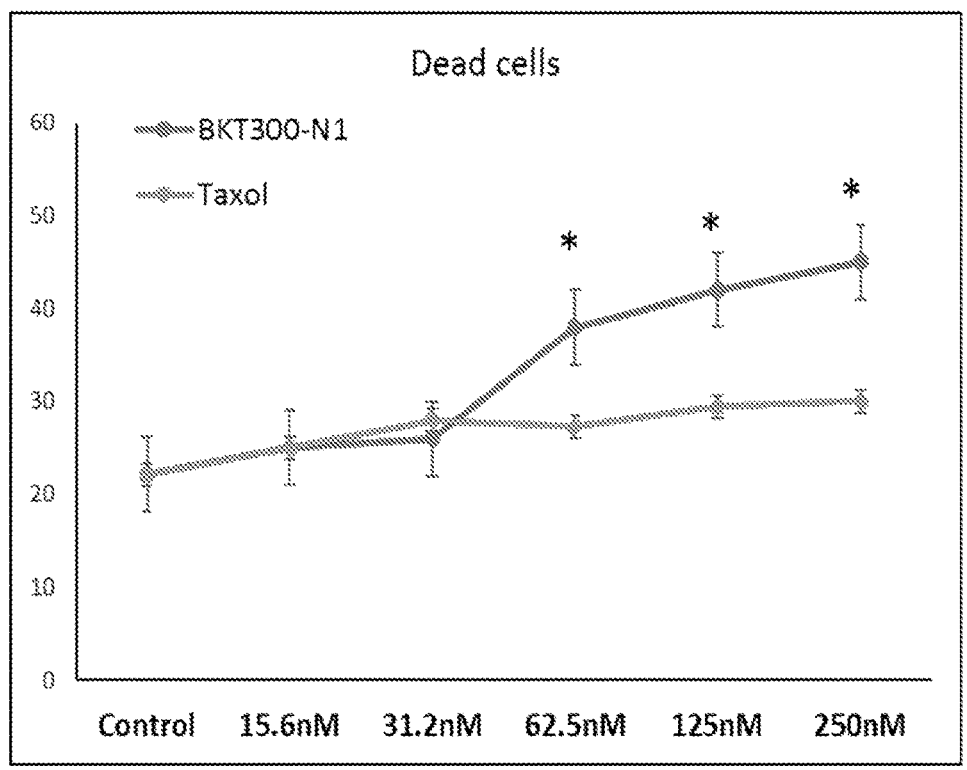
FIGS. 18A-18C present comparative plots showing the cell cycle analysis of HEY-T30 cells following treatment with 250, 125, 62.5, 31.25 and 15.6 nM of Taxol (Green line) or BKT300-N1 (Red line).
Figure 18B:
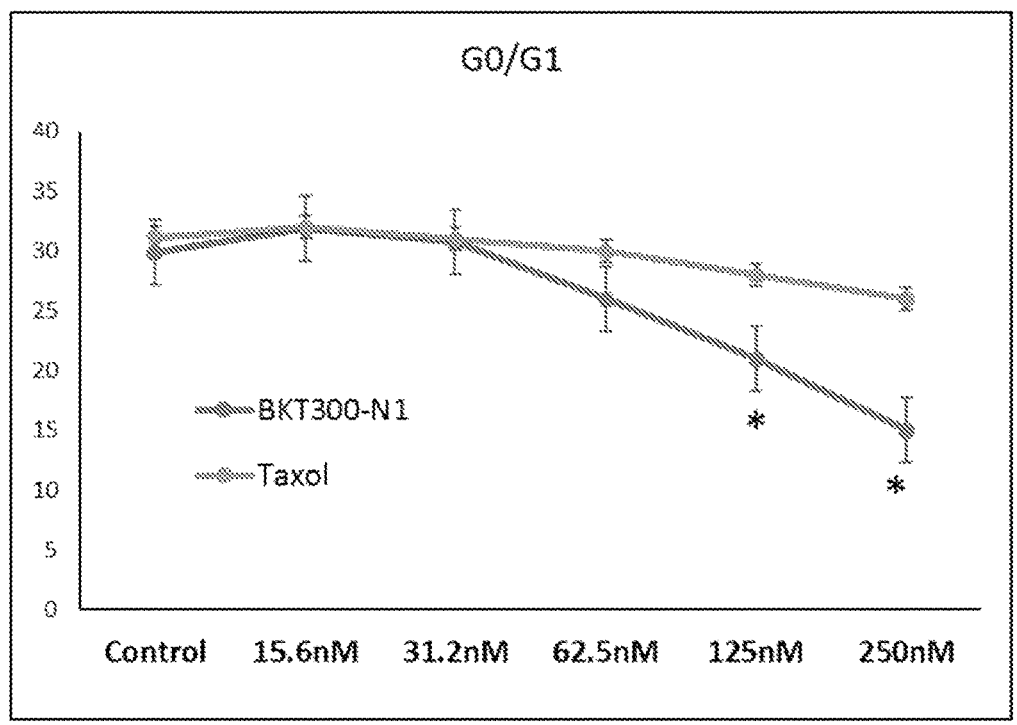
Figure 18C:
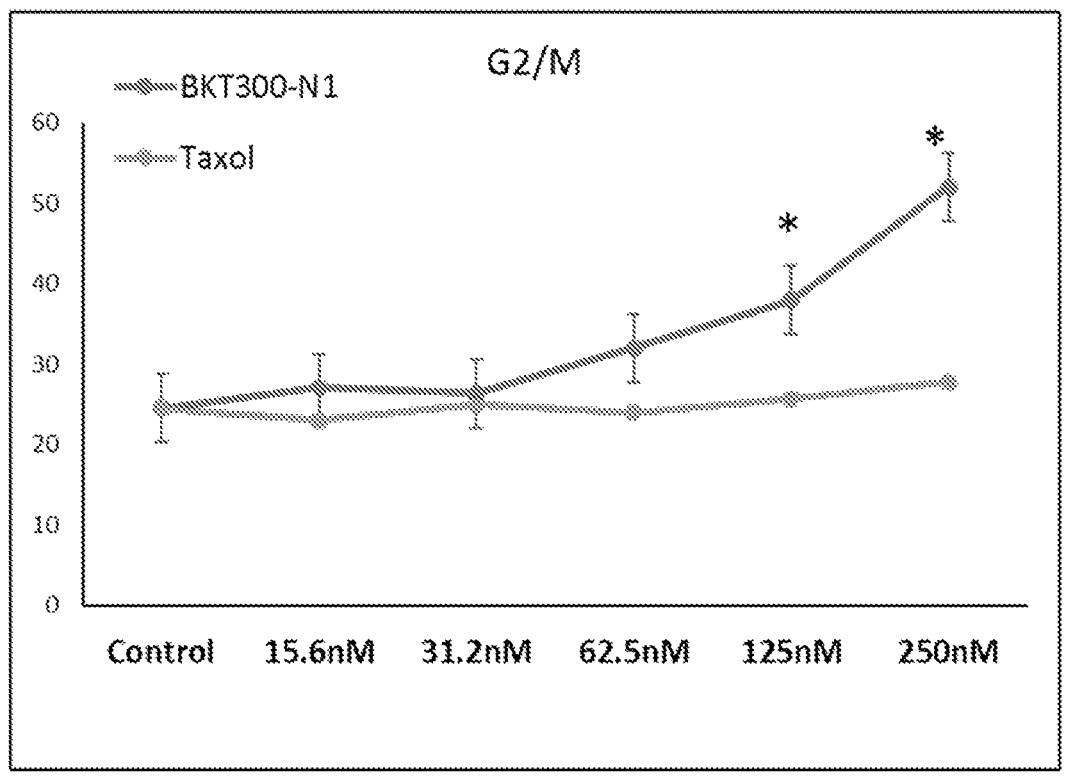

The obtained data is shown in FIGS. 18A-18C. BKT300-N1 was found to significantly affect the Taxol resistant cells HEY-T30 cells by increasing the level of dead cells at a concentration of 62.5 nM (FIG. 18A; red line), and by reducing the percentage of cells at G0/G1 phase at concentration of 125 nM (FIG. 18B; red line) while increasing the level of cells in G2/M phase at concentration of 125 nM (FIG. 18C; red line).

In contrast, no significant effects of Taxol was observed on HEY-T30 resistant cells in any of the tested concentrations (FIGS. 18A-18C; green lines).

These data demonstrate the therapeutical potential of BKT300-N1 in affecting (arresting) growth and viability of cancer cells that are resistant to taxol.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating cancer in a subject in need thereof, the method comprising co-administering to the subject at least one anti-cancer agent and a compound represented by Formula Ia and/or Ib:

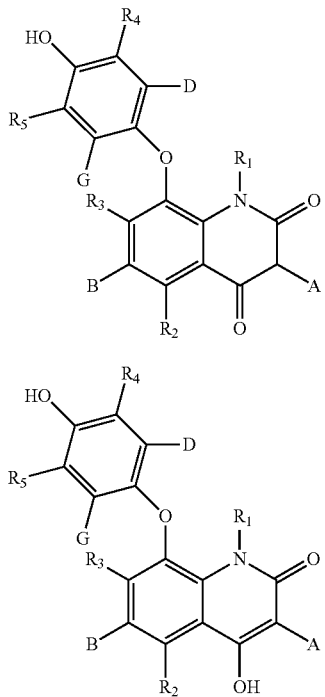

Formula IIa

Formula IIb wherein:
A is an alkyl being at least 4 carbon atoms in length;
B is selected from hydroxy and alkoxy;
D and G are each independently selected from hydrogen, hydroxy, alkoxy and alkyl, provided that at least one of D and G is hydrogen;
E is hydroxy;
$R_1$ is selected from hydrogen and alkyl; and
each of $R_2$-$R_5$ is independently selected from hydrogen, hydroxy, halo, alkoxy, thioalkoxy, thiol, thioalkoxy and amine,
wherein said at least one anti-cancer agent is selected from acivicin; aclarubicin; acodazole hydrochloride; acronine; adriamycin; Adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; combrestatin A-4 phosphate; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ombrabulin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofuirin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vincristine sulfate; vindesine; vindesine sulfate; vinepidinee; vinglycinate; vinleurosine; vinorelbine tartrate; vinrosidine; vinzolidine; vorozole; zeniplatin; zinostatin; zorubicin hydrochloride; an anti-cancer immune modulator agent, and any combination thereof.

2. The method of claim 1, wherein B is alkoxy.

3. The method of claim 1, wherein one of D and G is alkoxy.

4. The method of claim 1, wherein when one of D and G is alkyl, said alkyl is at least 4 carbon atoms in length.

5. The method of claim 1, wherein each of $R_1$-$R_5$ is hydrogen.

6. The method of claim 1, represented by Formula IIa or IIb:

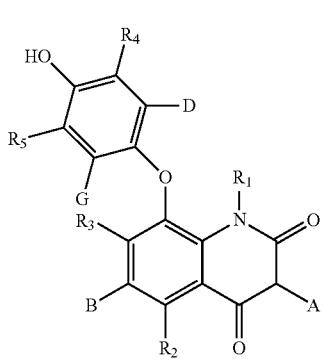

Formula IIa

-continued

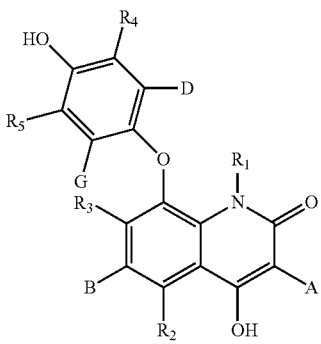

Formula IIb wherein

A is an alkyl being at least 4 carbon atoms in length;

B is selected from hydroxy and alkoxy;

D and G are each independently selected from hydrogen, hydroxy, alkoxy and alkyl, provided that at least one of D and G is hydrogen;

$R_1$ is selected from hydrogen and alkyl; and each of $R_2$-$R_5$ is independently selected from hydrogen, hydroxy, halo, alkoxy, thioalkoxy, thiol, thioalkoxy and amine.

7. The method of claim 6, wherein each of $R_1$-$R_5$ is hydrogen.

8. The method of claim 6, wherein at least one of D and G is alkoxy.

9. The method of claim 6, wherein B is alkoxy.

10. The method of claim 1, wherein the compound is:

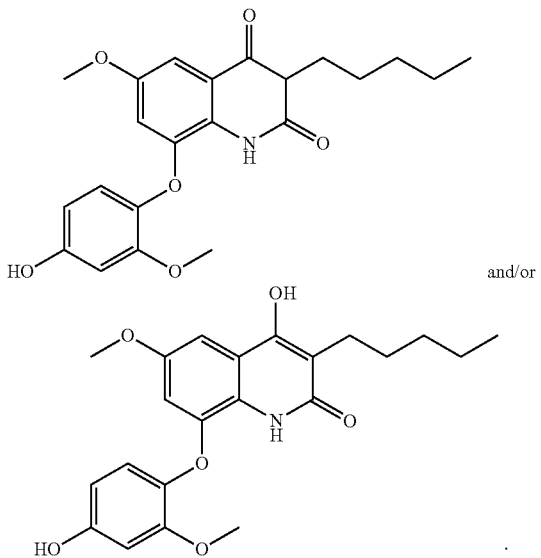

and/or

11. The method of claim 1, wherein the cancer is selected from a leukemia, a melanoma, a lung cancer, a lymphoma, a myeloma, a pancreatic cancer, an ovarian cancer, a liver cancer, a brain cancer, a colorectal cancer and a prostate cancer.

12. The method of claim 1, wherein the cancer is selected from colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors, endometrial carcinoma, dermatofibrosarcoma protuberans, gallbladder carcinoma, biliary tract tumors, prostate cancer, prostate adenocarcinoma, renal cancer, Wilms' tumor type 2 or type 1, liver cancer, hepatoblastoma, hepatocellular carcinoma, hepatocellular cancer, bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma, ductal breast cancer, invasive intraductal breast cancer, sporadic breast cancer, susceptibility to breast cancer, type 4 breast cancer, breast cancer-1, breast cancer-3, breast-ovarian cancer, squamous cell carcinoma, head and neck cancer, neurogenic tumor, astrocytoma, ganglioblastoma, neuroblastoma, lymphomas, Hodgkin's disease, non-Hodgkin's lymphoma, B-cell lymphoma, Diffuse large B-cell lymphoma (DLBCL), Burkitt lymphoma, cutaneous T-cell lymphoma, histiocytic lymphoma, lymphoblastic lymphoma, T-cell lymphoma, thymic lymphoma, gliomas, adenocarcinoma, adrenal tumor, hereditary adrenocortical carcinoma, brain malignancy (tumor), bronchogenic large cell carcinoma, carcinoma, ependimoblastoma, epithelioma, erythroleukemia, fibrosarcoma, giant cell tumor, glial tumor, glioblastoma, glioma hepatoma, heterohybridoma, heteromyeloma, histiocytoma, hybridoma, hypernephroma, insulinoma, islet tumor, keratoma, leiomyoblastoma, leiomyosarcoma, leukemia, acute lymphatic leukemia, acute lymphoblastic leukemia, acute lymphoblastic pre-B cell leukemia, acute lymphoblastic T cell leukemia, acute megakaryoblastic leukemia, monocytic leukemia, acute myelogenous leukemia, acute myeloid leukemia, acute myeloid leukemia with eosinophilia, B-cell leukemia, basophilic leukemia, chronic myeloid leukemia, chronic B-cell leukemia, eosinophilic leukemia, Friend leukemia, granulocytic or myelocytic leukemia, hairy cell leukemia, lymphocytic leukemia, megakaryoblastic leukemia, monocytic leukemia, monocytic-macrophage leukemia, myeloblastic leukemia, myeloid leukemia, myelomonocytic leukemia, plasma cell leukemia, pre-B cell leukemia, promyelocytic leukemia, subacute leukemia, T-cell leukemia, lymphoid neoplasm, predisposition to myeloid malignancy, acute nonlymphocytic leukemia, lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma, papilloma, transitional cell, pheochromocytoma, pituitary tumor (invasive), plasmacytoma, retinoblastoma, rhabdomyosarcoma, sarcoma, Ewing's sarcoma, histiocytic cell sarcoma, Jensen sarcoma, osteogenic sarcoma, reticulum cell sarcoma, schwannoma, subcutaneous tumor, teratocarcinoma, teratoma, testicular tumor, thymoma and trichoepithelioma, gastric cancer, fibrosarcoma, glioblastoma multiforme, multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

13. The method of claim 1, wherein the cancer is selected from pancreatic cancer, breast cancer, hepatocellular carcinoma, neuroblastoma, neuroendocrine cancer, renal cancer, bladder cancer, uterus cancer, testicles cancer, head and neck cancer, bowel cancer and sarcoma.

14. The method of claim 1, wherein the cancer is breast cancer.

15. The method of claim 1, wherein the cancer is characterized by expression of CXCR4.

16. The method of claim 1, wherein the cancer is a drug-resistant cancer.

17. The method of claim 16, wherein the cancer cells are resistant to said anti-agent cancer.

18. The method of claim 1, wherein said compound and said at least one additional anti-cancer agent act in synergy.

19. The method of claim 18, wherein said at least one additional anti-cancer agent is administered to the subject at a dose that is lower than a therapeutically effective amount thereof.

20. The method of claim 1, wherein said at least one additional anti-cancer agent is irinotecan or a salt thereof.

21. The method of claim 1, wherein said at least one additional anti-cancer agent is an anti-cancer immune modulator agent.

22. The method of claim 21, wherein said anti-cancer immune modulator agent is selected from a cancer antigen, a cancer vaccine, an anti-cancer antibody, a cytokine capable of inducing activation and/or proliferation of a T cell and an immune-check point regulator.

23. The method of claim 22, wherein said immune check point regulator modulates an activity of an immune-check point protein selected from PD1, PDL-1, B7H2, B7H4, CTLA-4, CD80, CD86, LAG-3, TIM-3, KIR, IDO, CD19, OX40, 4-1BB (CD137), CD27, CD70, CD40, GITR, CD28 and ICOS (CD278).

24. The method of claim 22, wherein said immune check point regulator is selected from anti-CTLA4, anti-PD-1, anti-PDL-1, CD40 agonist, 4-1BB agonist, GITR agonist and OX40 agonist.

25. The method of claim 1, wherein said compound and said at least one anti-cancer agent are co-administered to the subject sequentially or simultaneously.

26. The method of claim 1, wherein said compound and said at least one anti-cancer agent are co-formulated in the same pharmaceutical composition.

* * * * *